US008696674B2

(12) United States Patent
Howard et al.

(10) Patent No.: US 8,696,674 B2
(45) Date of Patent: Apr. 15, 2014

(54) TISSUE HARVESTING

(75) Inventors: Mark Howard, East Riding (GB); Mark Smith, Huby (GB); Stephen Curran, Elvington (GB); Graham Smith, Plaistow, NH (US); Elisabeth Hutson, Upper Poppleton (GB)

(73) Assignee: Smith & Nephew, Inc., Andover, MA (US)

( * ) Notice: Subject to any disclaimer, the term of this patent is extended or adjusted under 35 U.S.C. 154(b) by 1030 days.

(21) Appl. No.: 12/059,180

(22) Filed: Mar. 31, 2008

(65) Prior Publication Data

US 2008/0243029 A1 Oct. 2, 2008

Related U.S. Application Data

(60) Provisional application No. 60/909,253, filed on Mar. 30, 2007, provisional application No. 61/006,662, filed on Jan. 25, 2008, provisional application No. 60/992,210, filed on Dec. 4, 2007, provisional application No. 61/006,663, filed on Jan. 25, 2008.

(30) Foreign Application Priority Data

Aug. 8, 2007 (GB) .................................. 0715429.7

(51) Int. Cl.
*A61F 2/46* (2006.01)
*A61B 10/00* (2006.01)
*A61B 17/00* (2006.01)

(52) U.S. Cl.
USPC .............................. 606/86 R; 606/1; 600/565

(58) Field of Classification Search
USPC .................. 600/36, 562–568; 435/1.1, 283.1, 435/284.1, 287.1, 287.3, 289.1, 293.2, 435/297.1–297.4, 395, 403; 623/13.17, 623/23.63, 23.72, 909–911, 915–923; 606/1, 86 R
See application file for complete search history.

(56) References Cited

U.S. PATENT DOCUMENTS

| 5,077,012 | A |   | 12/1991 | Guirguis |
| 5,108,381 | A |   | 4/1992 | Kolozsi |
| 5,607,474 | A |   | 3/1997 | Athanasiou et al. |
| 5,804,366 | A | * | 9/1998 | Hu et al. ......................... 435/1.1 |
| 5,876,452 | A |   | 3/1999 | Athanasiou et al. |
| 6,013,853 | A |   | 1/2000 | Athanasiou et al. |

(Continued)

FOREIGN PATENT DOCUMENTS

| DE | 3417248 A1 | 11/1985 |
| EP | 0669105 A2 | 8/1995 |

(Continued)

OTHER PUBLICATIONS

International Search Report and Written Opinion for PCT/US2008/059624 Dated Jul. 17, 2008.

(Continued)

*Primary Examiner* — Brian Szmal
*Assistant Examiner* — Megan Leedy
(74) *Attorney, Agent, or Firm* — David L. Fox; JL Salazar Law Firm

(57) ABSTRACT

The present disclosure relates to a tissue collection apparatus including a housing defining an inlet and an outlet and a tissue scaffold suitable for disposal within the housing, the tissue scaffold configured to be loaded with the tissue under the application of an aspiration force applied through the tissue collection apparatus.

9 Claims, 50 Drawing Sheets

(56) References Cited

U.S. PATENT DOCUMENTS

| | | |
|---|---|---|
| 6,071,284 A | 6/2000 | Fox |
| 6,299,763 B1 | 10/2001 | Ashman |
| 7,115,100 B2 | 10/2006 | McRury et al. |
| 7,611,473 B2 | 11/2009 | Boock et al. |
| 2003/0114936 A1 | 6/2003 | Sherwood et al. |
| 2003/0130594 A1 | 7/2003 | Hynes et al. |
| 2004/0078090 A1 | 4/2004 | Binette et al. |
| 2004/0193071 A1 | 9/2004 | Binette et al. |
| 2005/0038520 A1 | 2/2005 | Binette et al. |
| 2005/0059905 A1 | 3/2005 | Boock et al. |
| 2005/0125077 A1 | 6/2005 | Harmon et al. |
| 2007/0016100 A1 | 1/2007 | Miller |

FOREIGN PATENT DOCUMENTS

| | | |
|---|---|---|
| EP | 1 378 209 A1 | 1/2004 |
| EP | 2139400 B1 | 1/2011 |
| WO | WO9315694 A1 | 8/1993 |
| WO | WO9959500 A2 | 11/1999 |
| WO | WO03073945 A1 | 9/2003 |
| WO | 2005110278 A2 | 11/2005 |
| WO | WO2006098293 A1 | 9/2006 |

OTHER PUBLICATIONS

Patent Examination Report No. 1 for Australian Application No. 2008232461, mailed Sep. 12, 2012.
International Search Report for International Application No. PCT/US2008/059624, mailed Jul. 17, 2008.
International Prelimininary Report on Patentability for International Application No. PCT/US2008/059624, issued Oct. 6, 2009.
Notice of Reasons for Rejection for Japanese Application No. 2010-501274, mailed Dec. 11, 2012.
Notice of Reasons for Rejection for Japanese Application No. 2010-501291, mailed Dec. 11, 2012.
International Search Report for International Application No. PCT/US2008/058821, mailed Jul. 18, 2008.
International Preliminary Report on Patentability for International Application No. PCT/US2008/058821, issued Oct. 6, 2009.
Patent Examination Report No. 1 for Australian Application No. 2008232516, mailed Jul. 23, 2012.
Communication Pursuant to Article 94(3) EPC for European Application No. 08744717.3, mailed Jan. 26, 2010.
Patent Examination Report No. 2 for Australian Application No. 2008232516, mailed May 21, 2013, 3 pages.
English Translation and Notice of Reasons for Rejection for Japanese Patent Application No. 2010-501291 dated Jul. 23, 2013, 7 pages.

* cited by examiner

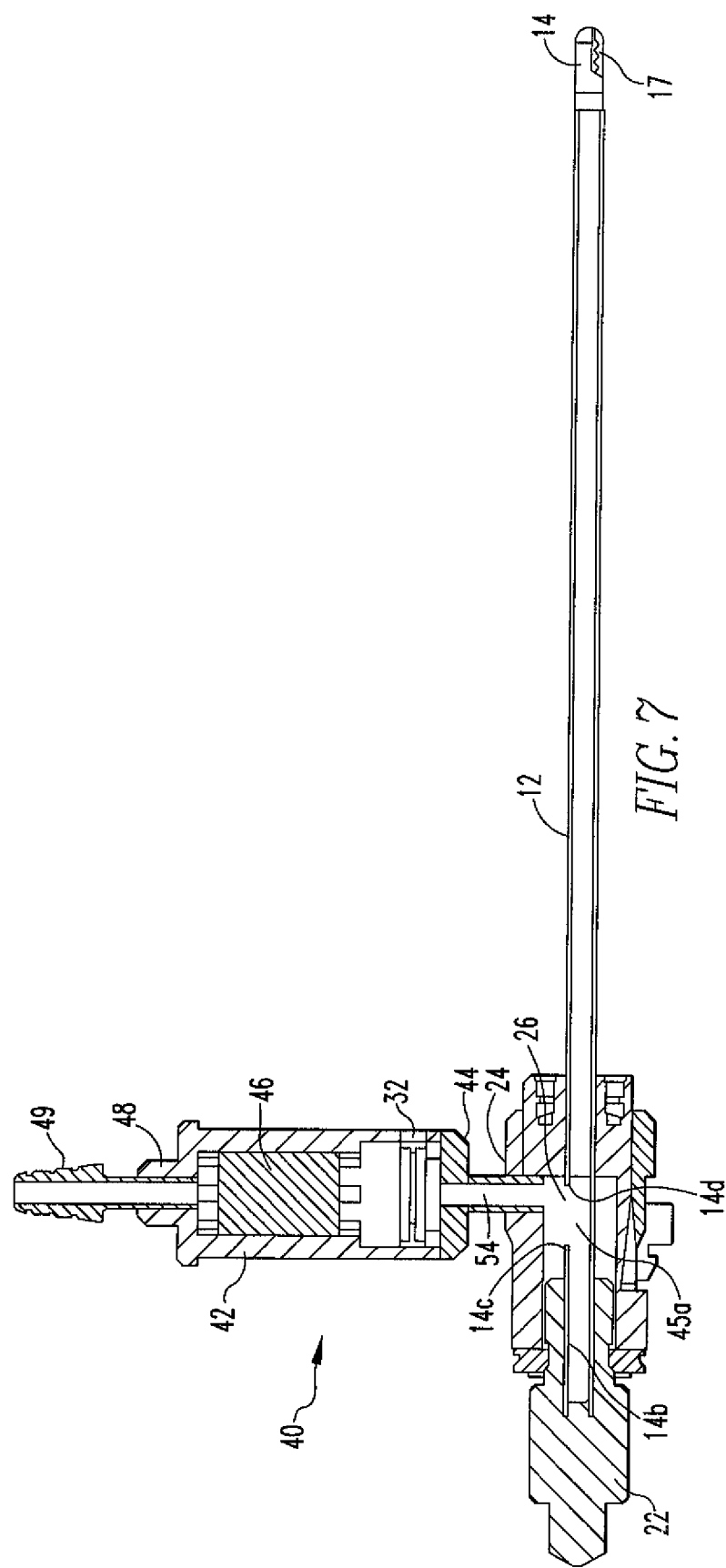

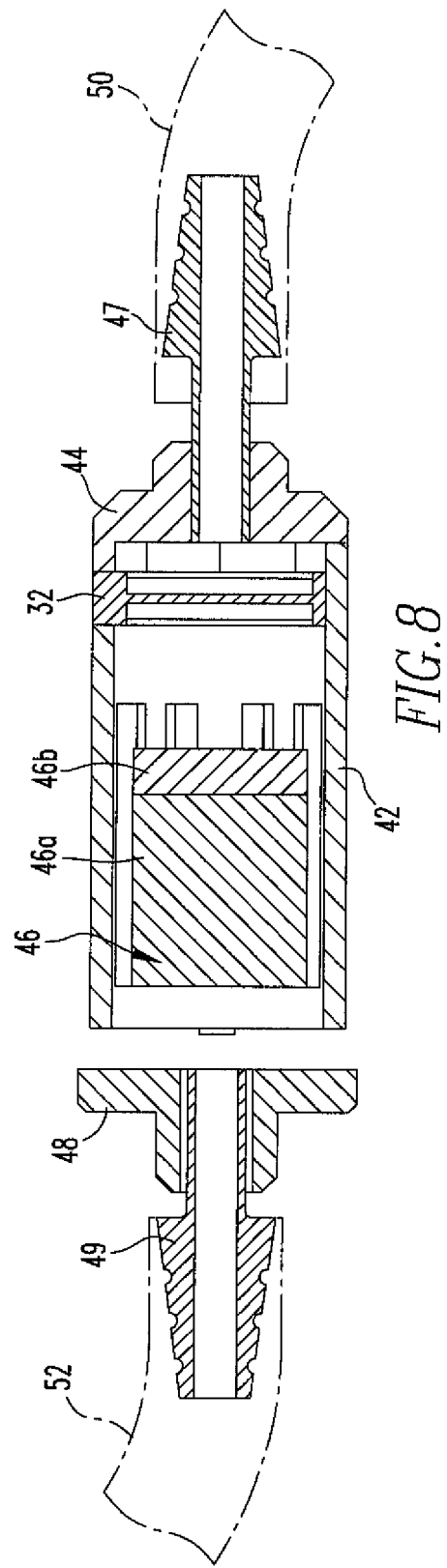

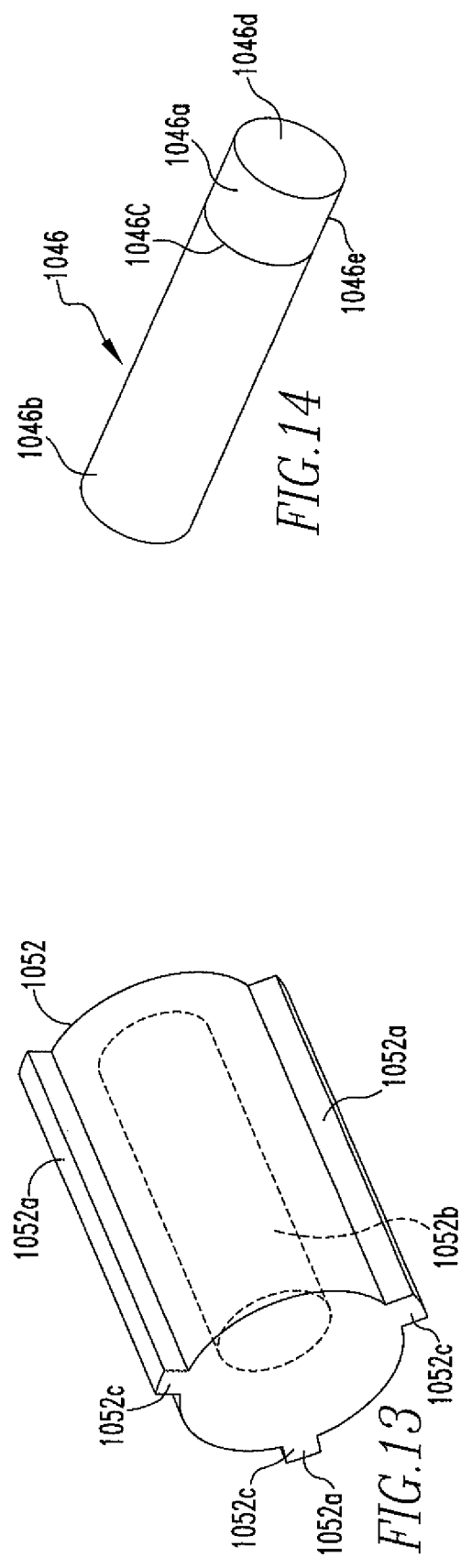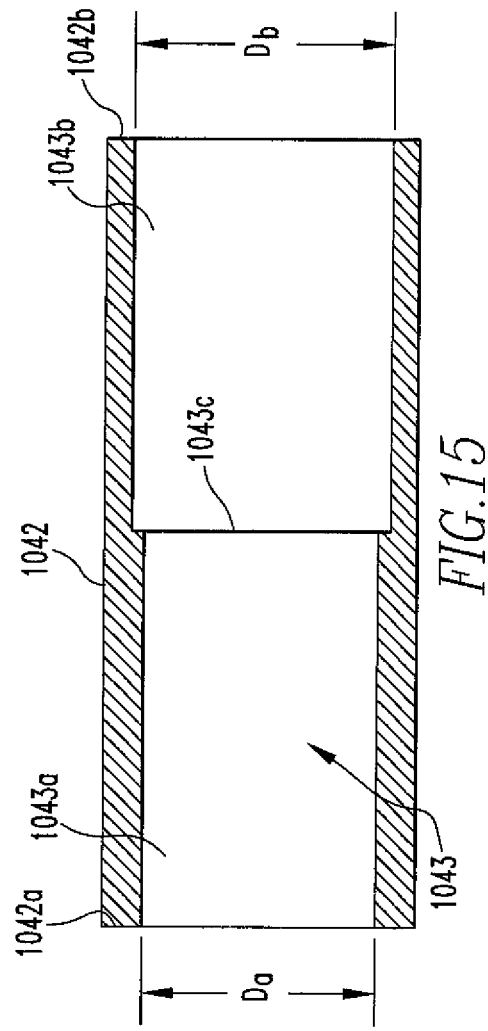

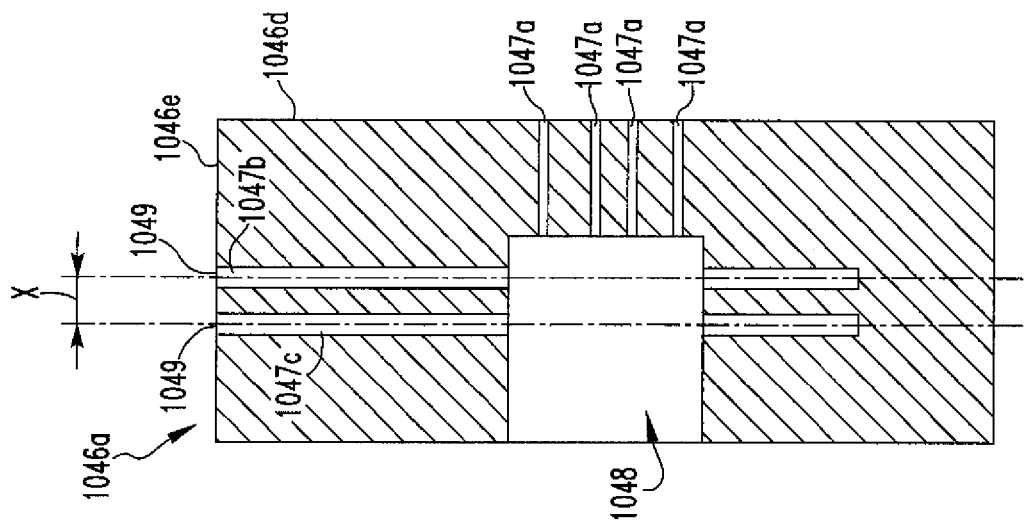
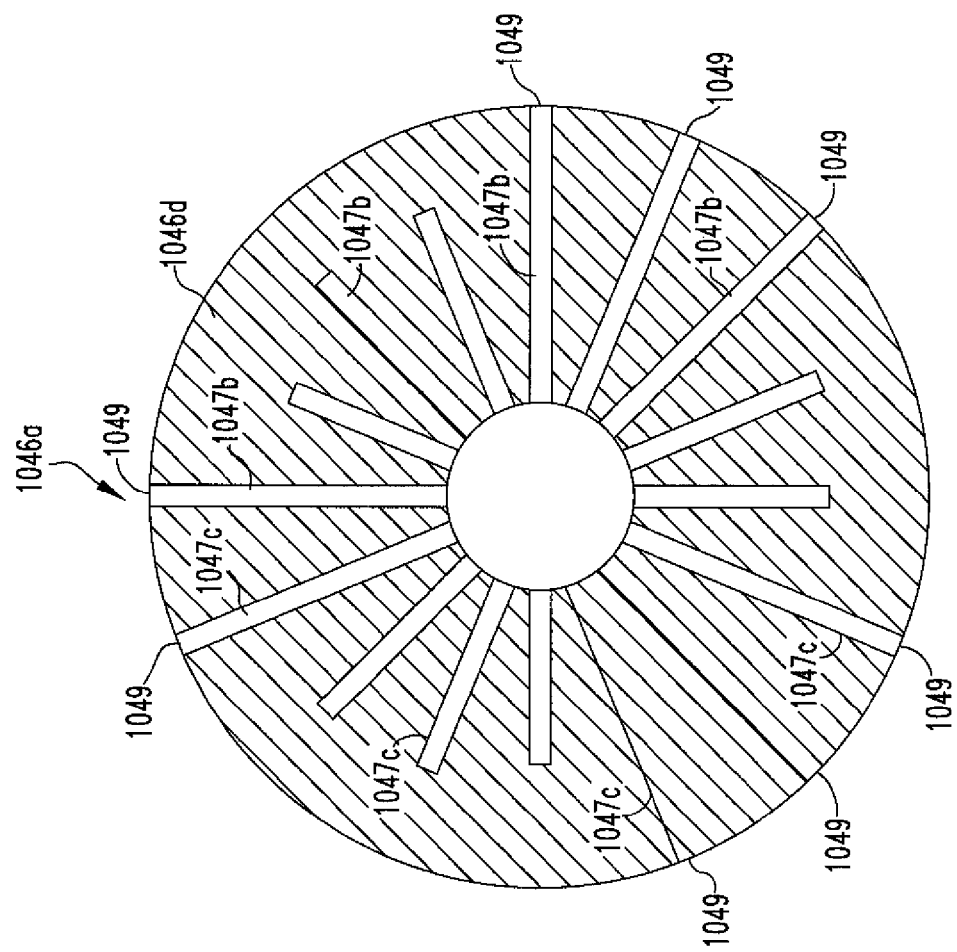

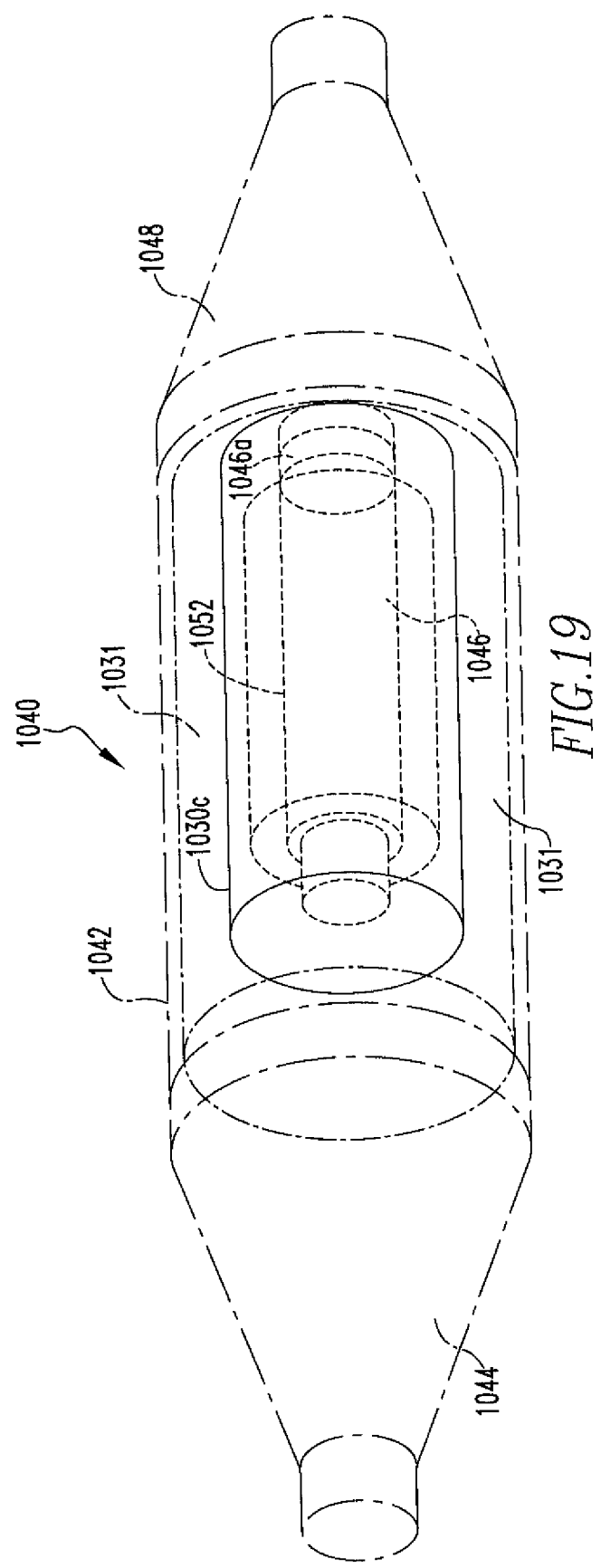

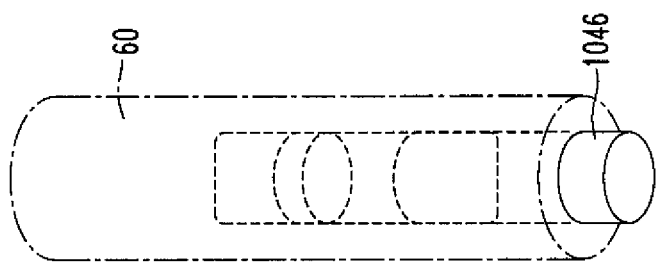
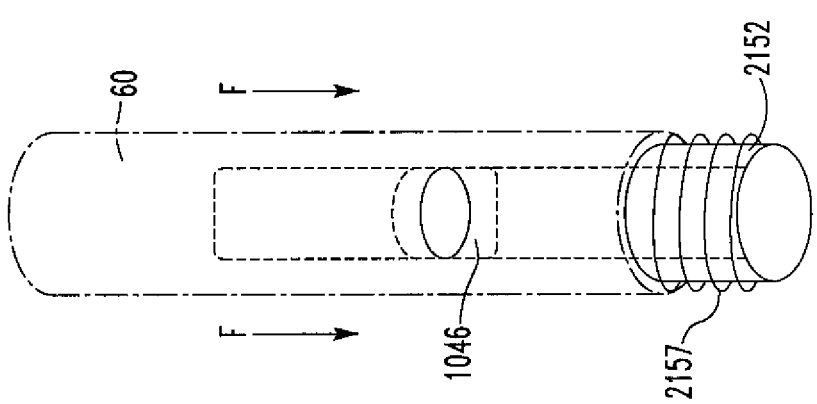
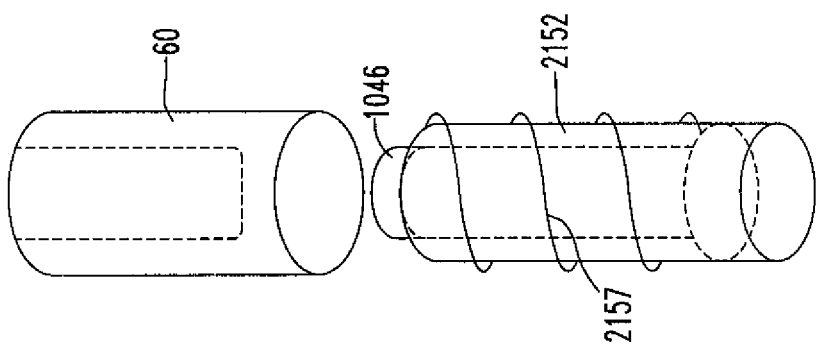

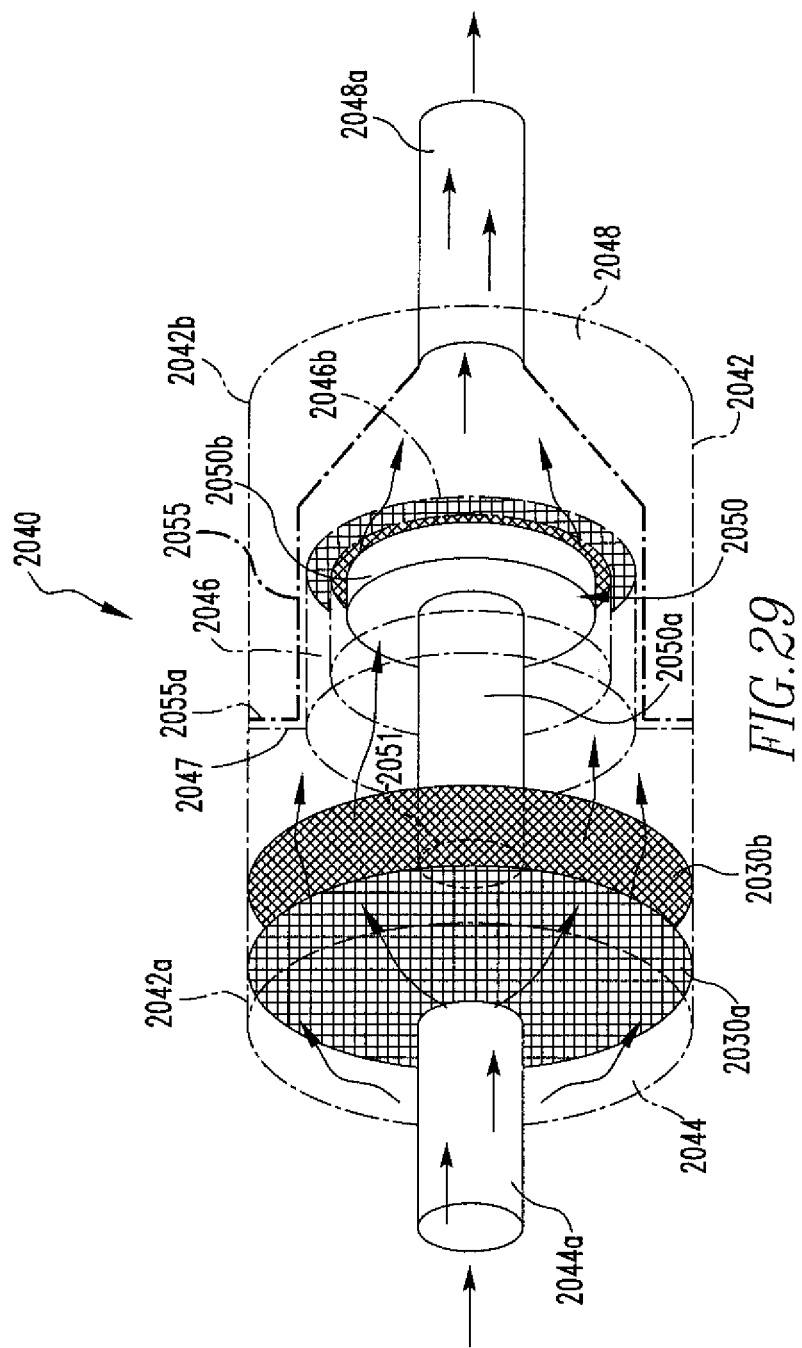

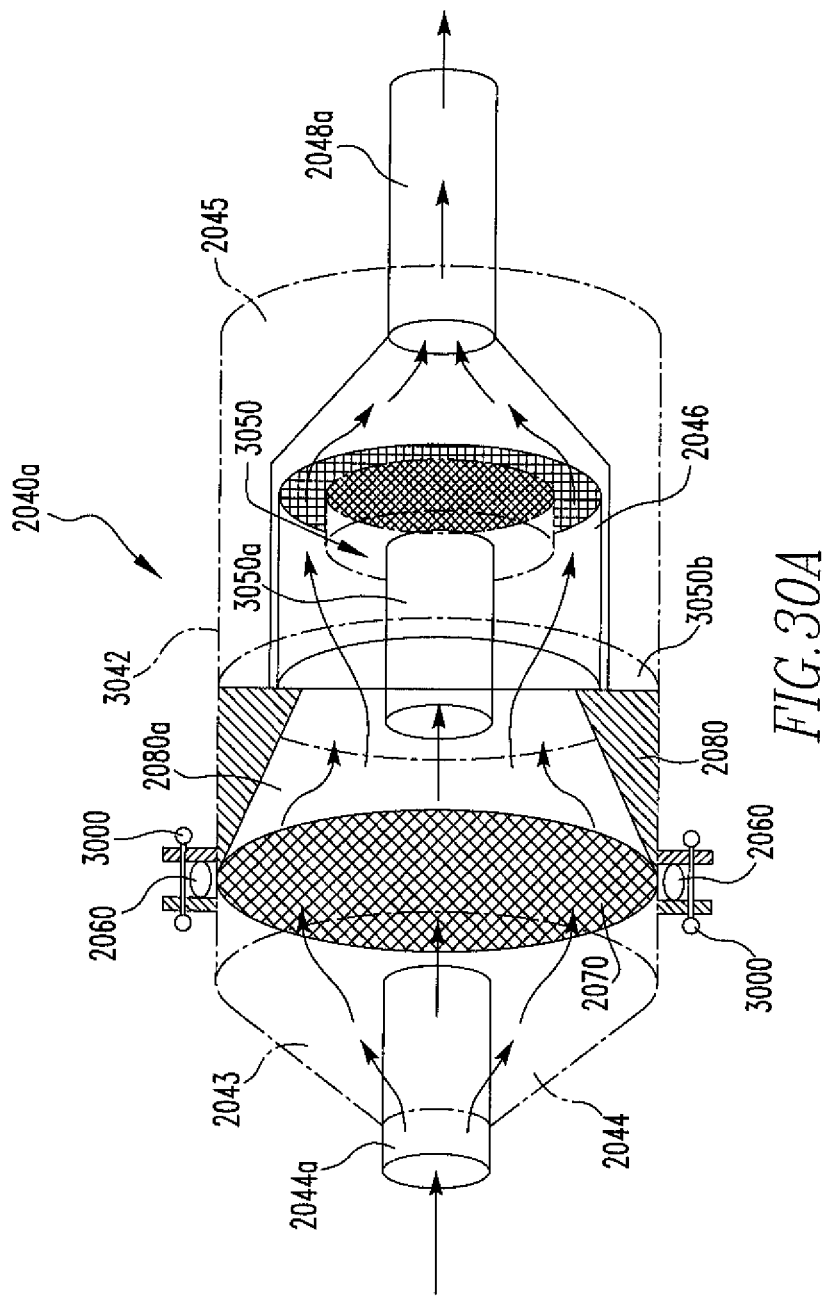

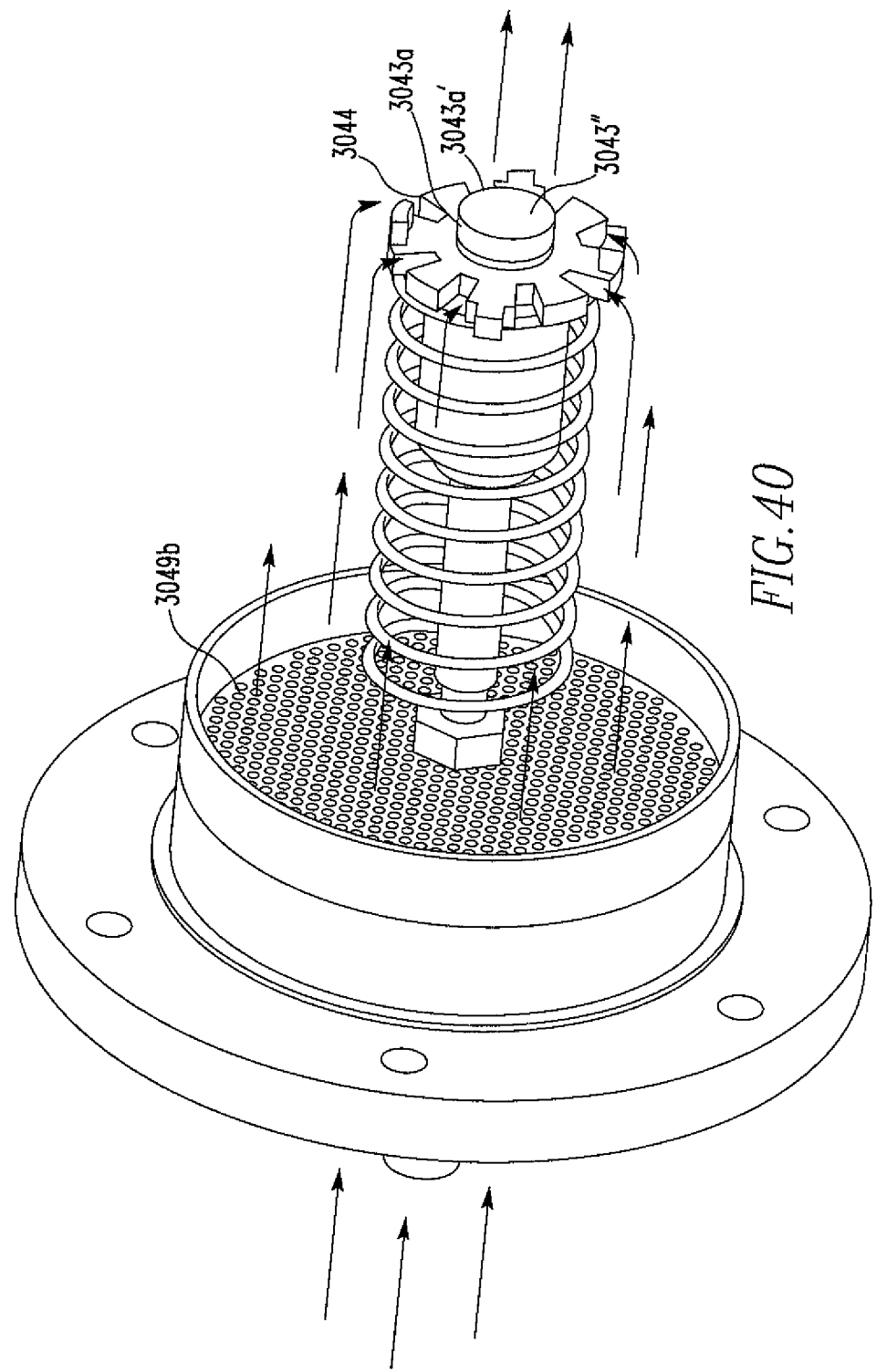

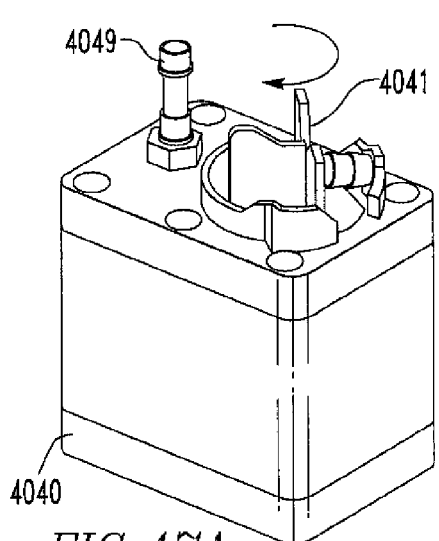
FIG. 47A
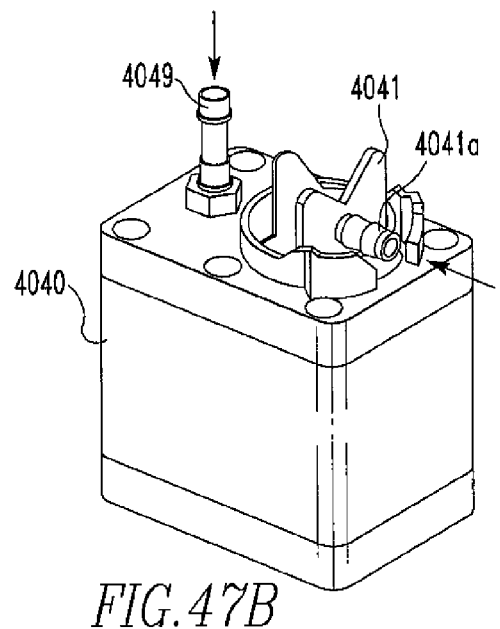
FIG. 47B
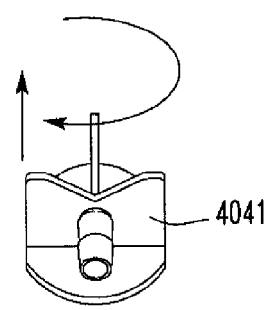
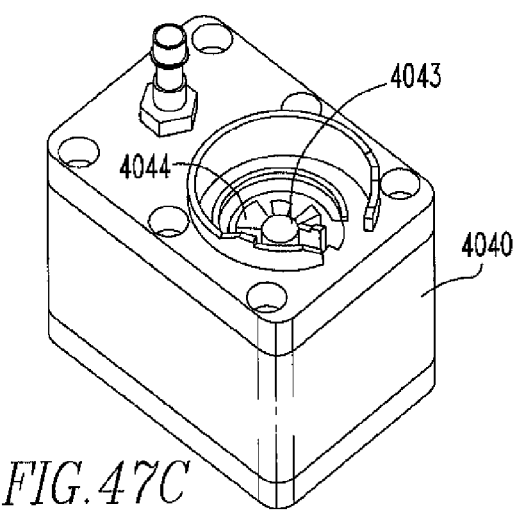
FIG. 47C
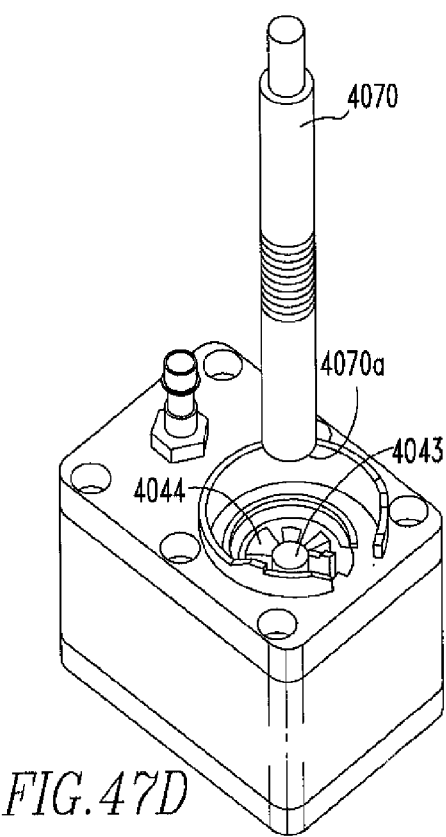
FIG. 47D

TISSUE HARVESTING

CROSS-REFERENCE TO RELATED APPLICATIONS

This application claims priority to U.S. application Ser. No. 60/909,253 filed on Mar. 30, 2007, U.S. application Ser. No. 60/992,210 filed on Dec. 4, 2007, U.S. application Ser. No. 61/006,663 filed on Jan. 25, 2008, U.S. application Ser. No. 61/006,662 filed on Jan. 25, 2008, and UK Provisional Application 0715429.7 filed on Aug. 8, 2007, the disclosures of which are herein incorporated in their entirety.

TECHNICAL FIELD

The present disclosure relates to tissue harvesting.

BACKGROUND

The tissue harvesting techniques described below can be used to repair, regenerate and/or augment tissue in a range of surgical or cosmetic applications.

Trauma to the articular surface is a common injury in sports. The symptoms arising from such damage include pain, joint locking, instability, and stiffness, and the damage predisposes the cartilage and joint to wear and degeneration which can lead to osteoarthritis and the need for total knee replacement. For example, the tissue harvesting techniques can be used to treat focal and degenerative cartilage lesions before a total joint replacement is indicated and can postpone or obviate the need for a total joint replacement. Articular cartilage lines the ends of bones and facilitates frictionless movement of joints. Damage to the cartilage caused by injury or disease does not heal and the pathological changes resulting from this damage can be a source of great pain; limiting mobility and having a significant detrimental impact on the quality of life. Over time, lesions are likely to degenerate into osteoarthritis. Injury is not the only cause of osteoarthritis, with genetics, obesity, joint biomechanics, diet and age all playing a role.

Known surgical techniques for treating damaged cartilage include lavage and debridement (joint is flushed with fluid and damaged tissue removed providing temporary symptom relief); microfracture (penetration of the subchondral bone to stimulate bleeding in to the cartilage lesion in an effort to promote a fibrocartilage healing response); periosteal grafts (autologous periosteum is grafted into the defect site and sutured or glued into place); mosaicplasty (plugs of cartilage and bone are harvested from low weight bearing regions of the joint and transplanted into the defect); and autologous chondrocyte implantation (ACI) (cells are isolated and expanded from a cartilage biopsy from a non-weight bearing location, and the cells are re-introduced into the defect in a second procedure approximately six weeks later either in suspension or on a scaffold (Matrix-guided ACI-MACI)).

SUMMARY

Trauma to the articular surface is a common injury in sports. The symptoms arising from such damage include pain, joint locking, instability, and stiffness, and the damage predisposes the cartilage and joint to wear and degeneration which can lead to osteoarthritis and the need for total knee replacement. The tissue harvesting techniques described below can be used to treat focal and degenerative cartilage lesions before a total joint replacement is indicated and can postpone or obviate the need for a total joint replacement. The techniques enable the surgical team to purify a unique population of repair cells from tissue from the patient, such as, for example, synovial/adipose tissue, and deliver the cells back into the patient's joint to stimulate a hyaline-like cartilage repair in a single surgical procedure. The repair cells are harvested arthroscopically from a site local to the defect (i.e. within the joint) and delivered directly onto a biocompatible scaffold, and in some implementations, onto particular regions of the scaffold, which is then implanted at the repair site.

In implementations of the disclosure, the adipose tissue harvested is a fat pad or corpus adiposum, which is a localized accumulation of encapsulated adipose tissue. Fat pads can be found, for example in the check (corpus adiposum buccae) and also found within certain joints where they are referred to as the infrapatellar, navicular, olecranon, scaphoid, pronator quadratus, and preachilles fat pads. These pads may act as a cushion to absorb forces generated across the joint and also may help to distribute lubricants in the joint cavity.

The infrapatellar fat pad, also referred to as Hoffa's pad and adipose synovium includes synovium and subsynovial adipose tissues and lies beneath the patella (kneecap) separating it from the femoral condyle. The infrapatellar fat pad varies in size and volume, but generally includes two large basal prominences lying on either side of the intrachondylar notch. In situations where forces are directed at the patella the infrapatllar fat pad acts as a shock absorber, protecting the underlying structures. During trauma the fat pad undergoes a number of changes, which include, without limitation, the fat pad volume increasing secondary to oedema and haemorrhage due to increased subsynovial vascularisation and the subsequent infiltration of the fat pad with macrophages.

We have found that by harvesting a defined size fragment of fat pad tissue, comprising progenitor cells and reintroducing this fragment in combination with a biocompatible scaffold, such as a gel, into another site within the body, it is possible to generate tissue types that are different from the tissue fragment following exposure of the fragment to environmental factors.

It is envisaged that the progenitor cells contained within the fragments of fat pad could be directed along, for instance, the osteogenic, adipogenic, chondrogenic, myogenic, neurogenic lineages giving rise to bone, cartilage, muscle or nerve tissue.

Once fat pad fragments are implanted into the site, the fat pad fragments will gradually remodel thereby allowing the progenitor cells to migrate out of the fragment and integrate into the surrounding tissue, thereby allowing the progenitor cells to differentiate into the appropriate endogenous cell type(s).

The fat pad tissue can be autogeneic tissue, allogeneic tissue, xenogeneic tissue and combinations thereof.

The use of autogeneic tissue is particularly desirable as it substantially reduces the potential for an immunogenic host response and tissue rejection.

If the autogenic fat pad is to be used, a specific consideration for the surgeon is how readily accessible the fat pad is during the primary surgical procedure. For example, if a surgeon is repairing a cartilage defect within the femoral plateau, then it would be appropriate to use the infrapatellar fat pad. This will minimise the incisions that the surgeon has to make and therefore improve the outcome and the welfare of patient.

Using autologous tissue as a source for cartilage repair implants is often limited due to a number of problems including: availability, source, pain and enrichment. The infrapatellar fat pad is a joint tissue that is easily accessible to the orthopedic surgeon and is present in sufficient quantity to load a number of scaffolds for use in cartilage repair, particularly of focal defects. Furthermore the use of the infrapatellar fat pad substantially reduces the possibility of secondary site morbidity when compared to other tissue sources, such as bone marrow aspirations and substantially reduces the need to enrich the progenitor cells to show therapeutic effect.

In one general aspect, the present disclosure relates to a tissue collection apparatus comprising a housing defining an inlet and an outlet, and a tissue scaffold suitable for disposal within the housing, the tissue scaffold configured to be loaded with tissue under the application of an aspiration force applied through the tissue collection apparatus.

Implementations can include one or more of the following features. For example, the tissue scaffold comprises a first region and a second region, the two regions having dissimilar mechanical and porosity properties. The apparatus further comprises a sleeve disposed around the tissue scaffold, the sleeve configured to allow a tissue-containing fluid to flow through the tissue scaffold. The sleeve is configured to allow the tissue-containing fluid to flow only through the first region of the tissue scaffold. The sleeve is configured to release the tissue scaffold upon application of a downward force applied to the sleeve. The sleeve is compliant and compresses around the tissue scaffold upon application of a force applied to the sleeve thereby allowing access to the tissue scaffold for removal from the sleeve. The apparatus further comprises a filter disposed within the housing of the tissue collection apparatus. The filter defines a set of openings having an opening size of up to about 600 µm to about 1 mm, or of about 600 µm. The filter defines a plurality of openings having an opening size of about 2.4 mm, or of about 3 mm. The apparatus further comprises a set of fluid-flow pathways formed in the first region of the tissue scaffold, the pathways configured to permit flow of a tissue-containing fluid therethrough. One of the set of pathways comprises a diameter of about 500 µm and a second of the set of pathways comprises a diameter of about 300 µm. At least some of the pathways open as apertures at a periphery of the scaffold to provide points of entry for the tissue containing fluid into the scaffold. The outlet is in fluid communication with an aspiration source.

The tissue scaffold is cup-shaped. The apparatus further includes an insert, a portion of which is disposed within the tissue scaffold and is configured to limit the amount of tissue collected in the tissue scaffold. The insert is removably disposed within the tissue scaffold.

The inlet of the housing may be associated with a surgical instrument including an elongate outer tubular member defining a distal opening, an elongate inner tubular member rotatably received within the outer tubular member and defining an aspiration lumen, the elongate inner tubular member including a distal cutter adjacent the distal opening in the elongate outer tubular member, and a tissue collection device in fluid communication with the aspiration lumen of the elongate inner tubular member, the tissue collection device for receiving a tissue scaffold configured to be loaded with tissue under the application of an aspiration force applied through the tissue collection device to the aspiration lumen of the elongate inner tubular member to aspirate tissue therethrough.

A filter positioned between the elongate inner tubular member and the inlet of the housing. A hub is configured to receive a portion of the elongate outer tubular member and the inner tubular member. The hub includes a sidewall defining an aperture in fluid communication with the aspiration lumen of the elongate inner tubular member and the housing is configured to be coupled to the aperture such that the tissue scaffold is loaded with tissue during aspiration of the tissue from the aspiration lumen.

The tissue collection apparatus is releasably coupled to the aperture such that the tissue scaffold is loaded with tissue during aspiration of the tissue from the aspiration lumen. The tissue collection device is permanently coupled to the aperture such that the tissue scaffold is loaded with tissue during aspiration of the tissue from the aspiration lumen. The inner tubular member further defines an opening in a proximal region of the inner tubular member that is in fluid communication with the aspiration lumen. The hub defines an opening extending in a direction substantially transverse to the longitudinal axis of the elongate inner tubular member and in fluid communication with the aspiration lumen of the inner tubular member. A tubing connector is disposed in the hub opening. A first tubing is coupled to and between the tubing connector and the filter, and a second tubing coupled to and between the filter and the collection device. The filter is disposed within the housing. The housing further includes a removably coupled inlet connector. The inlet connector is disposed in the hub opening. A spacing is between the filter and the inlet connector is in the range of 30 mm to 40 mm. The housing further includes a tubing connector coupled thereto. The filter includes openings formed therein having an opening size of about 50 µm to about 600 µm. The filter includes openings formed therein having an opening size of about 300 µm to about 600 µm. The apparatus further includes a vacuum source coupled to the surgical instrument that is effective to uniformly load the fluid permeable tissue scaffold with tissue. The apparatus further includes a fluid permeable tissue scaffold configured to be loaded with tissue cut by the surgical blade.

In another general aspect, a method includes aspirating a cut tissue through an aspiration lumen of a cutter and loading a tissue scaffold of a tissue collection device with cut tissue under the application of an aspiration force applied through the tissue collection device to the aspiration lumen of the cutter to aspirate tissue therethrough.

Implementations can include one or more of the following features. For example, the method further comprises passing the cut tissue through a filter prior to the step of loading the tissue scaffold. The method further comprises removing the tissue scaffold from the tissue collection device. The cut tissue is synovial or adipose tissue. The loading step includes loading the tissue scaffold with cut tissue solely under the application of an aspiration force applied through the tissue collection device to the aspiration lumen of the cutter to aspirate tissue therethrough. Loading the tissue scaffold comprises loading a specific region of the tissue scaffold with the cut tissue. The tissue scaffold comprises a first phase and a second phase, and wherein only the first phase is loaded with the cut tissue. The method further comprises piercing the tissue scaffold to form a set of fluid-flow pathways in the tissue scaffold. Loading the tissue scaffold comprises loading the cut tissue into a first region, and not in another region, of the tissue scaffold. The tissue scaffold includes a first material forming a cartilage region and a second material forming a bone region of the tissue scaffold, and wherein the tissue fragments are loaded into the cartilage region. The tissue scaffold comprises an osteochondral plug. The tissue comprises synovium. The tissue comprises adipose.

In another general aspect, a kit for harvesting tissue comprises an elongate outer tubular member defining a distal opening, an elongate inner tubular member adapted to be rotatably received within the elongate outer tubular member therein defining an aspiration lumen, the elongate inner tubular member including a distal cutter, which in use, is adjacent the distal opening in the elongate outer tubular member, and a tissue collection device, which in use, is in fluid communication with the aspiration lumen of the elongate inner tubular member, the tissue collection device for receiving a tissue scaffold configured to be loaded with tissue under the application of an aspiration force applied through the tissue collection device to the aspiration lumen of the elongate inner tubular member to aspirate tissue therethrough.

Implementations can include one or more of the following features. For example, the kit further comprises the tissue scaffold, the scaffold being configured such that in use the scaffold is loaded with tissue under the application of an aspiration force applied through the tissue collection device to the aspiration lumen of the elongate inner tubular member to aspirate tissue therethrough. The kit further comprises a filter positioned between the elongate inner tubular member and the tissue collection device and in fluid communication with the aspiration lumen of the elongate inner tubular member. The filter is disposed within the tissue collection device. The tissue scaffold is configured to be capable of being loaded solely under the application of the aspiration force applied through the tissue collection device to the aspiration lumen of the elongate inner tubular member to aspirate tissue therethrough.

Advantages can include eliminating the risk of disease transmission and immune response associated with treatment using allograft; enabling cartilage repair procedures to be performed in focal lesions in older as well as young patients; minimizing damage to the donor site; isolating tissue fragments which are within a specific size range; minimizing intervention from the surgeon; and harvesting tissue, loading tissue onto a scaffold in an expedient manner, and implanting the scaffold for tissue repair in a sterile manner in a single surgical procedure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7 is a cross-section view of the blade of FIG. 6.

FIG. 8 illustrates removal of a tissue scaffold from the tissue collection device of FIG. 2.

FIG. 13 is a perspective view of the sleeve of the tissue collection device of FIGS. 10-12.

FIG. 14 is a perspective view of a tissue scaffold for use with the tissue collection device of FIGS. 10-12.

FIG. 15 is a cross-section view of the housing of FIGS. 10-12.

FIG. 16H is a front end view of an alternative implementation of the first region of the tissue scaffold of FIG. 14.

FIG. 16I is a cross-section view of the first region of the tissue scaffold of FIG. 16H.

FIG. 19 is a perspective view of an alternative implementation of the tissue collection device of FIG. 11.

FIGS. 21A-21C illustrate removal of a tissue scaffold from an implementation of the tissue collection device of FIG. 10.

FIG. 29 is a perspective view of an alternative implementation of a tissue collection device.

FIG. 30A is a perspective view of an alternative housing configuration of the tissue collection device of FIG. 29.

FIG. 40 is a perspective view illustrating the flow of tissue and fluid through the tissue collection apparatus of FIG. 34A.

FIGS. 47A-47D are perspective views illustrating use of the tissue collection apparatus of FIG. 34B.

DETAILED DESCRIPTION

Figure 1:
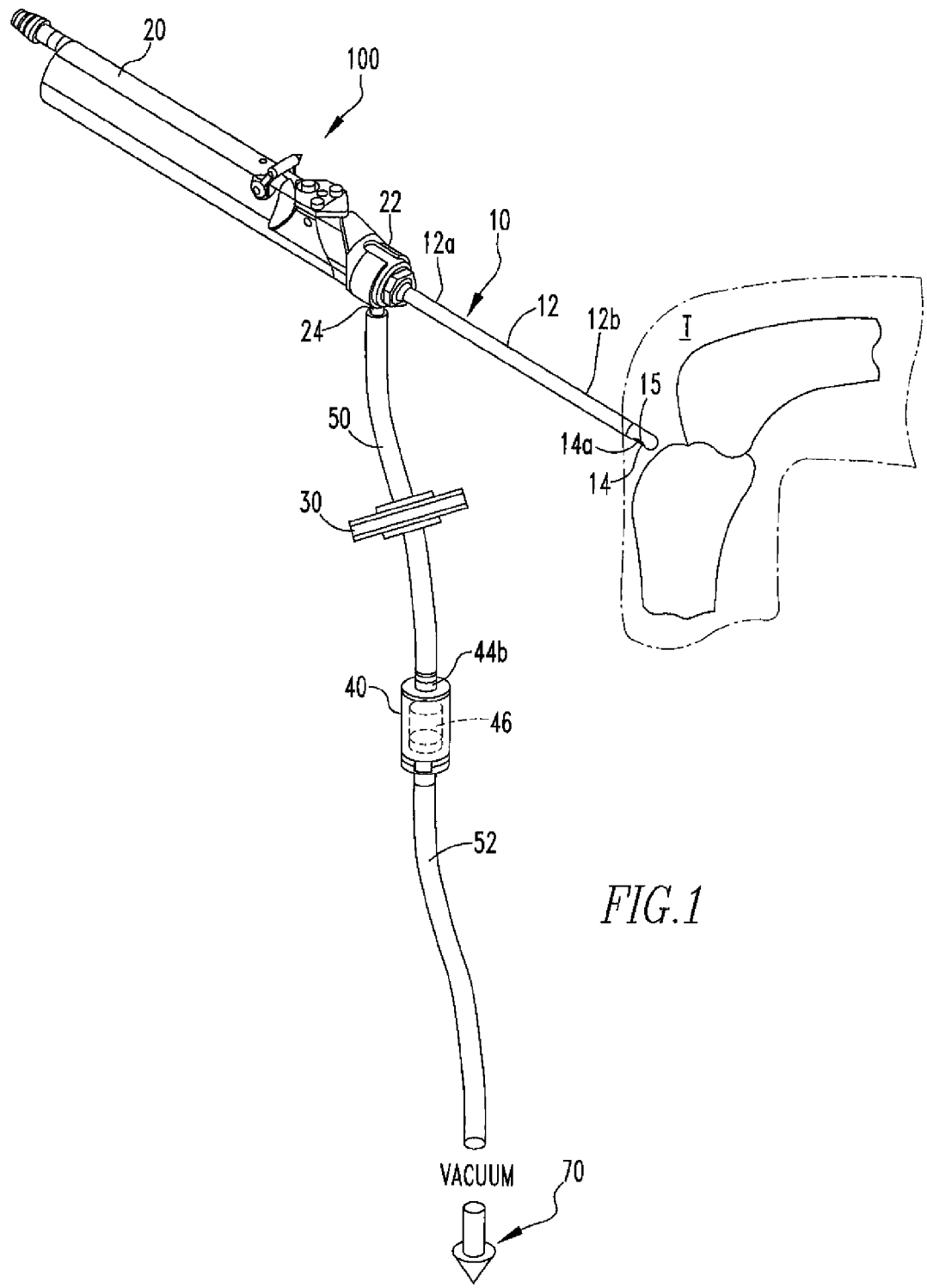
FIG. 1 is an illustration of a tissue harvesting assembly shown in use.

Referring to FIG. 1, a tissue harvesting assembly 100 includes a surgical blade 10 used to cut or resect bodily tissue T, such as synovial or adipose tissue, from a donor site, coupled to a tissue collection device 40 for collecting cut tissue aspirated through surgical blade 10. Within tissue collection device 40 is a tissue scaffold 46. Cut tissue under the application of the aspiration force applied through the tissue collection device 40 to the surgical blade 10 loads substantially throughout, and not merely onto the surface of, the tissue scaffold 46. As discussed below, during the same surgical procedure, the tissue loaded scaffold 46 can be implanted at a cartilage tissue repair site. Preferably, the donor site and the repair site are within the same joint to minimize trauma to the patient and provide for a more expedient surgical procedure.

Surgical blade 10 uses a tube-in-tube construction to shear tissue disposed between cutting edges of an elongate outer non-rotating tubular member 12 and an elongate inner rotating tubular member 14, as more fully explained in U.S. Pat. No. 5,871,493, which is incorporated herein by reference in its entirety. The surgical blade 10 includes a handpiece 20 coupled to the members 12, 14 via a hub 22. The outer tubular member 12 has a proximal end 12a fixed to the hub 22 and a distal end 12b defining an opening 15 forming a cutting port or window. The inner tubular member 14 is rotatably received in the outer tubular member 12 and has a distal end 14a with a cutting edge 17 (FIG. 6). The inner tubular member 14 defines an aspiration lumen 16 (FIG. 5) communicating with the cutting edge 17 to remove cut tissue and fluid from a surgical site. When the blade 10 is assembled, the cutting edge 17 of the inner tubular member 14 is positioned adjacent the opening 15 of the outer tubular member 12.

The tissue collection device 40 is coupled to the blade 10 via a flexible tubing 50. The flexible tubing 50 preferably includes a filter 30 positioned between the blade 10, and more particularly, the aspiration lumen 16 of the tubular member 14, and the tissue collection device 40 such that the filter 30 is in fluid communication with the aspiration lumen 16 of the inner tubular member 14. In the implementation of FIG. 1, filter 30 is coupled to a side port 24 of the hub 22 and to an inlet 44b of the tissue collection device 40 via the tubing 50. An exemplary filter for use with the implementations discussed herein is a 25 mm Delrin Filter Holder (Catalog No. 300-0001), available from VWR International Ltd. of Leicestershire, England, however, other known filters may be used. Filter 30 includes a screen (not shown) having openings formed therein each having an opening size of about 50 µm to about 1 mm, and in one particular implementation between about 50 µm to about 600 µm, so that only cut tissue sized in the range of less than about 50 µm to about 1 mm, and in the particular implementation between about 50 µm to about 600 µm, can pass through the filter to the tissue collection device. Such filtering assists to remove particles that are too large to efficiently load the tissue scaffold 46.

Figure 2:
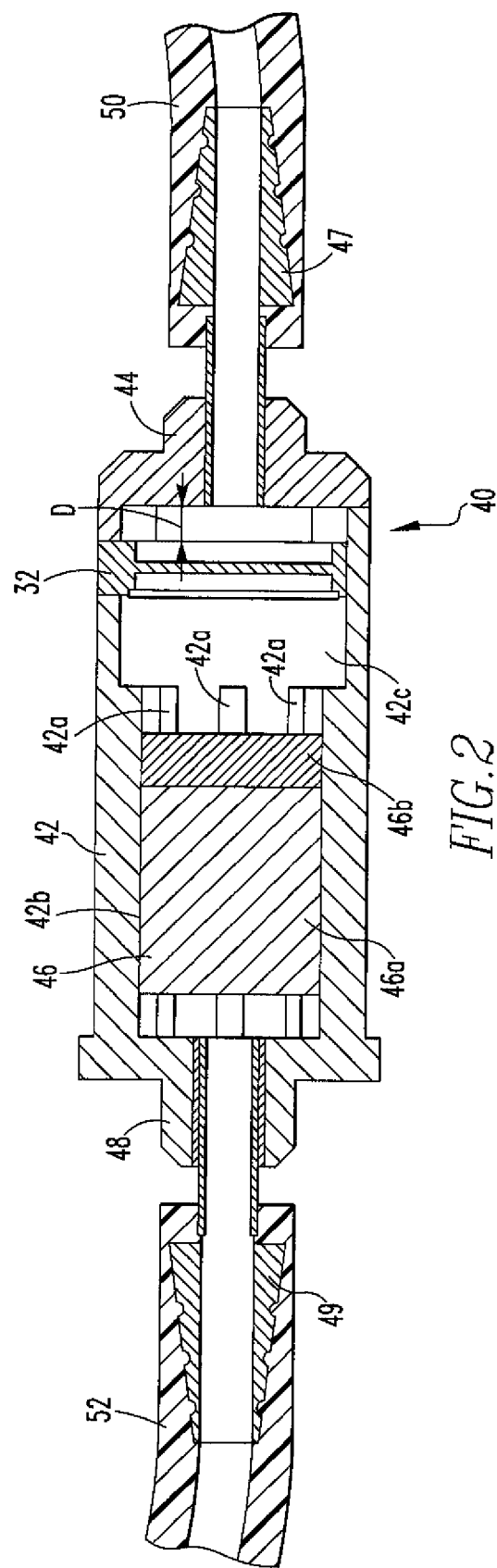
FIG. 2 is a cross-section view of a tissue collection device of the assembly of FIG. 1.
Figure 3:
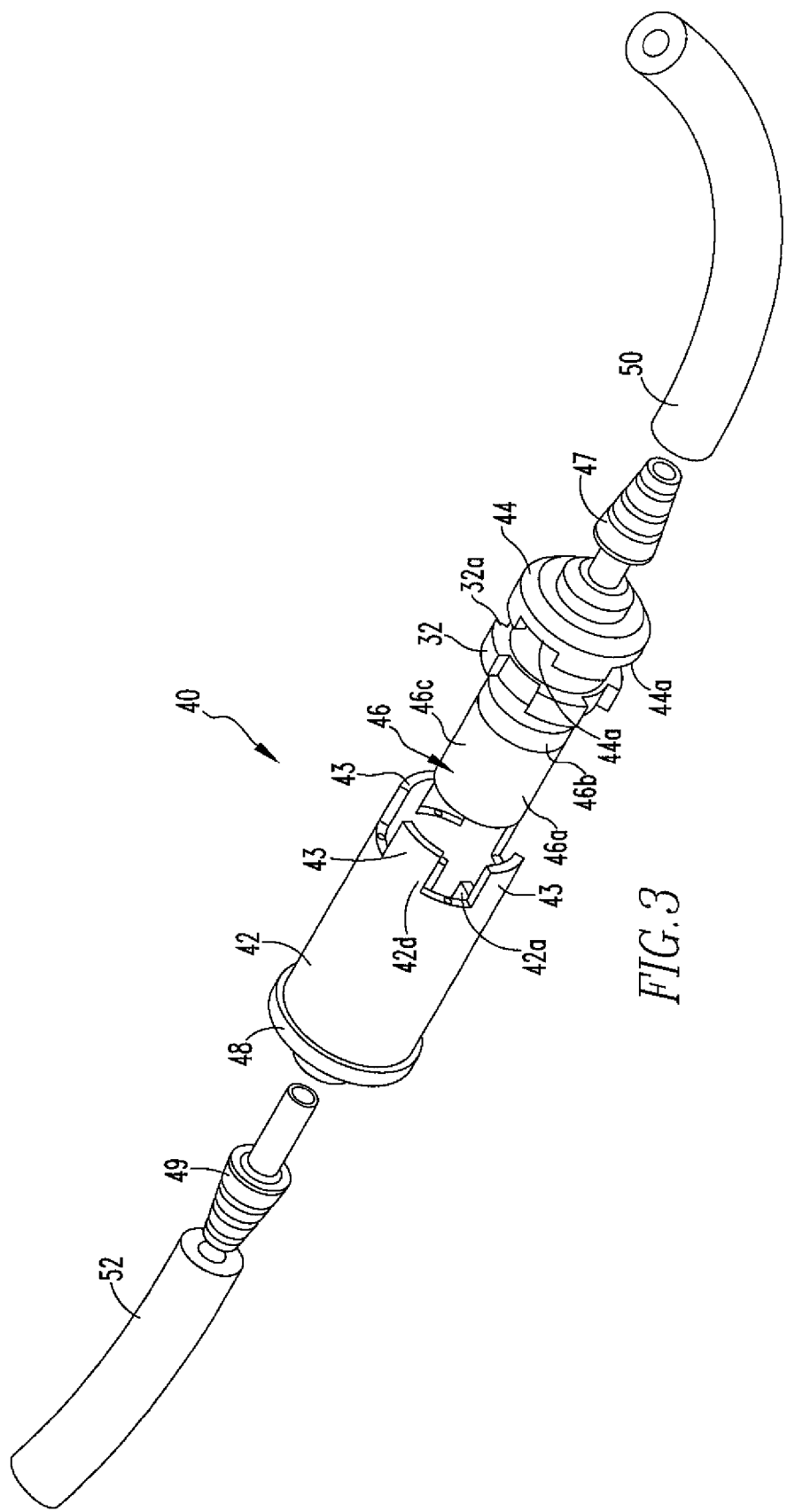
FIG. 3 is an exploded, perspective view of the tissue collection device of FIG. 2.

Referring to FIGS. 2 and 3, the tissue collection device 40 includes a substantially cylindrical housing 42, an inlet connector 44, a biodegradable, fluid permeable, implant material, or tissue scaffold 46, and an outlet cap 48. Rather than using a separate filter 30 disposed along the tubing 50, in this implementation, a filter 32 is disposed directly within the housing 42.

The housing 42 includes a plurality of longitudinally extending and radially-projecting ribs 42a formed about an internal surface 42b of the housing 42. The ribs 42a receive and releasably hold the tissue scaffold 46 within an interior 42c of the housing 42 until tissue scaffold 46 is removed from the housing 42, as discussed below. The ribs 42a are dimensioned such that there is about 0.5 mm spacing between the inner surface of the housing 42 and the outer surface 46c of the tissue scaffold 46 to allow for flow of the cut tissue and surgical fluid into the tissue collection device 40 so that the cut tissue may enter radially through the sides of the tissue scaffold 46 to load the tissue scaffold 46. The housing 42 also includes a plurality of flanges 43 formed about a periphery of an end 42d of the housing 42. The flanges 43 engage corresponding cutout portions 32a of the filter 32 and cutout portions 44a of the inlet connector 44. When the flanges 43 are brought into engagement with the portions 32a and 44a to form the tissue collection device 40, there exists a spacing or gap D (FIG. 2) between the filter 32 and the inlet connector 44 of between about 30 mm and 40 mm. Such spacing allows for effective removal of particles that are too large to efficiently load tissue scaffold 46.

The tissue scaffold 46 includes a first structure/material 46a forming a first region of the tissue scaffold bonded to a second structure/material 46b forming a second region of the tissue scaffold. The structure/material 46a has dissimilar mechanical and porosity properties from that of material 46b. Exemplary tissue scaffolds 46 that can be employed with the implementations discussed herein are described in U.S. Pat. Nos. 6,013,853, 5,876,452, and 5,607,474, which are incorporated herein by reference in their entireties. Another exemplary tissue scaffold 46 for use with the present implementations is the TruFit® BGS Plug, available from Smith & Nephew, Inc. of San Antonio, Tex.

Two tubing connectors 47, 49 are coupled to the inlet connector 44 and the outlet cap 48, respectively. The tubing connector 47 couples the tubing 50 to the collection device 40. The tubing connector 49 couples a tubing 52 to the collection device 40 and to a source of vacuum 70 (FIG. 1), such as a vacuum pump or other suitable apparatus for providing aspiration during the surgical procedure. In addition, a collection apparatus (not shown) can be coupled to the tissue collection device 40 via the tubing 52 to collect tissue and fluid that passes through the tissue collection device 40.

Figure 4:
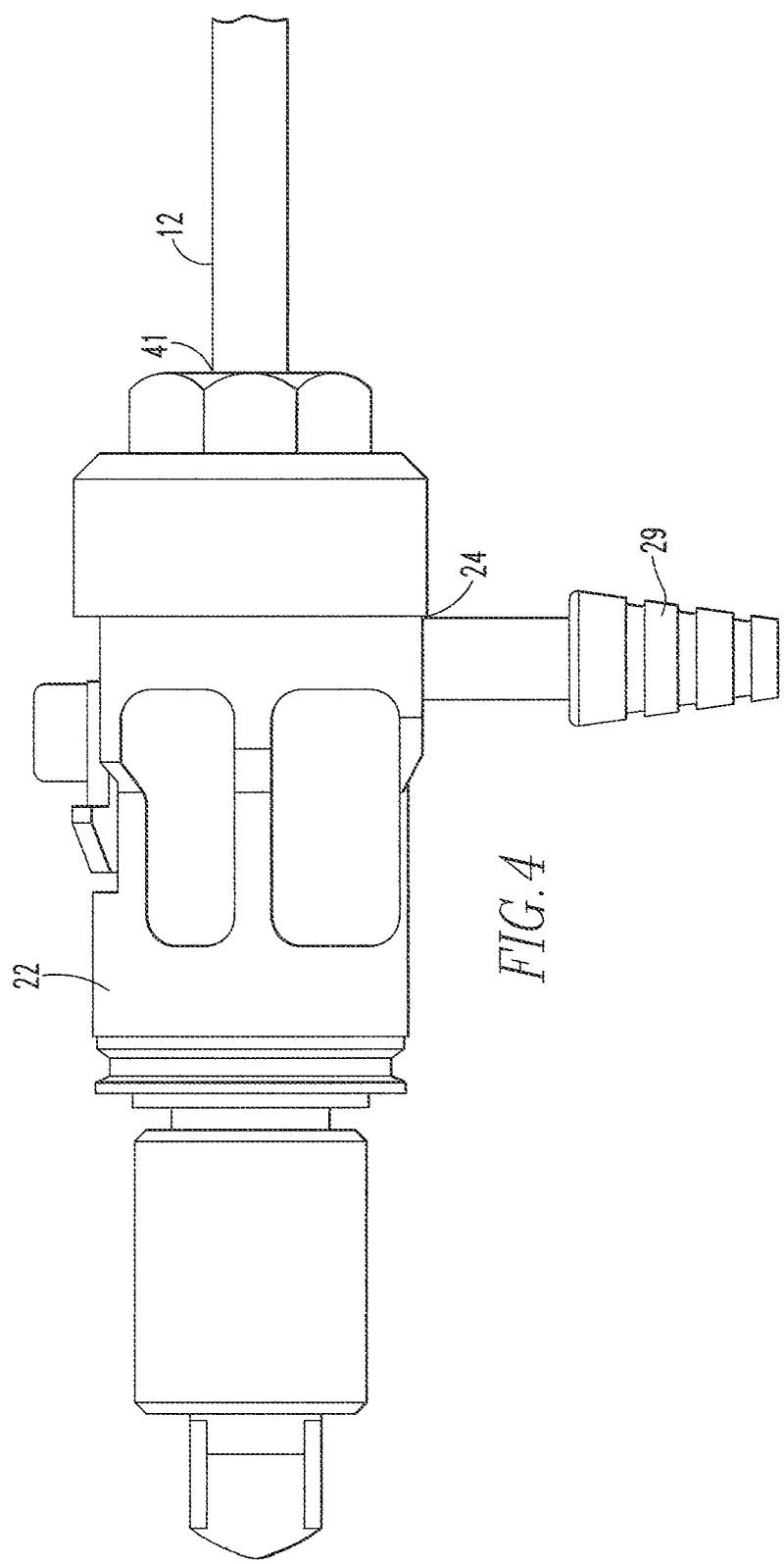
FIG. 4 is a side perspective view of surgical blade hub of the assembly of FIG. 1.
Figure 5:
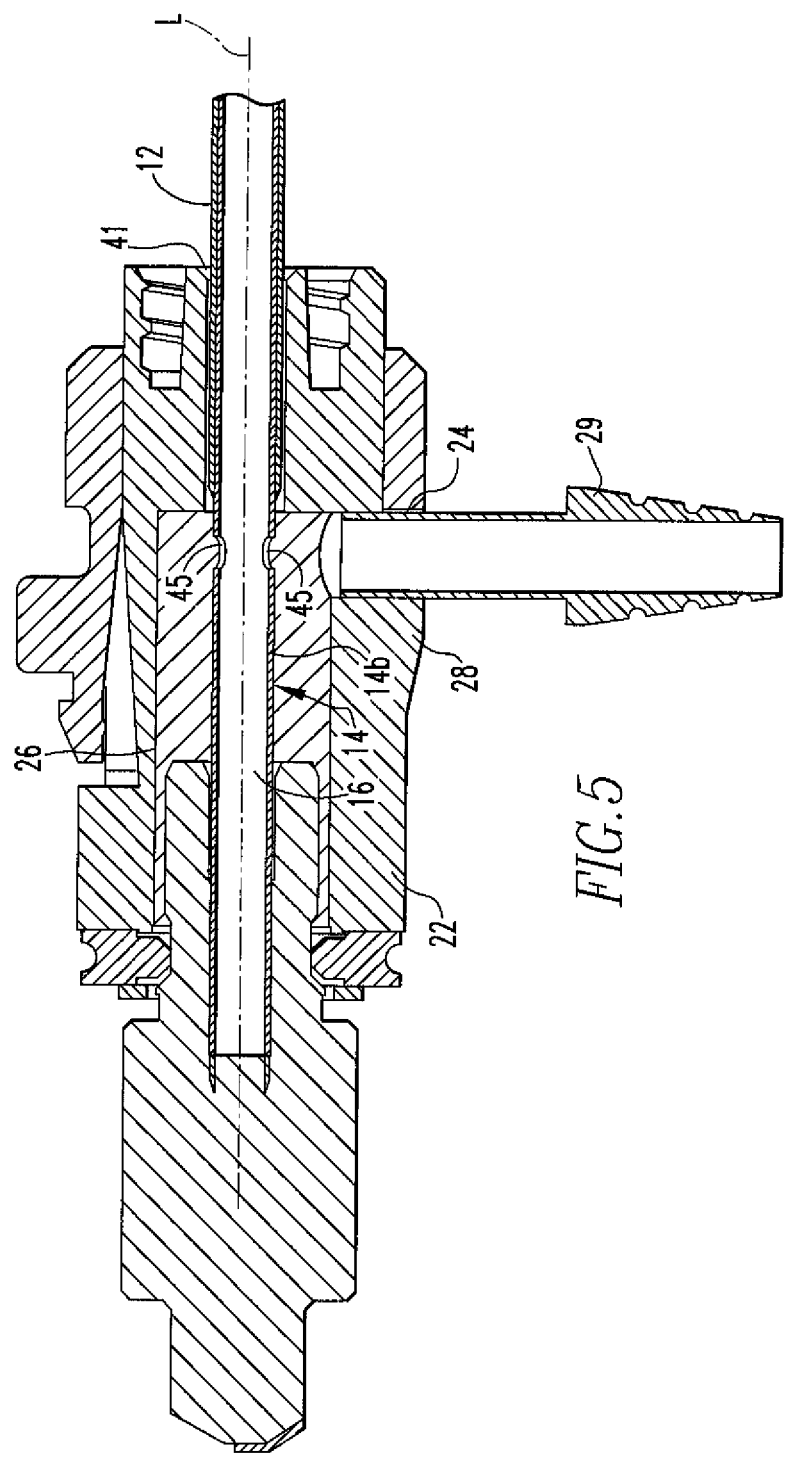
FIG. 5 is a cross-section view of the hub of FIG. 4.
Figure 6:
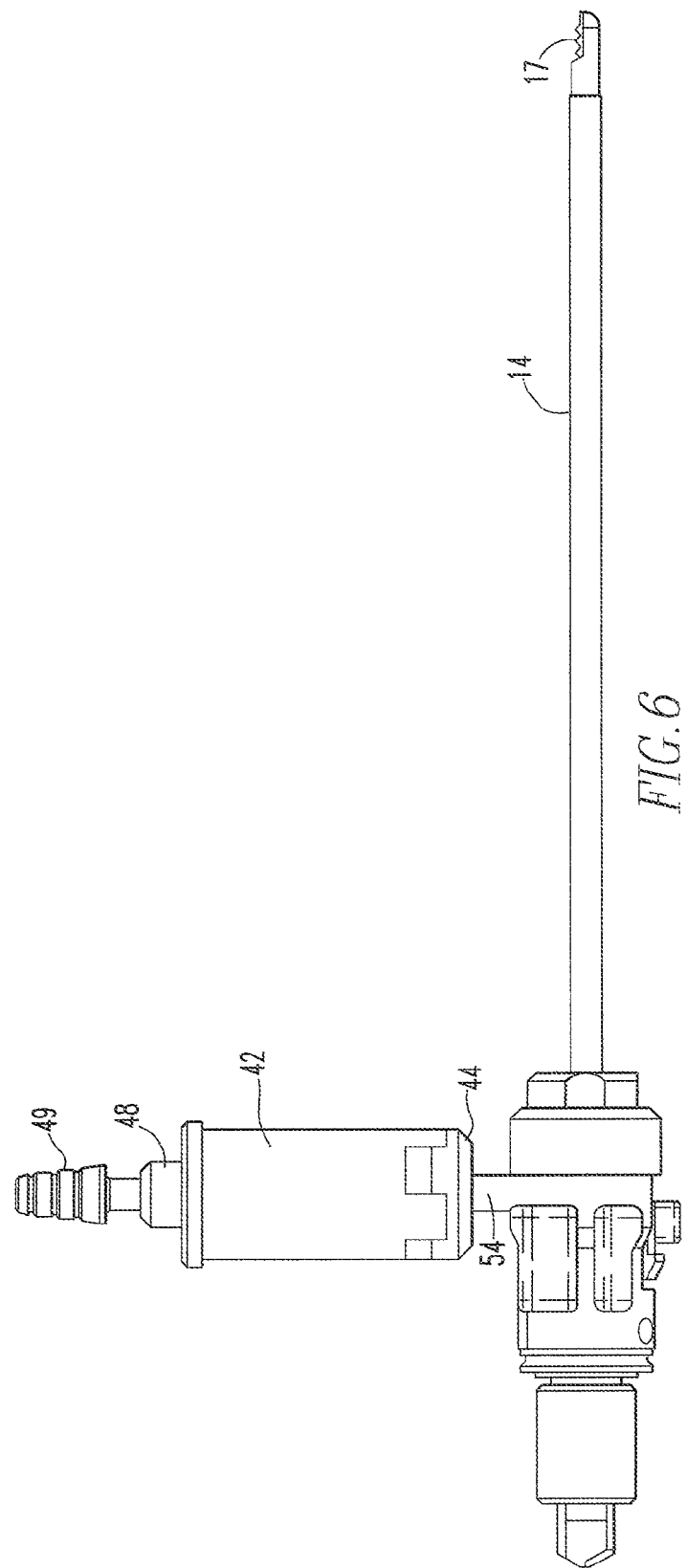
FIG. 6 is a side perspective view of an alternative tissue harvesting assembly.

Referring to FIGS. 4 and 5, the hub 22 (FIG. 1) of the surgical blade 10 is coupled to the outer tubular member 12 via an opening 41 formed in the hub 22. The inner tubular member 14 is rotatably received within the outer tubular member 12 and defines the aspiration lumen 16 extending longitudinally through the inner tubular member 14. The inner tubular member 14 further defines one or more openings 45 formed through a side wall 14b of the member 14 within the hub region of the blade 10, which are in fluid communication with the aspiration lumen 16 and a chamber 26 defined within hub 22. Hub 22 further includes a side port 24 formed through a side wall 28 of hub 22 and in fluid communication with the chamber 26. The side port 24 extends in a direction substantially transverse to the longitudinal axis L of the inner tubular member 14. Coupled to the side port 24 is a tubing connector 29. The side port 24 provides a pathway for fluid and cut tissue to flow from the surgical blade 10 to the tissue collection device 40.

Referring to FIGS. 6 and 7, rather than coupling the tissue collection device 40 to the surgical blade 10 via the tubing 50, the tissue collection device 40 can be directly attached to the surgical blade 10 at the side port 24 via an extension 54. The extension 54 can be removably or permanently coupled to the side port 24 of the hub 22. As illustrated in FIGS. 6 and 7, extension 54 is in fluid communication with chamber 26 and provides a pathway for cut tissue and surgical fluid to flow from the surgical blade 10 to the tissue collection device 40. Specifically, cut tissue and surgical fluid flows through the aspiration lumen 16 and through opening 45a of the inner tubular member 14. The opening 45a defined in the side wall 14b of the inner tubular member 14 is sized to enable fragments of cut tissue that are within a size range that efficiently loads onto the tissue scaffold 46 to pass through opening 45a. The edges 14c, 14d of side wall 14b that form the opening 45a can further cut the tissue passing through opening 45a to further reduce the size of the tissue fragments passing through the opening 45a.

In operation, the surgical blade 10 is brought into contact with a desired bodily tissue, such as synovial or adipose tissue (FIG. 1). The operator cuts a desired amount of tissue from the donor site using the blade 10. The vacuum source 70 aspirates fluid and the cut tissue through the aspiration lumen 16 of the inner tubular member 14 to the tissue collection device 40. The filter removes undesirable cut tissue from the fluid pathway, such as particles larger than, for example, about 300 µm to about 600 µm. The cut tissue and fluid then flow around and through the tissue scaffold 46 loading the scaffold with cut tissue for later implantation into the site to be treated. Any excess cut tissue and fluid volume pass through the tissue collection device 10 and are aspirated to the collection apparatus, not shown.

Figure 9A:
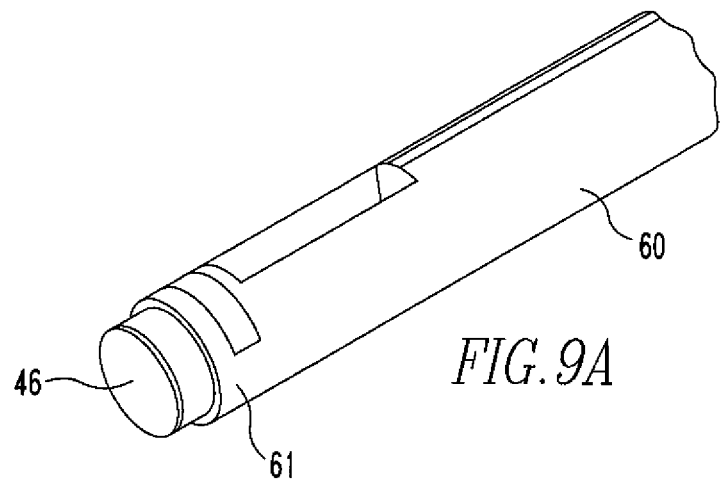
FIGS. 9A-9B illustrate delivery and implementation of the tissue scaffold of FIG. 8.
Figure 9B:
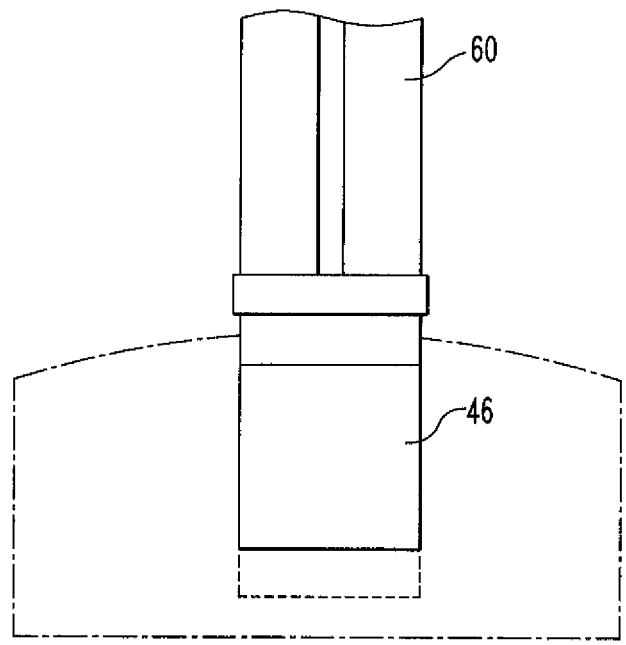

Referring to FIGS. 8 and 9A-9B, to remove the tissue scaffold 46 from the tissue collective device housing 42, the operator removes the outlet cap 48 from the housing 42, thereby exposing one end of tissue scaffold 46. The operator then contacts the exterior periphery of tissue scaffold 46 with a tissue scaffold delivery device 60, such as the TruFit® Delivery Device available from Smith & Nephew, Inc. of San Antonio, Tex. Once the tissue scaffold 46 is received by a distal end 61 of the tissue scaffold delivery device 60 (FIG. 9A), the operator implants the tissue scaffold 46 at the desired location as shown in FIG. 9B. Other implementations of delivering the tissue scaffold 46 to the desired location are described in U.S. Pat. No. 6,013,853.

Figure 10:
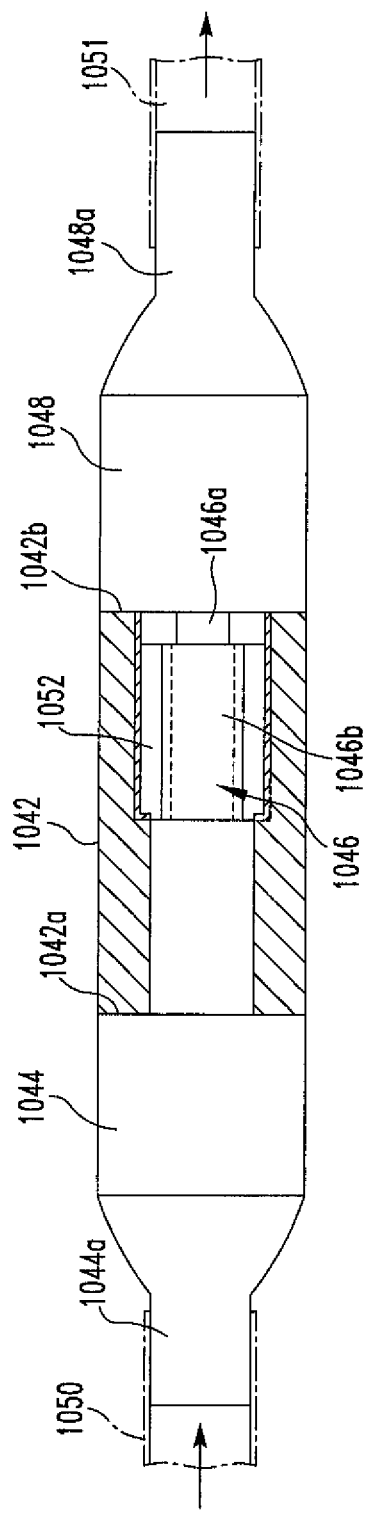
FIG. 10 is a side perspective view of an alternative tissue collection device.

An alternative implementation of a tissue collection device 1040 (FIG. 10) for use with the tissue harvesting assembly 100 includes a cylindrical transparent housing 1042 having a first end 1042a and a second end 1042b, a biodegradable, fluid permeable, implant material, or tissue scaffold 1046, and a sleeve 1052 surrounding a portion, for example, the circumference but not ends, of the tissue scaffold 1046 and disposed between the tissue scaffold 1046 and the housing 1042. The housing 1042 and the sleeve 1052 can be made from plastic or any other suitable material. An inlet connector 1044 and an outlet connector 1048 are removably coupled to the first and second ends 1042a, 1042b, respectively, of the housing 1042, using, for example, mating threaded connections (not shown) on the inlet connector 1044, and the outlet connector 1048 and the housing 1042, adhesive, an interference friction fit between the ends of the housing 1042 and corresponding receiving portions (not shown) formed in the inlet connector 1044 and the outlet connector 1048, or other suitable methods. The connectors 1044, 1048 form a fluid-tight seal with the housing 1042. The inlet connector 1044 includes a tubing connector portion 1044a that couples the tissue collection device 1040 to the blade 10 (FIG. 1) via a flexible tubing 1050. The flexible tubing 1050 is coupled to a filter, such as the filter 30 shown in FIG. 1, which is positioned between the blade 10 and the tissue collection device 1040 such that the filter 30 is in fluid communication with the blade 10. The outlet connector 1048 includes a tubing connector 1048a that couples the tissue collection device 1040 to a tubing 1051 and to a source of vacuum 70 (FIG. 1). Fluid and cut tissue are aspirated through the tissue collection device 1040 to load the tissue scaffold 1046 with cut tissue as explained in more detail below.

Figure 11:
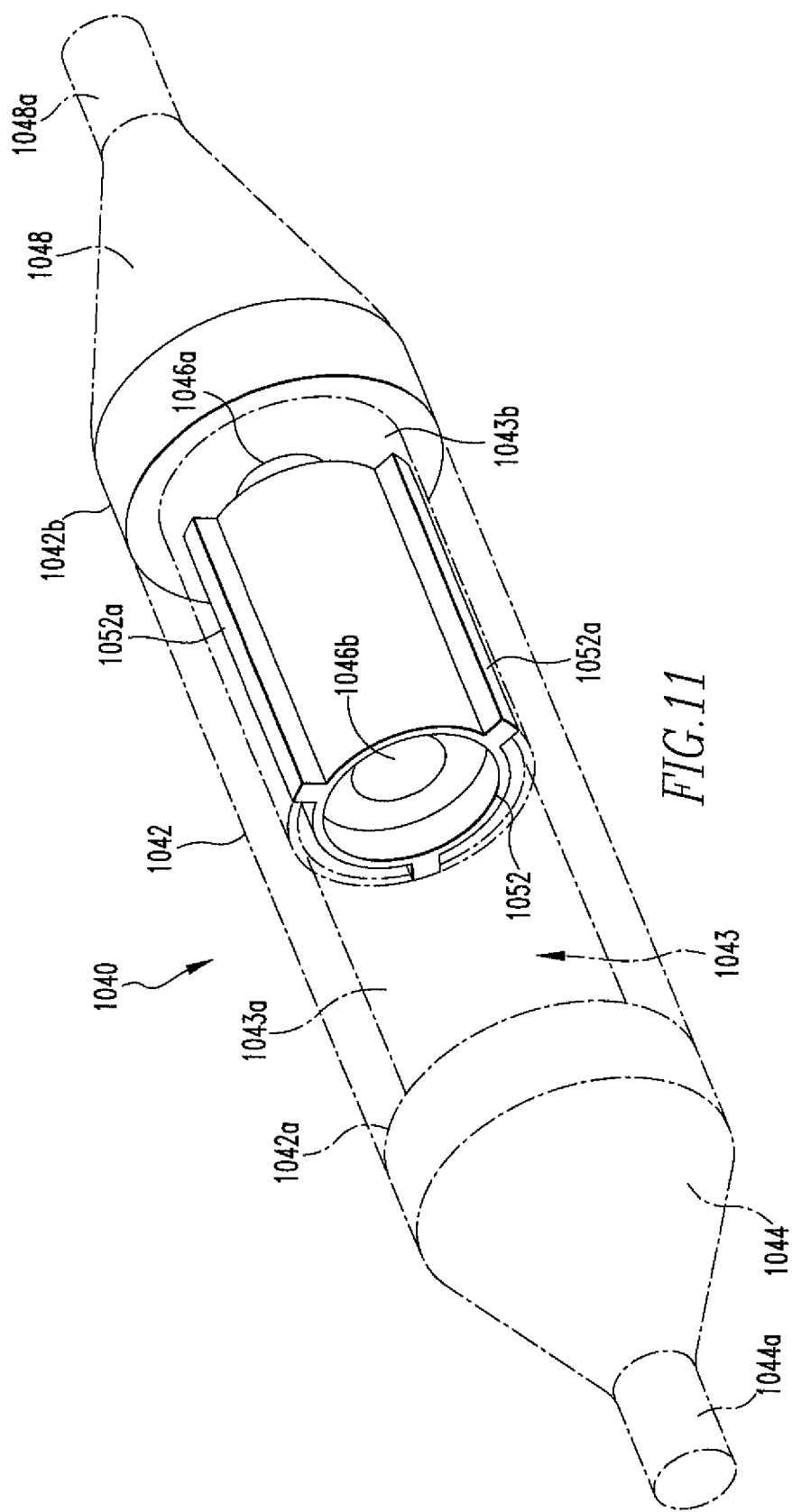
FIG. 11 is a perspective view of the alternative tissue collection device of FIG. 10.
Figure 12:
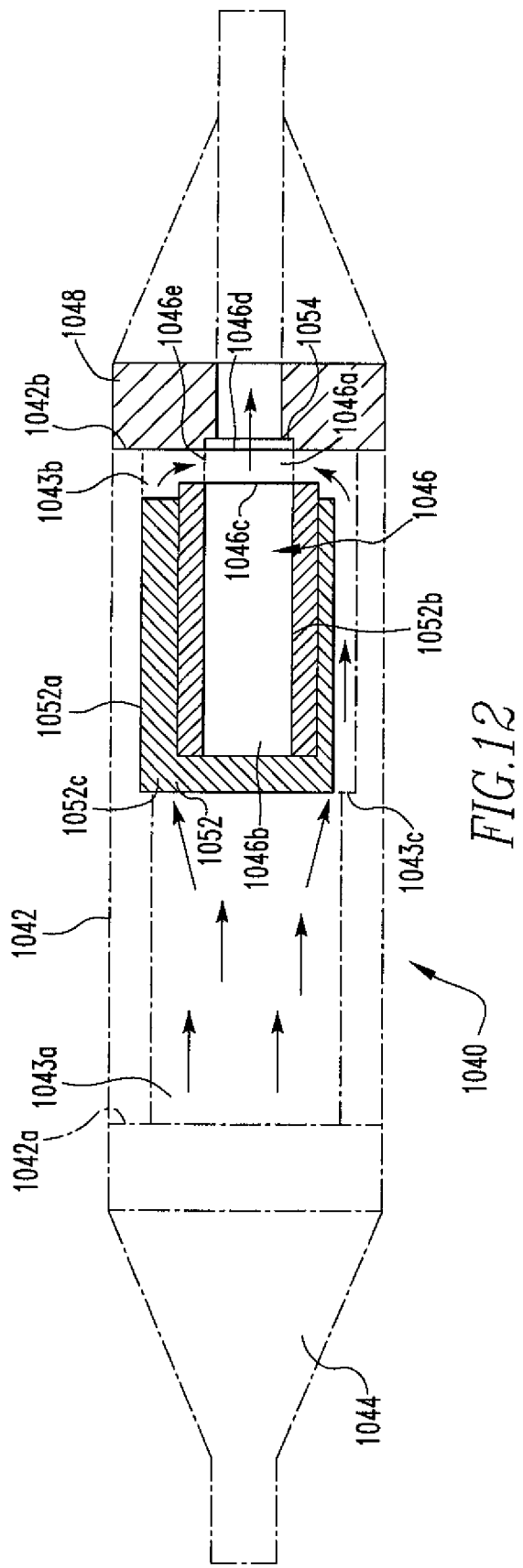
FIG. 12 is a cross-section view of the tissue collective device of FIG. 11.

Referring to FIGS. 11, 12, and 15, the housing 1042 defines an interior 1043 including a first portion 1043a having a diameter Da and a second portion 1043b having a diameter Db, which is larger than diameter Da. The first portion 1043a and the second portion 1043b intersect approximately midway along a length of the housing 1042 to form a step or intersection 1043c. The sleeve 1052 (FIGS. 11, 12, and 13) includes a set of projecting ribs 1052a disposed about the periphery of the sleeve 1052. The ribs 1052a are configured to permit the sleeve 1052 to be inserted into the second portion 1043b of the housing 1042 and to be releasably held by the second portion 1043b by, for example, a friction fit between the wall of the housing 1042 and the ribs 1052a. As shown in FIG. 12, the sleeve 1052 slides into the second portion 1043b until an end 1052c of the ribs 1052a abuts the intersection 1043c of the first portion 1043a and the second portion 1043b. The sleeve 1052 further defines an opening 1052b dimensioned to receive the tissue scaffold 1046 as shown in FIGS. 11 and 12.

The tissue scaffold 1046 (FIG. 14) includes a first region or material 1046a bonded (e.g., with adhesive) to a second region or material 1046b at an intersection 1046c. The first region 1046a defines a circular face 1046d and includes a side portion 1046e. The regions 1046a, 1046b have dissimilar mechanical and porosity properties as more fully described in U.S. Pat. Nos. 6,013,853, 5,876,452, and 5,607,474. The tissue scaffold 1046 is longer than the opening 1052b of the sleeve 1052 such that when the tissue scaffold 1046 is inserted into the opening 1052b, the first region 1046a protrudes from the sleeve 1052. The opening 1052b of the sleeve 1052 releasably holds the second region 1046b of the tissue scaffold 1046 via, for example, a frictional fit between the second region 1046b and the mating surfaces of the opening 1052b. As further illustrated in FIG. 12, one or more seals, such as o-ring 1054 placed between the outlet connector 1048 and the housing 1042, and/or the tissue scaffold 1046, provides a fluid-tight seal of the tissue collection device 1040.

In operation, the surgical blade 10 (FIG. 1) is brought into contact with a desired bodily tissue, such as adipose or synovial tissue. The operator cuts a desired amount of tissue from the donor site using the blade 10. The vacuum source 70 (FIG. 1) aspirates the fluid and the cut tissue through the filter, which removes cut tissue that is larger than the opening size of the filter, from the fluid pathway, and to the tissue collection device 1040. The cut tissue and fluid enter the interior 1043 of the housing 1042 via the inlet connector 1044. The cut tissue and fluid flow over and around the exterior of the sleeve 1052 and enter the side 1046e of the first region 1046a of the tissue scaffold 1046 (as depicted by the arrows in FIG. 12). Because the sleeve 1052 completely surrounds the exterior of the second region 1046b of the tissue scaffold 1046, and because the bonding agent (e.g., adhesive) between the first region 1046a and the second region 1046b of the tissue scaffold 1046 minimizes flow of tissue and fluid therethrough, the cut tissue and fluid flows through the first region 1046a of the tissue scaffold 1046. In particular, the tissue and fluid flow through the side 1046e of the first region 1046a and out of the circular face 1046d (FIG. 12, 14), thereby loading only the first region 1046a, including the interior and exterior of the first region 1046a, with cut tissue for later implantation into the desired site to be treated. By flowing cut tissue through the side 1046e of the first region 1046a and out of the circular face 1046d, collection of excess debris on the circular face 1046d is also minimized. Any excess debris may act as an abrasive possibly causing further damage to the cartilage. In addition, there is a small amount of clearance between the plug and the tissue, therefore any excess debris on the plug may cause problems with inserting it into a cartilage defect. Any excess cut tissue and fluid pass through the outlet connector 1048 and are aspirated to a collection apparatus, not shown.

Referring to FIGS. 16A-16K, an exemplary tissue scaffold 1046 is shown that includes a first region 1046a that includes one or more fluid-flow pathways 1047b formed through the side 1046e and one or more fluid-flow pathways 1047a formed through the face 1046d of the first region 1046a by passing a needle or other suitable device through the first region 1046a. The fluid-flow pathways 1047a, 1047b cooperate to provide for an increased flow rate through the first region 1046a of the tissue scaffold 1046. The first region 1046a includes a cut out portion 1048 (FIG. 16E), which is sized to receive a mating protrusion 1080 of the second region 1046b of the tissue scaffold 1046 in a sliding frictional fit.

Figure 16A:
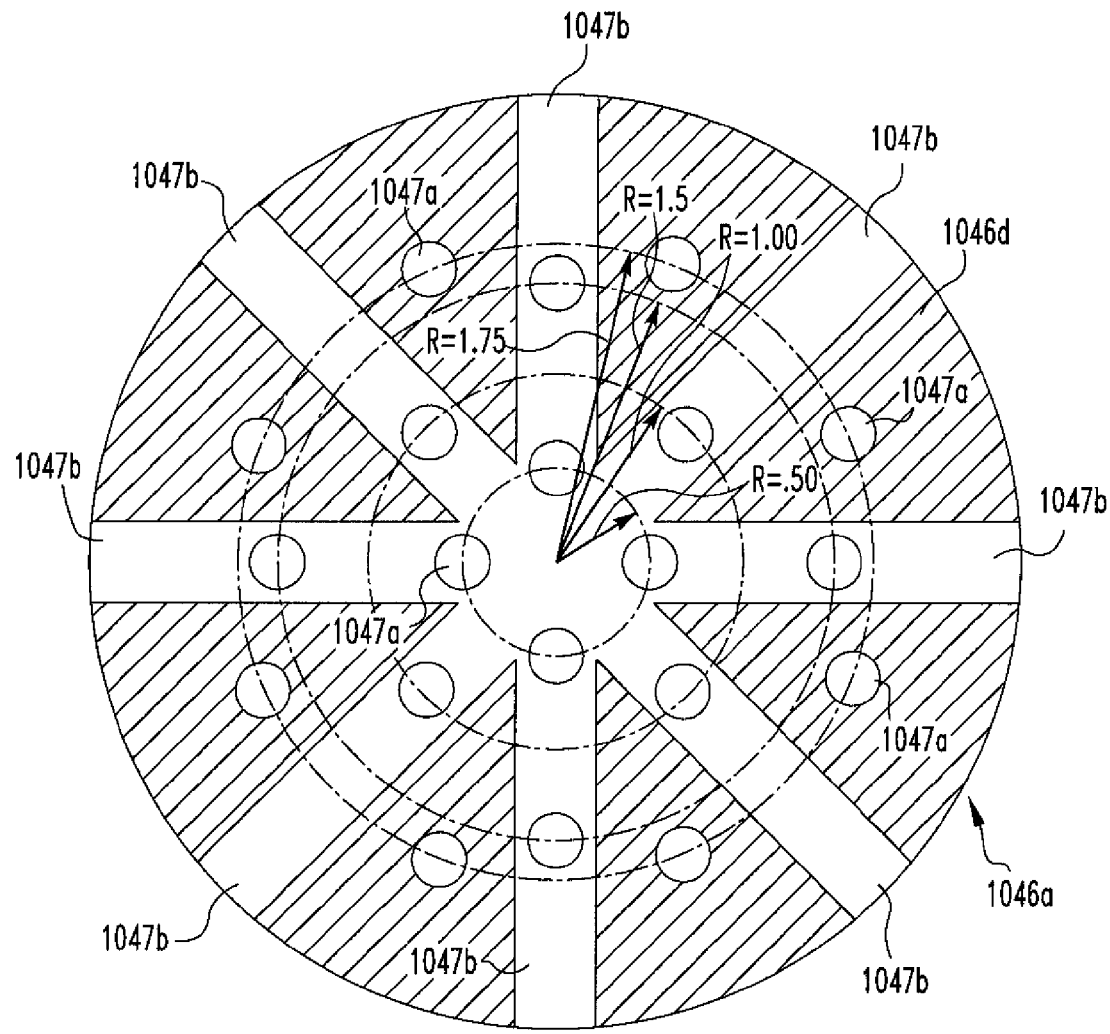
FIG. 16A is a front end view of an alternative implementation of the first region of the tissue scaffold of FIG. 14.

The first region 1046 also includes one or more fluid flow pathways 1047a (FIGS. 16A-16K), for example, twenty fluid flow pathways 1047a (FIG. 16A), by passing a needle through the face 1046d of the first region 1046a at desired locations (FIG. 16A). Other methods of making the pathways, known to one of skill in the art, may also be used. As shown in FIGS. 16E, 16G, 16I, and 16K, the fluid flow pathways 1047a extend approximately halfway through the first region 1046a from the face 1046d, and have a length of about 10 mm. The fluid flow pathways 1047a have a cross-sectional diameter of about 300 µm.

Figure 16C:
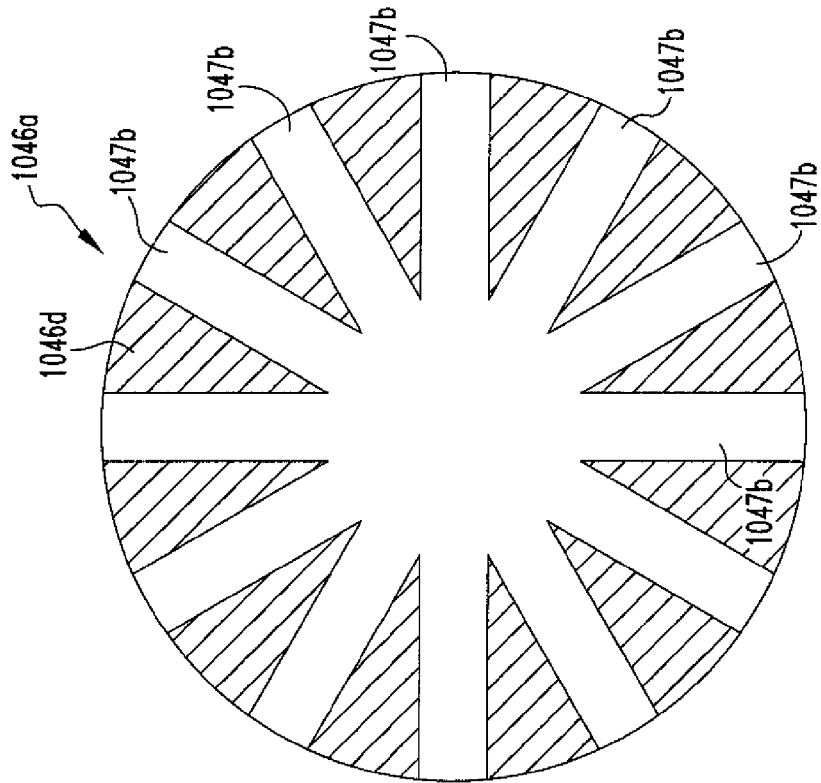
FIG. 16C is a front end view of an alternative implementation of the first region of the tissue scaffold of FIG. 14.
Figure 16B:
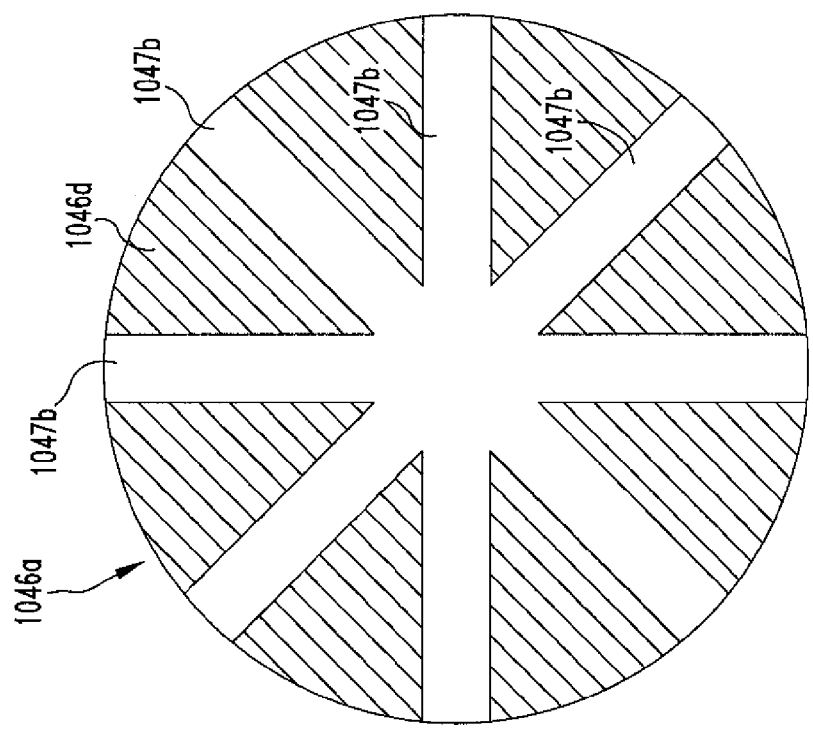
FIG. 16B is a front end view of an alternative implementation of the first region of the tissue scaffold of FIG. 14.

FIGS. 16A-16K illustrate a number of possible configurations for forming the fluid flow pathways 1047b through the side 1046e of the first region 1046a. For example, as shown in FIGS. 16B and 16C, the first region 1046a includes four and six fluid flow pathways 1047b, respectively, formed through the first region 1046a. The fluid flow pathways 1047b extend across the full diameter of the first region 1046a and form eight (FIG. 16B) and twelve (FIG. 16C) apertures 1049 around the periphery of the side 1046e. The apertures 1049 provide entry points for the cut tissue to flow into the interior of the first region 1046a.

Figure 16E:
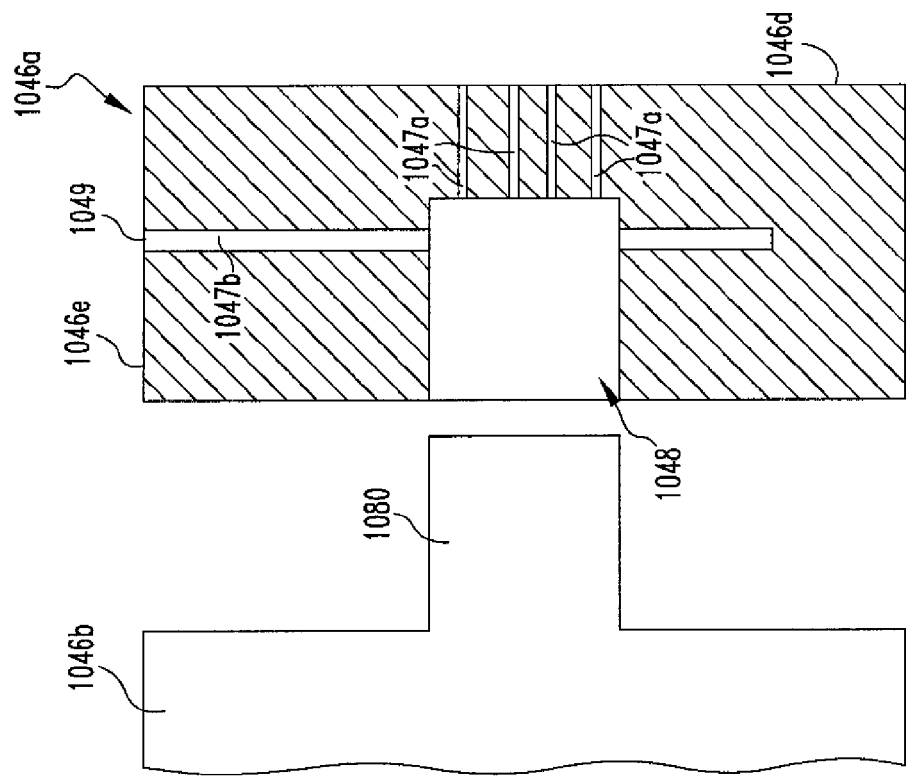
FIG. 16E is a cross-section view of the first region of the tissue scaffold of FIG. 16D.
Figure 16D:
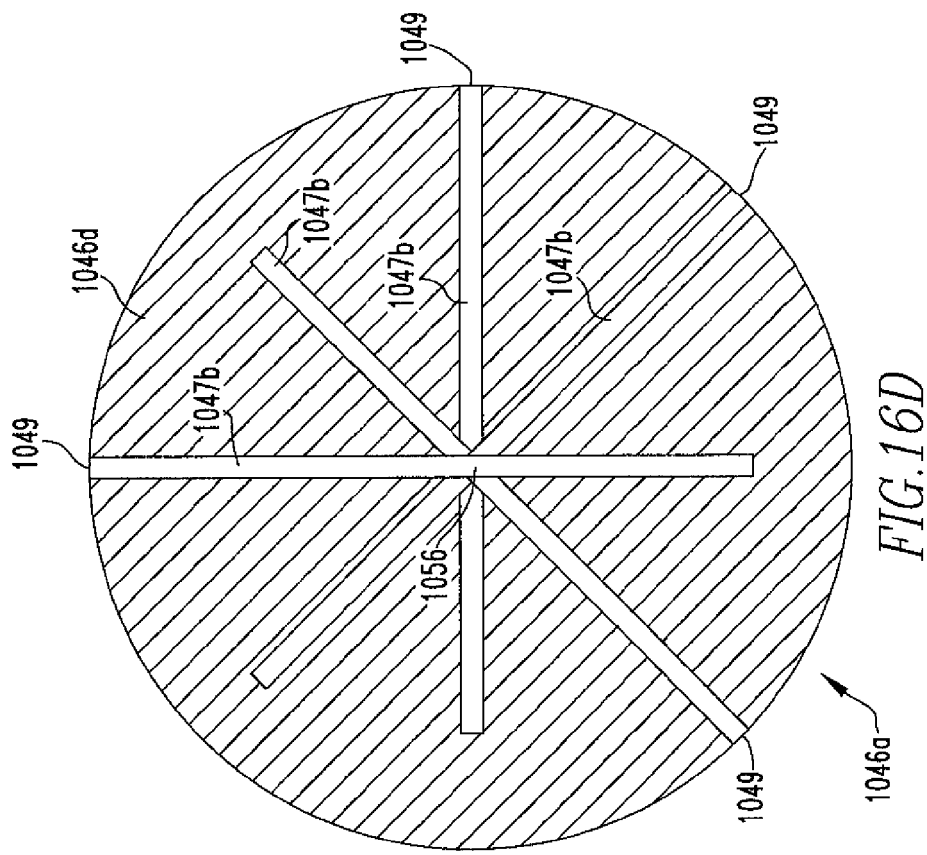
FIG. 16D is a front end view of an alternative implementation of the first region of the tissue scaffold of FIG. 14.
Figure 16G:
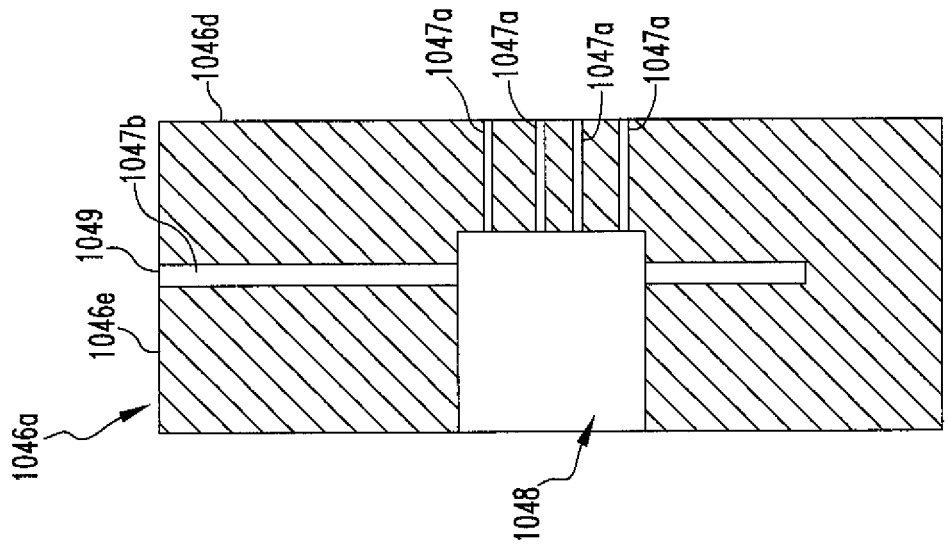
FIG. 16G is a cross-section view of the first region of the tissue scaffold of FIG. 16F.
Figure 16F:
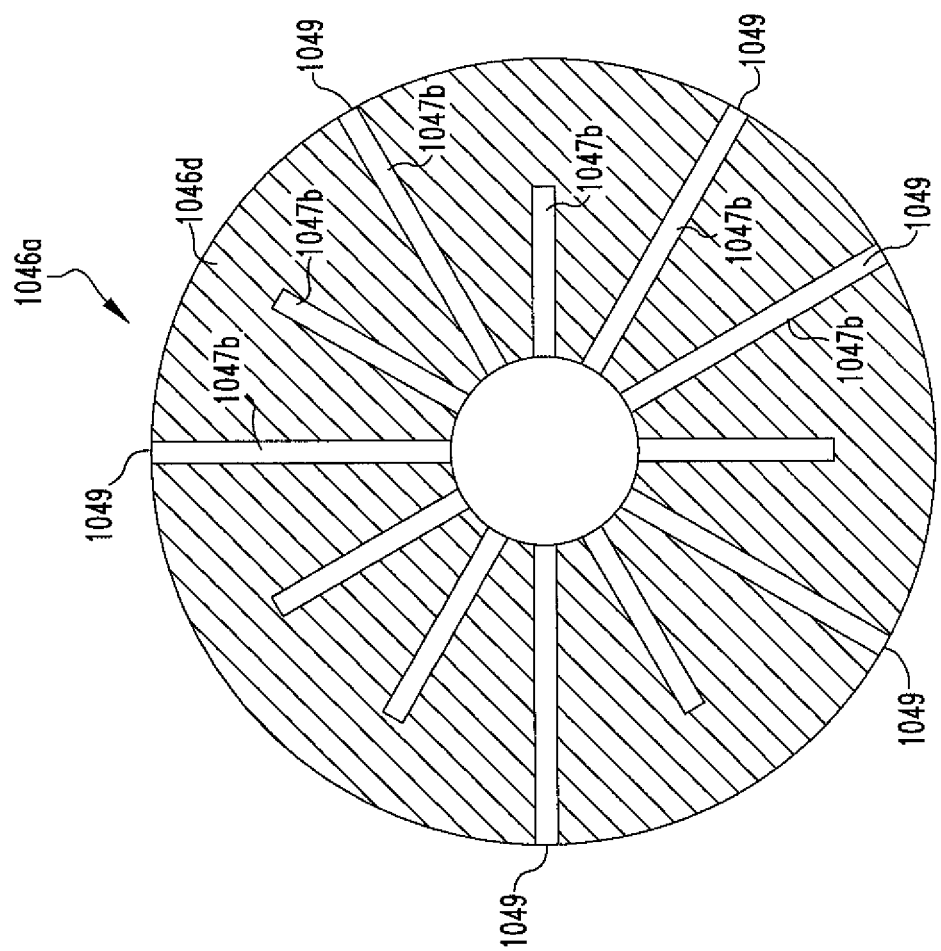
FIG. 16F is a front end view of an alternative implementation of the first region of the tissue scaffold of FIG. 14.

FIGS. 16D-16E illustrate four fluid flow pathways 1047b formed through the side 1046e of the first region 1046a. The fluid flow pathways 1047b do not extend across the full diameter of the first region 1046a. Thus, only four apertures 1049 are formed in the side 1046e. As illustrated in FIG. 16E, the fluid flow pathways 1047b are formed at approximately the mid-point of the side 1046e of the first region 1046a, and intersect at a point 1056 near the center of the first region 1046a. FIGS. 16F-16G illustrate a first region 1046a having six fluid-flow pathways 1047b, which do not extend across the full diameter of the first region 1046a, with six apertures 1049 formed in the side 1046e.

Figure 16K:
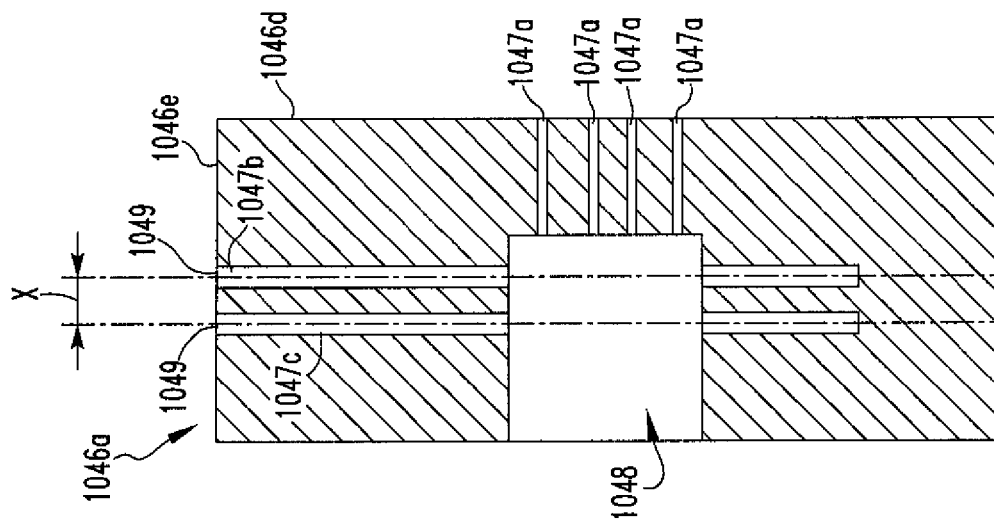
FIG. 16K is a cross-section view of the first region of the tissue scaffold of FIG. 16J.
Figure 16J:
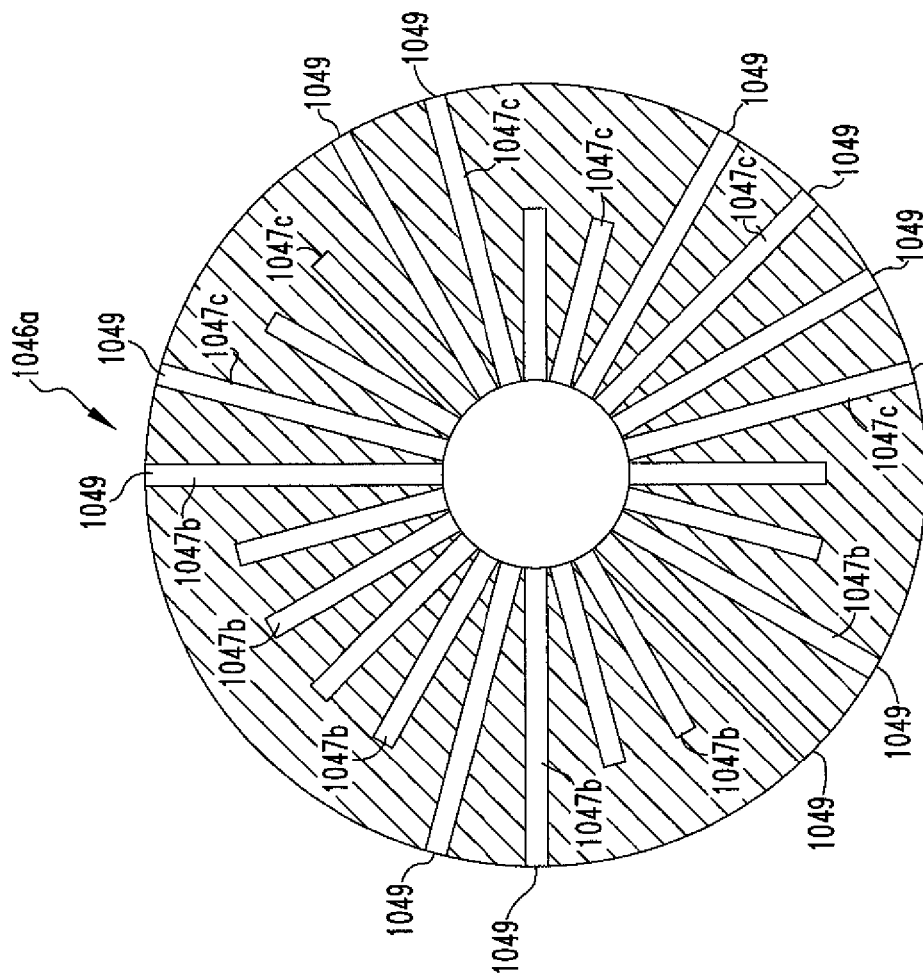
FIG. 16J is a front end view of an alternative implementation of the first region of the tissue scaffold of FIG. 14.

The first region 1046a can include two layers of fluid-flow pathways, 1047b, 1047c (FIGS. 16H-16K), formed through the side 1046e of the first region 1046a and separated by a distance X along the side 1046e. For example, as shown in FIGS. 16H-16I, the first region 1046a includes two layers of four fluid-flow pathways 1047b, 1047c formed through the side 1046e of the first region 1046a and defining eight apertures 1049. FIGS. 16J-16K illustrate a first region 1046a including two layers of six fluid-flow pathways 1047b, 1047c formed through the side 1046e of the first region 1046a and defining 12 apertures 1049 in the side 1046e of the first region 1046a. Employing multiple layers of fluid-flow pathways, 1047b, 1047c in the first region 1046a increases the number of available apertures for the cut tissue to flow into the first region 1046a and also increases the number of pathways available for retaining the cut tissue within the first region 1046a. This results in more efficient loading of the tissue scaffold and provides for a faster overall process time.

In the examples shown in FIGS. 16A-16K, the fluid-flow pathways 1047a have a cross-sectional diameter of about 300 µm, and the fluid-flow pathways 1047b, 1047c have a cross-sectional diameter of about 500 µm. By employing larger entrance fluid-flow pathways 1047b, 1047c, the fluid-flow pathways 1047a, b, c tend to increase the flow rate of the fluid and cut tissue through the interior of the first region 1046a and tend to trap the desired cut tissue within the interior of the first region 1046a, providing for more efficient loading of the tissue onto the tissue scaffold 1046, and specifically, onto the first region 1046a.

Figure 17:
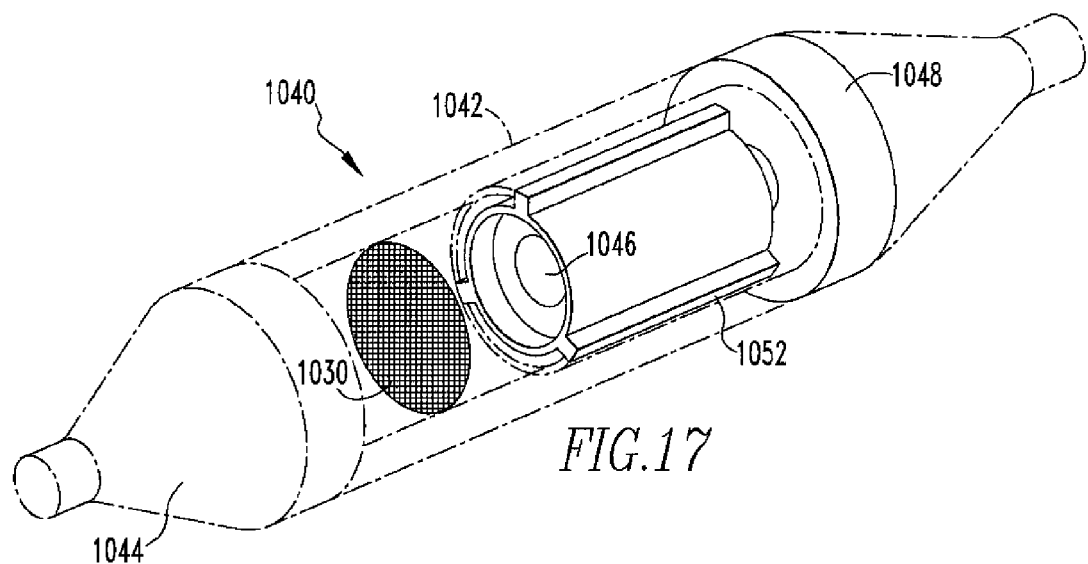
FIG. 17 is a perspective view of an alternative implementation of the tissue collection device of FIG. 11.
Figure 18:
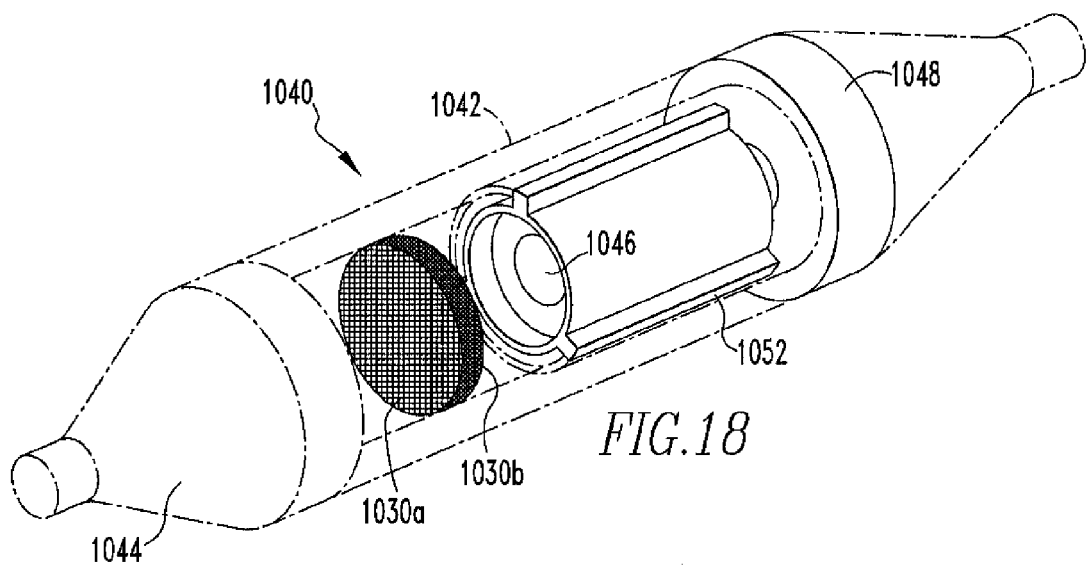
FIG. 18 is a perspective view of an alternative implementation of the tissue collection device of FIG. 11.

FIGS. 17-19 illustrate alternative configurations of the tissue collection device 1040, which, rather than employing a separate filter outside of the housing 1042, such as filter 30 (FIG. 1), employ one or more filters within the housing 1042. In particular, the tissue collection device 1040 of FIG. 17 includes a single filter 1030 disposed within the housing 1042, and the tissue collection device 1040 of FIG. 18 includes a set of filters 1030a, 1030b. When there is a set of filters, the first filter 1030a has a set of openings having an opening size of between about 600 µm to about 3 mm. The second filter 1030b has a set of openings having an opening size of between about 600 µm to about 1 mm. The first filter catches the larger tissue particles first and allows the more moderate size tissue particles to be caught by the second filter. If there is only one filter, the larger tissue particles tend to clog the filter rather quickly. The tissue collection device of FIG. 19 includes a cylindrical filter 1030c disposed within the housing 1042 and surrounding the sleeve 1052 and the tissue scaffold 1046. The cylindrical filter 1030c includes a set of protruding ribs 1031 configured to releasably hold, via, for example, a frictional fit, the filter 1030c within the housing 1042.

Each of the filters 1030, 1030a, 1030b, and 1030c includes openings formed therein with an opening size of up to about 1 mm, and in one particular implementation, between about 600 µm to about 1 mm. Because the total area of the filter is the same for both the single filter configuration of FIG. 17 and the dual-filter configuration of FIG. 18, the diameter of the housing 1042 of the tissue collection device 1040 of FIG. 18 is approximately one half of the diameter of the housing 1042 of the tissue collection device 1040 of FIG. 17. An even smaller housing 1042 may be realized by employing the cylindrical filter 1030c of FIG. 19 because the area of the filter 1030c is relatively large relative to its size. Accordingly, employing multiple filters 1030a, 1030b or a cylindrical filter 1030c allows for a smaller housing 1042, when compared to, for example, a tissue collection device 1040 employing a filter 30 disposed outside of the housing 1042 or a single filter 1030 disposed within the housing 1042 (FIG. 17). Such configurations may be appropriate for certain uses of the tissue collection device 1040, for example, where space is limited. For example, with regards to the implementation shown in FIG. 7, it is preferred that the device be small so as to be less cumbersome to the surgeon and not interfere with his/her ability to perform surgery. Also, with regards to the implementation shown in FIG. 1, the device may be clipped to the drape of the patient during surgery, therefore requiring the device to be smaller so that it does not interfere with other wires, clips, etc., in the surgical area and reducing the possibility of the device from falling off of the patient during movement, for example, of the patient's leg during surgery.

Figure 27:
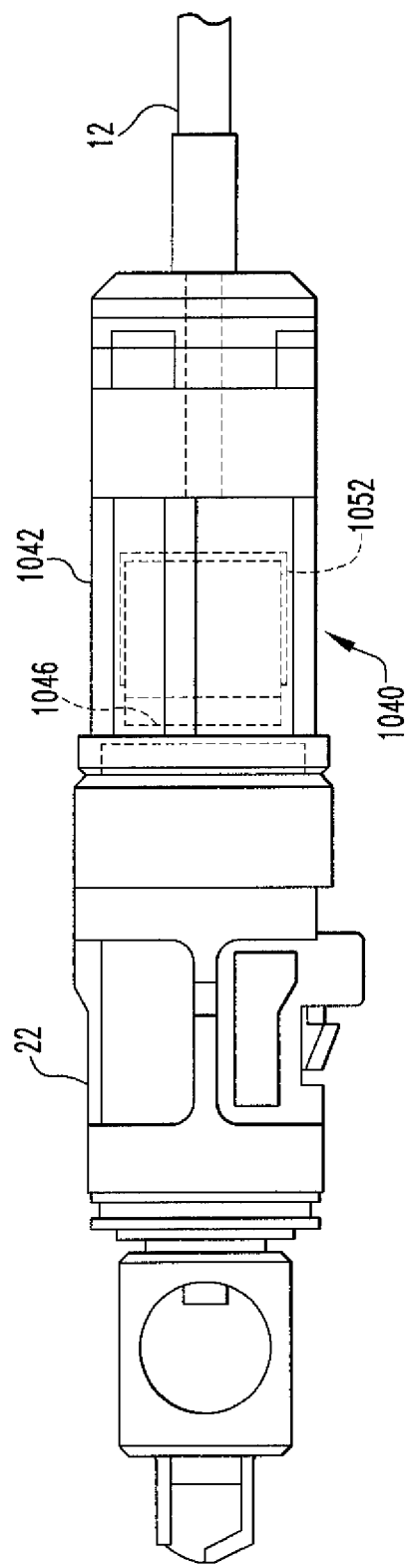
FIG. 27 is a side perspective view of an alternative tissue harvesting assembly.
Figure 28:
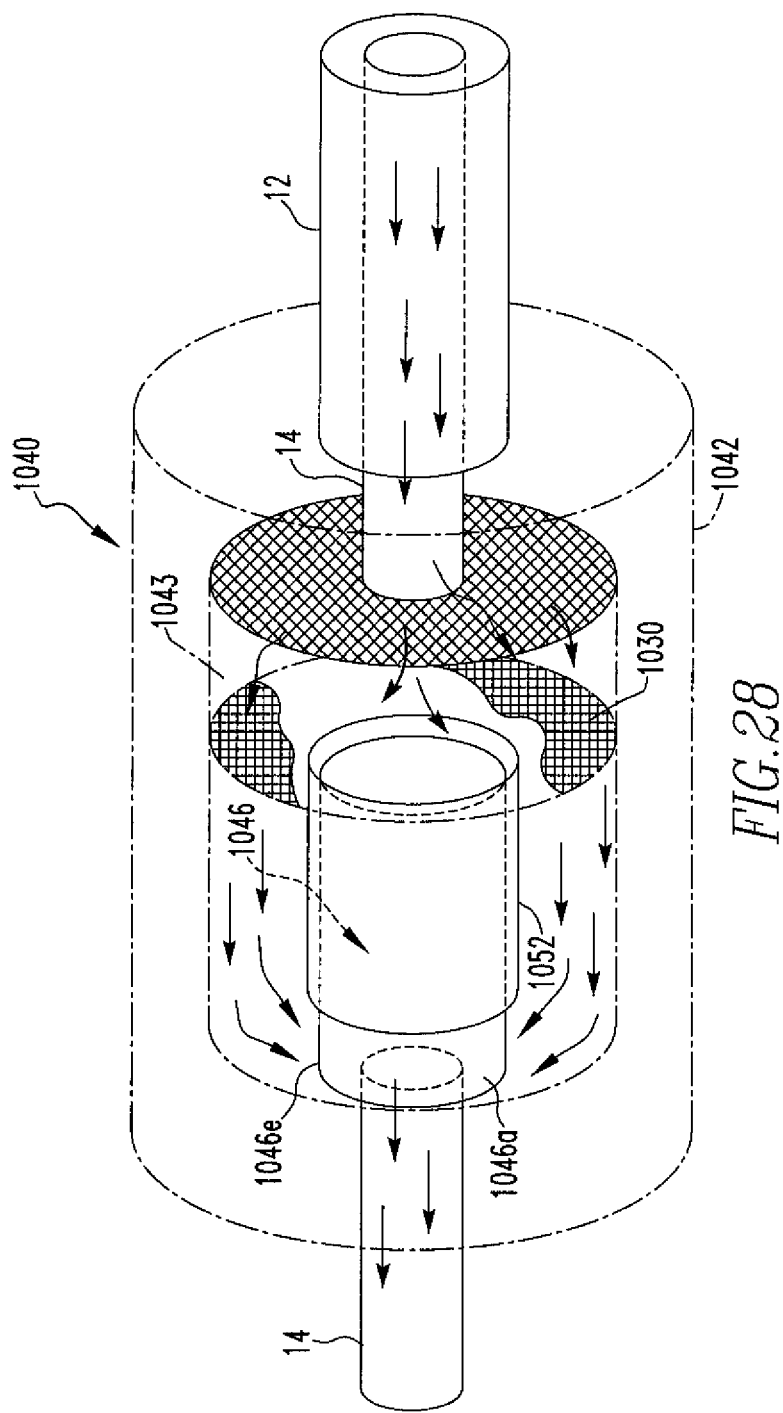
FIG. 28 is a schematic view of the alternative tissue harvesting assembly of FIG. 27.

FIGS. 27 and 28 illustrate an alternative implementation of the tissue collection device 1040 of FIG. 17 having the tissue collection device 1040 attached to a front end 22A of the hub 22. As illustrated in FIG. 28, in this implementation, cut tissue and fluid flow through the inner tubular member 14, as described above, and pass from the inner tubular member 14 and enter the interior 1043 of the housing 1042 (as depicted by the arrows in FIG. 28). The cut tissue and fluid flow through the filter 1030, over and around the exterior of the sleeve 1052, and enter the side 1046e of the first region 1046a of the tissue scaffold 1046 (as depicted by the arrows in FIG. 28). The cut tissue and fluid then flows through the first region 1046a and out of the circular face 1046d and continues through the inner tubular member 14 where any excess tissue and fluid may be collected as described above.

Referring to FIGS. 10-12 and 9A-9B, to remove the tissue scaffold 1046 from the tissue collection device housing 1042, the operator removes the outlet connector 1048 from the housing 1042 to expose one end of the sleeve 1052 and the first region 1046a of the tissue scaffold 1046. The operator slides sleeve 1052 out of the open end of the housing 1042, and contacts the exterior periphery of the first region 1046a of the tissue scaffold 1046 with a tissue scaffold delivery device 60, such as the TruFit® Delivery Device. Once the scaffold 1046 is received within the distal end 61 of the tissue scaffold delivery device 60 (FIG. 9A), the operator implants the tissue scaffold 1046 at the desired location as shown in FIG. 9B.

Figure 20C:
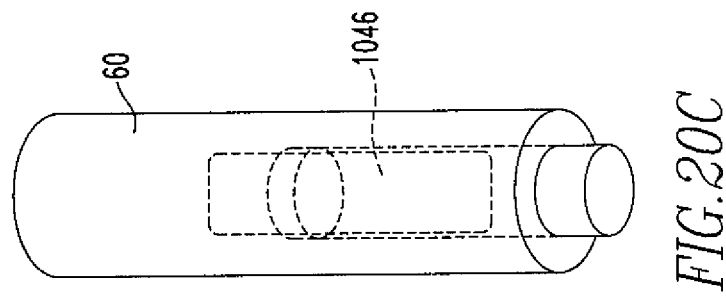
FIGS. 20A-20C illustrate removal of a tissue scaffold from an implementation of the tissue collection device of FIG. 10.
Figure 20B:
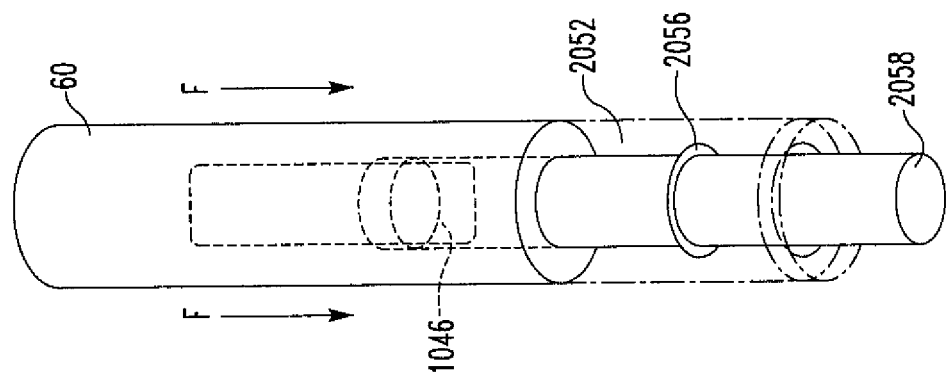
Figure 20A:
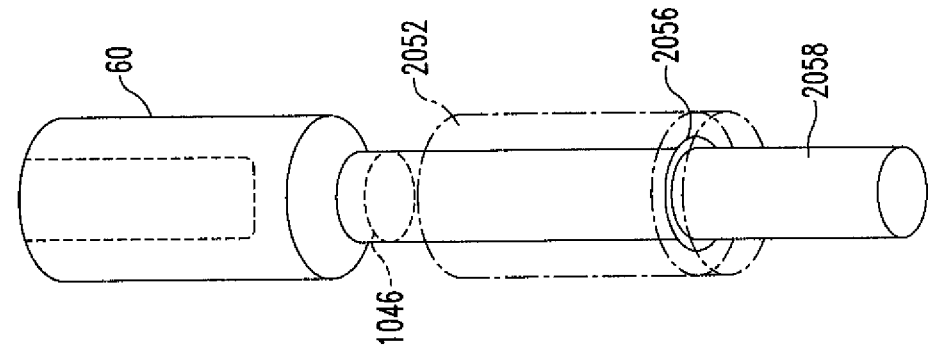

FIGS. 20A-20C illustrate an alternative method of removing the tissue scaffold 1046 from an exemplary sleeve 2052 of the tissue collection device housing 1042. As shown in FIGS. 20A-b, the sleeve 2052 includes a seal or lip 2056 that forms a seal with a shaft 2058. The sleeve 2052 is slidably coupled to the shaft 2058 such that when pressure is applied to the sleeve 2052 by a downward force F applied through the delivery device 60 (FIG. 20B), the shaft 2058 passes through the lip 2056 of the sleeve 2052. As the shaft 2058 passes through the lip 2056, the shaft 2058 pushes the tissue scaffold 1046 out of the opposite end of the sleeve 2052 and into the receiving end of the delivery device 60 (FIG. 20B). As the delivery device 60 is pushed further against the sleeve 2052, the tissue scaffold 1046 is fully received by the delivery device 60 and the operator can then implant the tissue scaffold 1046 at the desired location.

FIGS. 21A-21C illustrate a further alternative method of removing the tissue scaffold 1046 from another exemplary sleeve 2152 of the tissue collection device housing 1042. As illustrated in FIGS. 21A-b, the sleeve 2152 is made from a compliant material, such as rubber, nylon, or other suitable material, and includes a spring 2157. When pressure is applied to the sleeve 2152 by a downward force F applied through the delivery device 60 (FIG. 21B), the sleeve 2152 and the spring 2157 compress downwardly and expose the exterior of the tissue scaffold 1046, which is captured within the delivery device 60 (FIG. 21B-c). The operator can then implant the tissue scaffold 1046 at the desired location.

Figure 22A:
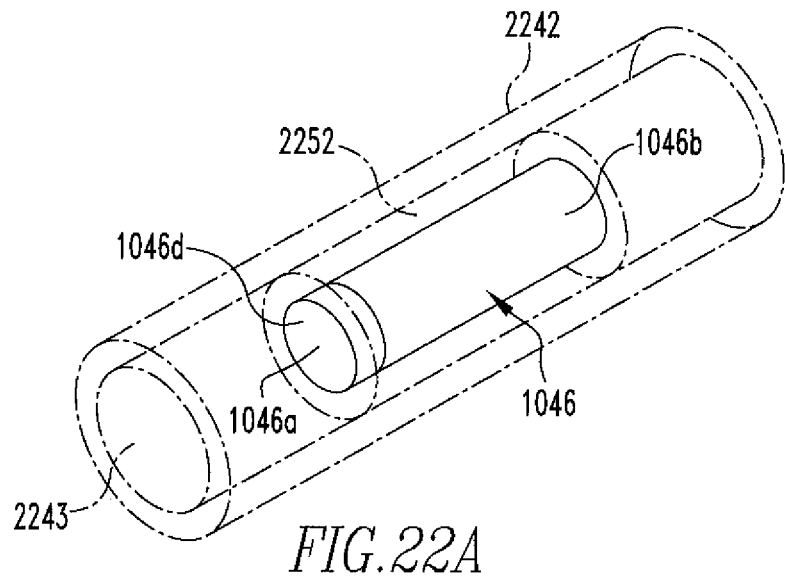
FIGS. 22A-22B, 23A-23B, 24A-24B, 25, and 26A-26B illustrate alternative configurations for holding a tissue scaffold within a sleeve of the tissue collection device of FIG. 10.
Figure 22B:
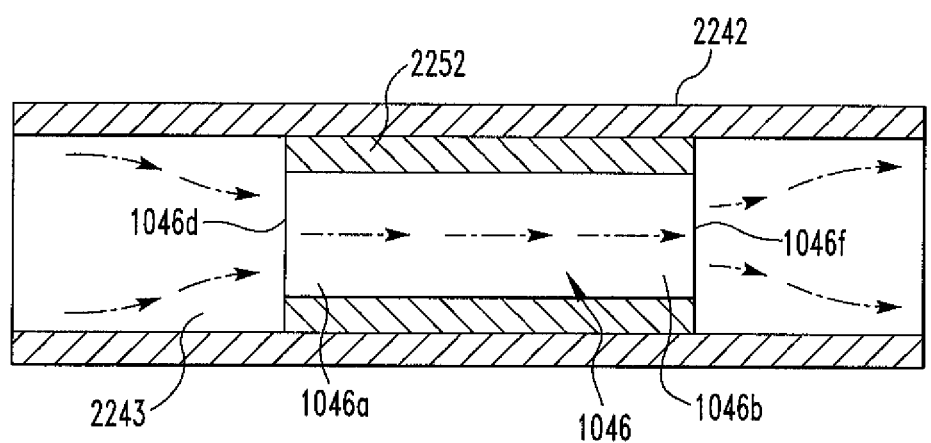

An alternative tissue collection housing 2242 for use with the tissue collection device 1040 is shown in FIGS. 22A-22B. The housing 2242 includes a cylindrical sleeve 2252 for holding the tissue scaffold 1046 within the housing 2242. The cylindrical sleeve 2252 is configured to be slidably received within the housing 2242 and held in place within a desired location within the housing 2242 by a frictional fit. The sleeve 2252 surrounds the entire exterior of the first region 1046a and second region 1046b of the tissue scaffold 1046 except for the face 1046d of the first region 1046a and the face 1046f of the second region 1046b, which are exposed to the interior 2243 of the housing 2242. In operation, as the cut tissue and fluid are aspirated through the tissue collection device 1040, the tissue and the fluid enter the scaffold 1046 through the face 1046d, travel substantially axially through the first region 1046a and the second region 1046b, and any tissue that is not captured by the tissue scaffold 1046, exits along with the fluid through the face 1046f (as illustrated by the arrows in FIG. 22B).

Figure 23A:
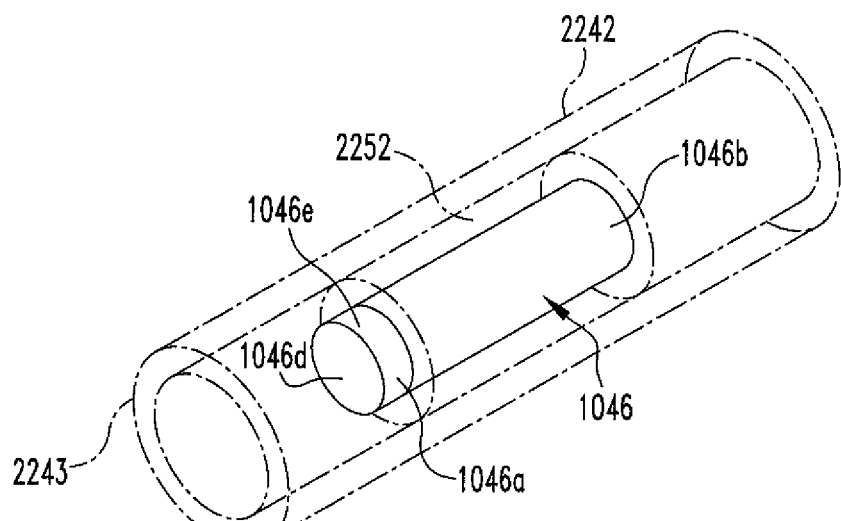
Figure 23B:
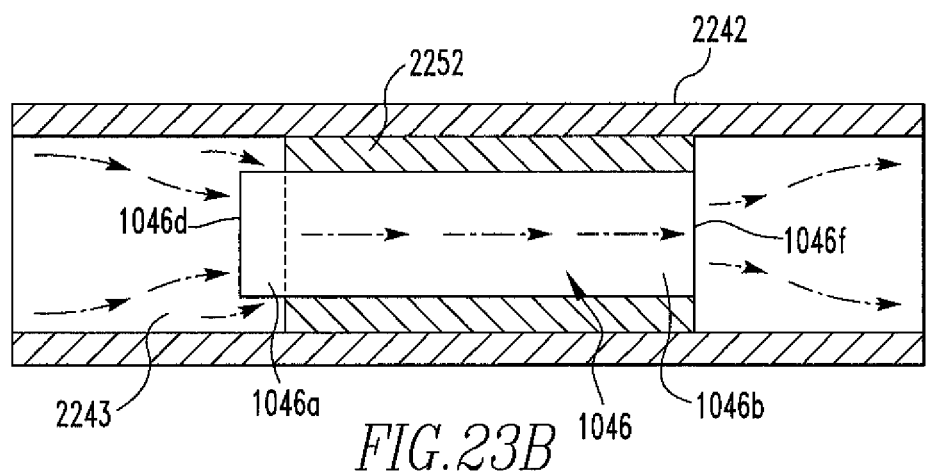

FIGS. 23A-23B illustrate an alternative configuration for placement of the tissue scaffold 1046 within the sleeve 2252. In this example, the sleeve 2252 surrounds the entire second region 1046b of the tissue scaffold 1046 but leaves the first region 1046a, including the face 1046d and the side portion 1046e, and the face 1046f of the second region 1046b, exposed to the interior 2243 of the housing 2242. As the cut tissue and fluid are aspirated through the tissue collection device 1040, the tissue and the fluid enter the scaffold 1046 through the face 1046d and the side portion 1046e of the first portion 1046a, travel through the first region 1046a and the second region 1046b, and any tissue that is not captured by the tissue scaffold 1046, exits along with the fluid through the face 1046f (as illustrated by the arrows in FIG. 23B). By allowing the first region 1046b to project from the sleeve 2252, the surface area of the first region 1046a is increased by about 240%, which leads to a higher population of tissue in the first region 1046a. This also provides a shorter flow path for the tissue fragments which leads to an increased flow rate and reduced overall procedure time.

Figure 24A:
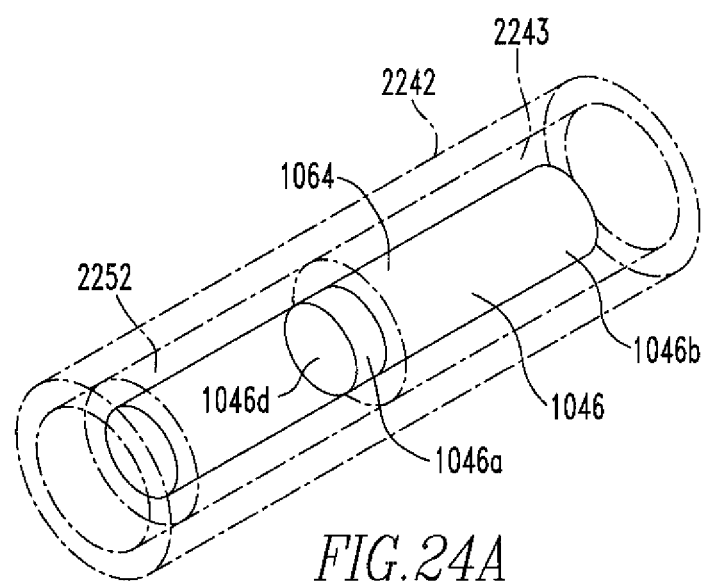
Figure 24B:
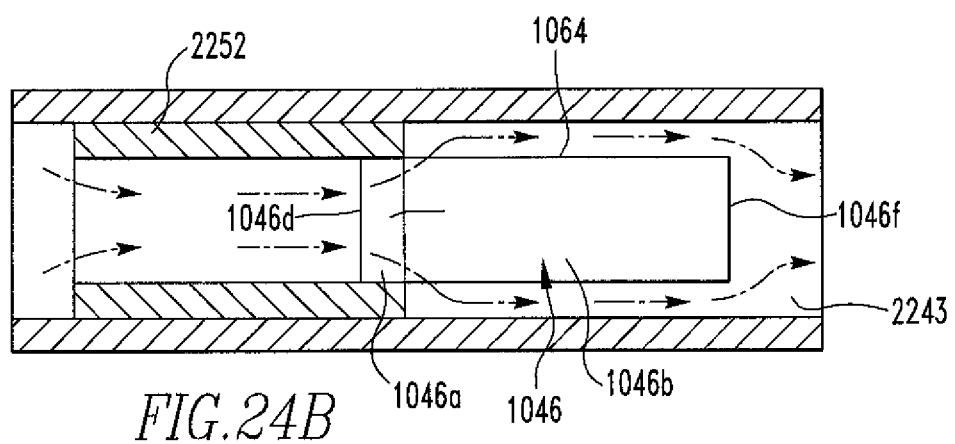

FIGS. 24A-24B illustrate another alternative configuration for placement of the tissue scaffold 1046 within the sleeve 2252. The sleeve 2252 surrounds the entire first region 1046a of the tissue scaffold 1046 but leaves the second region 1046b, including the face 1046f and a side portion 1064 exposed to the interior 2243 of the housing 2242. As the cut tissue and fluid are aspirated through the tissue collection device 1040, the tissue and the fluid enter the scaffold 1046 through the face 1046d of the first portion 1046a, and because a negative pressure is applied to the face 1046f and the side portion 1064 of the second region 1046b, the fluid and tissue flow through these surfaces and leave minimal traces of tissue in the second region 1046b. As shown in FIG. 24B, because of the negative pressure applied to the second region 1046b, a majority of the tissue and fluid flow out the second portion 1046b through the side portion 1064 immediately downstream of the intersection 1046c between the first region 1046a and the second region 1046b, resulting in a minimized flow path of tissue and fluid through the tissue scaffold 1046.

Figure 25:
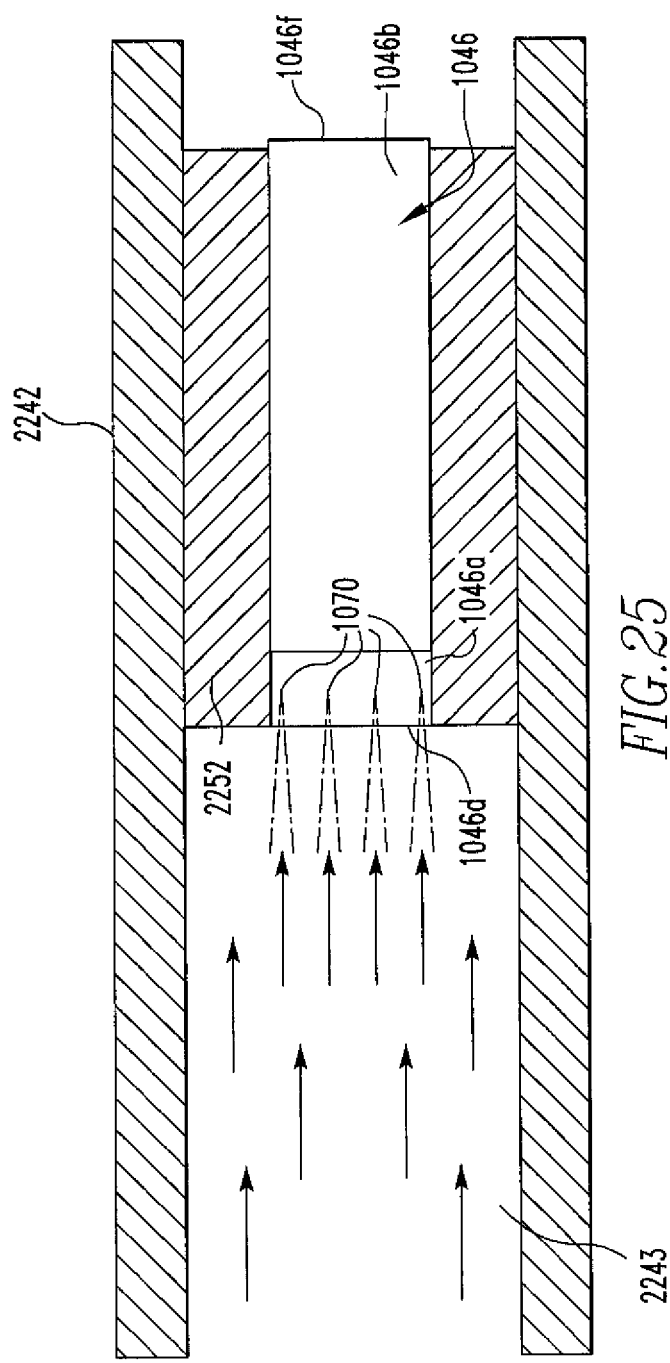

FIG. 25 illustrates a configuration wherein a set of pathways or piercings 1070 are formed in the first region 1046a of the tissue scaffold 1046 by, for example, piercing the first region 1046a with a needle or other suitable instrument. The pathways 1070 extend from the face 1046d of the first region 1046a to a desired location (e.g., to a point just prior to the intersection 1046c of the first region 1046a and the second region 1046b). As the cut tissue and fluid are aspirated through the tissue collection device 1040, the tissue and the fluid enter the scaffold 1046 through the face 1046d, travel substantially axially through the first region 1046a and the second region 1046b, and any tissue that is not captured by the tissue scaffold 1046, exits along with the fluid through the face 1046f. The pathways 1070 allow for deep penetration of the tissue fragments along a desired path through the first region 1046a. This configuration provides a degree of controlled tissue loading to the tissue collection device 1040. As an alternative to forming a set of pathways 1070 in the first region 1046a, a set of tissue-containing needles (not shown) can be used to provide for controlled distribution of the tissue fragments into the first regions 1046a. The needles (not shown) pierce the first region 1046a, inject the tissue into the desired locations within the first region 1046a, and are retracted from the tissue scaffold 1046 following injection.

Figure 26A:
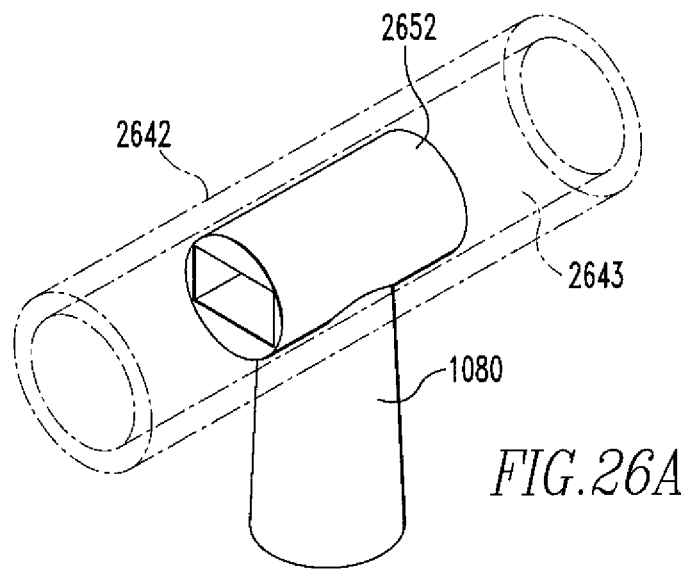
Figure 26B:
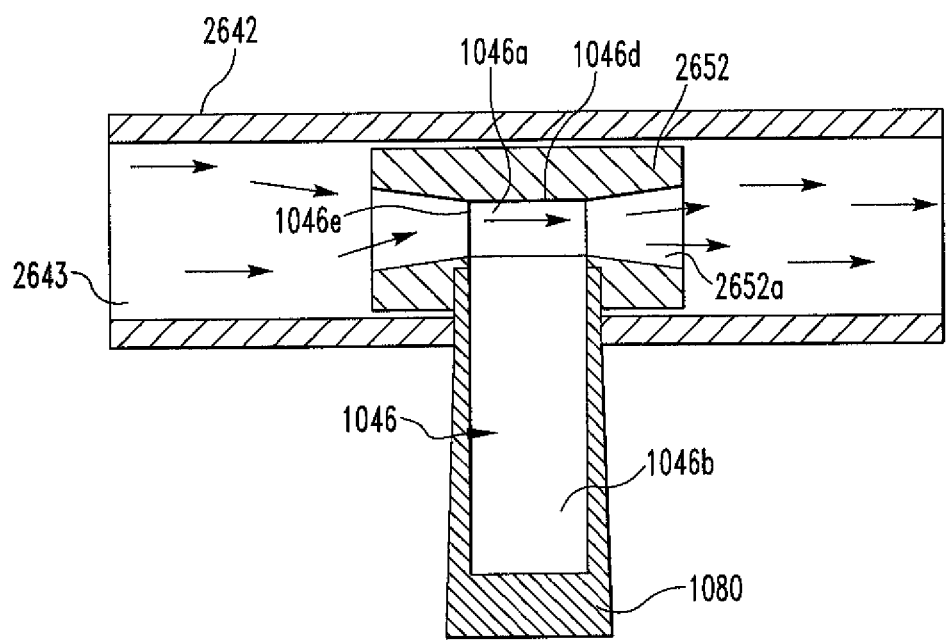

A further alternative tissue collection housing 2642 for use with the tissue collection device 1040 is shown in FIGS. 26A-26B. The cylindrical sleeve 2652 defines a rectangular, venturi-shaped fluid-flow passageway 2652a. The tissue scaffold 1046 is positioned transverse to the flow of the cut tissue and the fluid through the interior 2643 of the tissue collection housing 2642. In addition to the sleeve 2652, the housing 2642 includes a cylindrical tube 1080 that receives and surrounds the second region 1046b of the tissue scaffold, and is positioned with respect to the sleeve 2652 to provide a compression force on the tissue scaffold 1046 such that the face 1046d of the first region 1046a is sealed against the sleeve 2652 as shown in FIG. 26B. Accordingly, only the side portion 1046e of the first region 1046a is exposed to the flow of tissue and fluid through the interior 2643 of the housing 2642. As the cut tissue and fluid are aspirated through the tissue collection device 1040, the tissue and the fluid enter the scaffold 1046 through the face side portion 1046e of the first portion 1046a, travel exclusively through the first region 1046a, and any tissue that is not captured in the first region 1046a, exits along with the fluid through the opposing side portion 1046e (as illustrated by the arrows in FIG. 26B). This provides a shorter flow path for the tissue fragments which leads to an increased flow rate and reduced overall procedure time.

An alternative implementation of a tissue collection device 2040 (FIG. 29) for use with the tissue harvesting assembly 100 includes a housing 2042 having a first end 2042a and a second end 2042b. The housing 2042 defines a substantially cylindrical cut out portion 2055 that further defines a shoulder 2055a. The portion 2055 receives a biodegradable, fluid permeable, implant material, or tissue scaffold 2046, configured in the form of a cup. The cup scaffold 2046 is received in the portion 2055 such that fluid and cut tissue flow substantially through an open interior 2046a of the cup scaffold 2046 and through a bottom face 2046b of the cup scaffold 2046 as depicted by the arrows in FIG. 29. Cup scaffold 2046, and in particular the bottom face 2046b of the cup scaffold 2046 includes openings sized in the range of about 500 μm to about 1 mm to capture particles of a desired size for later implantation into a surgical site. The first and second ends 2042a and 2042b of the housing 2042 are releasably coupled to each other using any suitable means, such as adhesives, screws, or by clamping the two ends 2042a and 2042b together, which facilitates removal of the cup scaffold 2046 from the housing 2042 as will be explained in more detail below.

Removably coupled to the first and second ends 2042a, 2042b, respectively, of the housing 2042, are an inlet connector 2044 and an outlet connector 2048. The connectors 2044 and 2048 are removably coupled to the first and second ends 2042a, 2042b, respectively, using, for example, mating threaded connections (not shown) on the inlet connector 2044, the outlet connector 2048, and the housing 2042; adhesive; an interference friction fit between the ends of the housing 2042 and corresponding receiving portions (not shown) formed in the inlet connector 2044 and the outlet connector 2048; or other suitable methods. The connectors 2044, 2048 form a fluid-tight seal with the housing 2042. The inlet connector 2044 includes a tubing connector portion 2044a that couples the tissue collection device 2040 to the blade 10 (FIG. 1) via a flexible tubing (not shown). The outlet connector 2048 includes a tubing connector 2048a that couples the tissue collection device 2040 to a tubing (not shown) and to a source of vacuum 70 (FIG. 1). Fluid and cut tissue are aspirated through the tissue collection device 2040 to load the cup scaffold 2046 with cut tissue as explained in more detail below.

Disposed within the housing 2042 are a set of filters 2030a, 2030b. The first filter 2030a has openings sized between, e.g., about 600 μm to about 3 mm, and in a particular implementation, the opening size is about 2.4 mm. The second filter 2030b has openings sized between, e.g., about 600 μm to about 1 mm, and in a particular implementation, the opening size is about 0.6 mm.

The cup scaffold 2046 includes an annular lip 2047 that cooperates with the shoulder 2055a of the portion 2055 of the housing 2042 to maintain the cup scaffold 2046 in position relative to the housing 2042 and to assist with removal of the cup scaffold 2046 from the housing 2042 as will be described in more detail below. Alternatively, the cup scaffold 2046 may be formed without the lip 2047. Attached to one side of the second filter 2030b is an insert or plunger 2050 including a disc-shaped portion 2050b and a cylindrical rod 2050a extending therefrom. As schematically depicted in FIG. 29, insert 2050 may be attached to the second filter 2030b by screwing a threaded end (2051) of the rod 2050a into a mating hole (not shown) in the filter 2030b, gluing the rod 2050a to the filter 2030b, molding the insert 2050 and rod 2050a as part of the second filter 2030b, or by other suitable means. The insert 2050 is configured to limit the amount of buildup of tissue within the cup scaffold 2046.

Figure 30B:
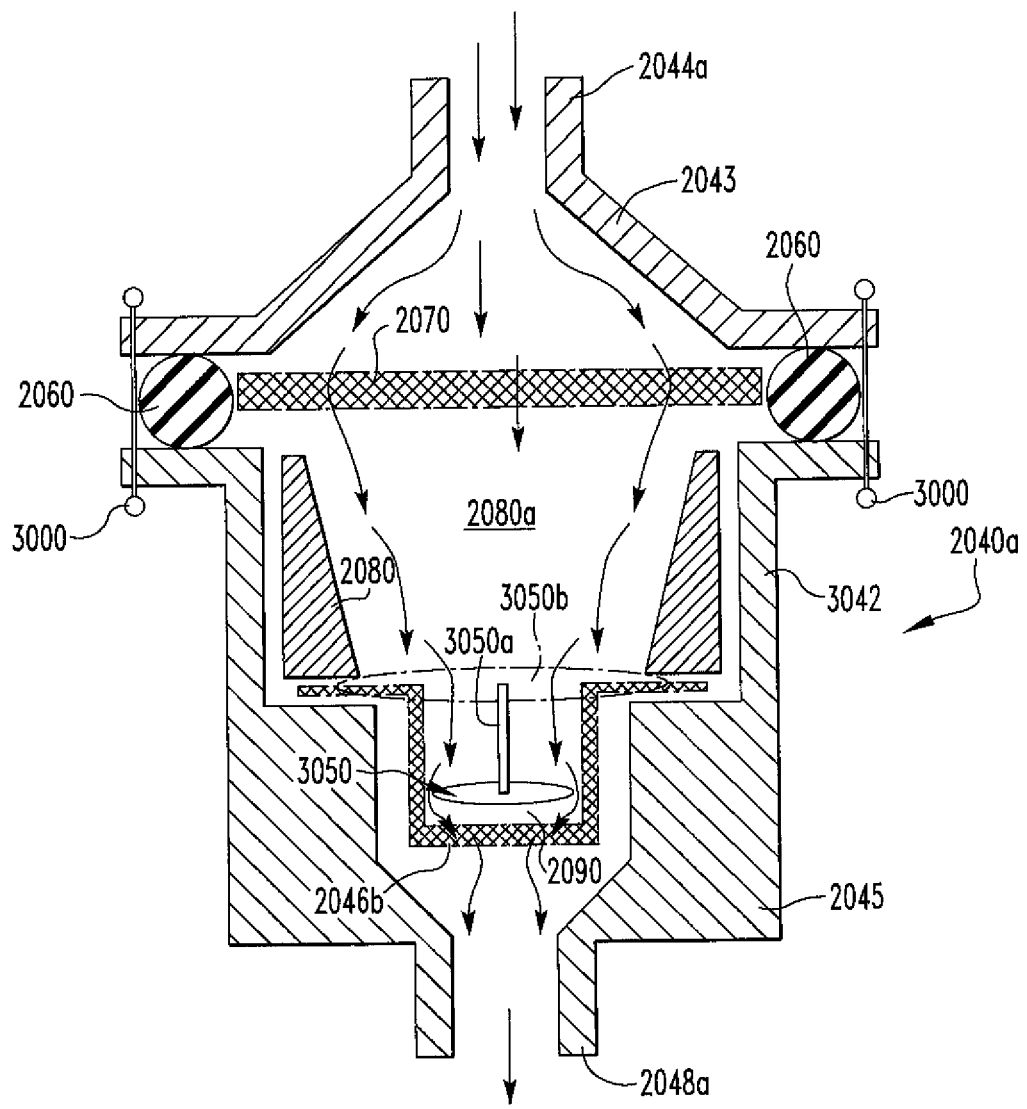
FIG. 30B is a cross-section view of an alternative housing configuration of the tissue collection device of FIG. 30.

In an alternative implementation illustrated in FIGS. 30A and 30B, a tissue collection device 2040a includes a housing 3042 having a first housing portion 2043 and a second housing portion 2045 coupled together using connectors 3000, such as bolts, screws, clamps, or any other suitable means. Disposed between the first housing portion 2043 and the second housing portion 2045 is a seal member 2060, such as an o-ring, gasket, or other sealant, to provide a fluid-tight seal between the housing portions 2043, 2045. Captured between the first and second housing portions 2043, 2045 is a single filter 2070 that has a set of openings sized between about 0.6 mm to about 2.4 mm, and in a particular implementation has a set of openings sized about 0.6 mm.

The housing 3042 further includes a flow diverter 2080 disposed in the housing 3042 between the filter 2070 and the cup scaffold 2046. The diverter 2080 includes a generally tapered internal lumen 2080a for directing flow of fluid and tissue from the filter 2070 into the cup scaffold 2046 as depicted by the arrows in FIGS. 30A and 30B. As further illustrated in FIG. 30A, an insert 3050 includes a rod 3050*a* and a disc-shaped member 3050*b* disposed between the diverter 2080 and the annular lip 2047 of the cup scaffold 2046. The disc-shaped member 3050*b* maintains the position of the insert 3050 relative to the cup scaffold 2046 when the housing 3042 is assembled and assists in removing the insert 3050 from the cup scaffold 2046 as will be discussed in more detail below.

Figure 31:
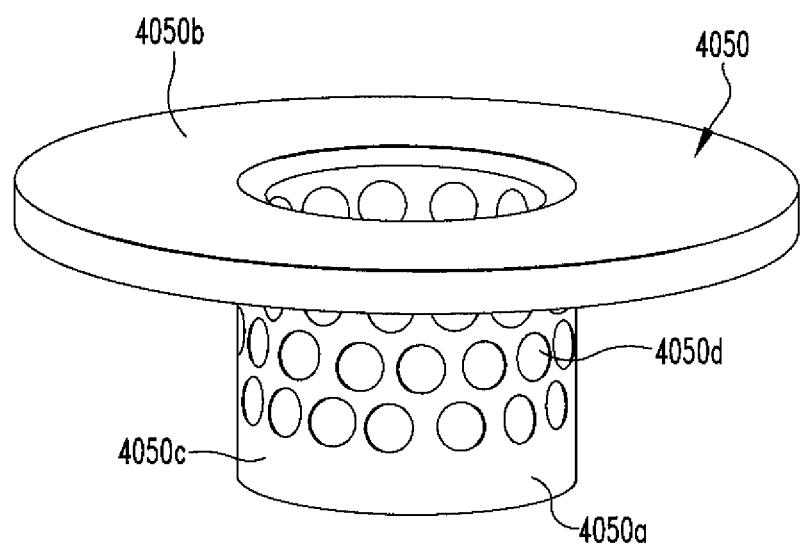
FIG. 31 is a perspective view of an alternative insert for use with the housing of FIGS. 30A and 30B.

An alternative insert 4050 (FIG. 31) may be employed with, for example, the housing 3042 of FIGS. 30A and 30B. As shown in FIG. 31, the insert 4050 includes a disc-shaped member 4050*b* and a cup-shaped portion 4050*c* having a closed end 4050*a* extending from the disc-shaped member 4050*b*. The cup-shaped portion 4050*c* is configured in substantially the same shape as the cup scaffold 2046 and is configured to fit within the open interior of the cup scaffold 2046. The cup-shaped portion 4050*c* includes openings 4050*d* which permit fluid and cut tissue to flow through the portion 4050*c* and thereafter through the cup scaffold 2046 during use of the assembled housing 2042. The insert 4050 acts to limit the amount of tissue buildup in the cup scaffold 2046.

In operation, the surgical blade 10 (FIG. 1) is brought into contact with a desired bodily tissue, such as adipose or synovial tissue. The operator cuts a desired amount of tissue from the donor site using the blade 10. The vacuum source 70 (FIG. 1) aspirates the fluid and the cut tissue through, for example, the housing 2042 such that the fluid and cut tissue enter through the housing inlet 2044 and pass through either the two filters 2030*a*, 2030*b* (FIG. 29) or through the single filter 2070 (FIG. 30), which remove cut tissue that is larger than the opening sizes of the filters, from the fluid pathway. The fluid and cut tissue are then directed into the cup scaffold 2046 where they flow between insert 2050 and the inner wall of the cup scaffold 2046 as depicted by the arrows in FIGS. 29 and 30A. The spacing between the insert 2050 and the cup scaffold 2046 is in the range of between about 1 mm to about 5 mm, and in certain implementations, is in the range of between about 2 mm to about 4 mm.

Tissue that is larger than the pore size of the bottom face 2046*b* of the cup scaffold 2046 then collects in the area 2090 (FIG. 30) formed between the plunger 2050 and the bottom face 2046*b* of the cup scaffold 2046 and continues to collect until, for example, the tissue reaches the insert 2050, thereby loading the cup scaffold 2046 with tissue in the area 2090. Any cut tissue that is smaller than the pore size of the bottom face 2046*b* of the cup scaffold 2046 and fluid pass through the cup scaffold 2046 and are aspirated through the outlet 2048 to a collection apparatus, not shown. Depending on the type of procedure and the type of tissue, the tissue will generally collect to a depth of up to about 4 mm. Once a desired amount of tissue is collected in the area 2090, the housing 2042 may be opened and the insert 2050 removed from the cup scaffold 2046 by removing the filters 2030*b* from the housing 2042 (FIG. 29) or by grasping the member 2050*b* and removing the insert 2050 from the cup scaffold 2046 (FIG. 30A). Once the insert 2050 is removed from the cup scaffold 2046, the operator then removes the cup-scaffold 2046 from the housing 2042 and implants the cup scaffold 2046 into a surgical site 320 (as depicted in FIG. 33) that has been prepared to receive the cup scaffold 2046, such as the surgical site depicted in FIG. 32.

Figure 32:
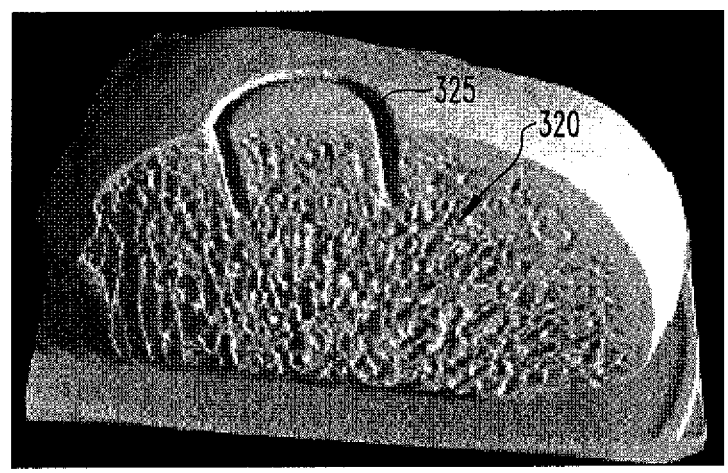
FIG. 32 is a cross-section view of a surgical site prepared to receive a tissue scaffold used in the implementation of the tissue collection device of FIG. 29.
Figure 33:
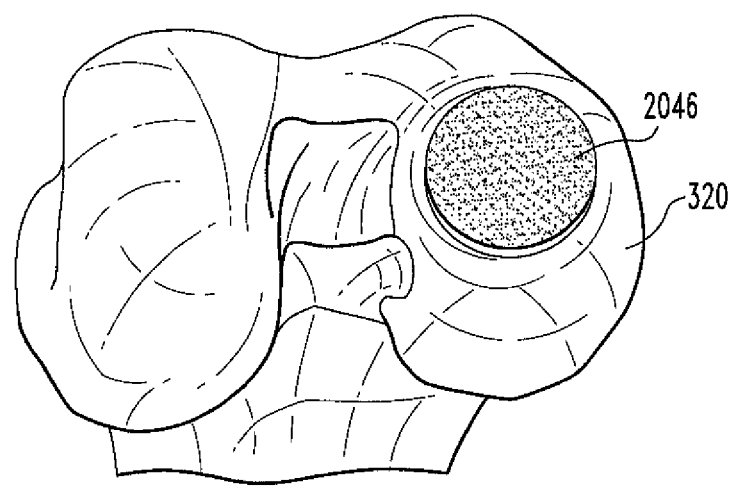
FIG. 33 is a perspective view of a cup scaffold positioned in the surgical site of FIG. 31.

As shown in FIG. 32, use of the cup scaffold 2046 provides a significant decrease in the amount of bone removal required for placement of the tissue scaffold into the surgical site. For example, instead of removing a cylindrical portion of bone for implantation of plug-type tissue scaffolds, such as scaffold 46 (FIG. 9B), the cup scaffold 2046 only requires removal of a small annular groove 325 from the surgical site 320, which can result in as much as a 90% reduction in bone loss.

In addition to being used in conjunction with the surgical blade assemblies described above, each of the tissue collection devices 40, 1040, 2040, and 2040*a* can be loaded with biological components by other methods. For example, cell pellets cultured in-vitro can be aspirated (e.g. using a vacuum source) through one of the tissue collection devices 40, 140, 240 and then mixed with a biocompatible gel in the manner described above.

Figure 34A:
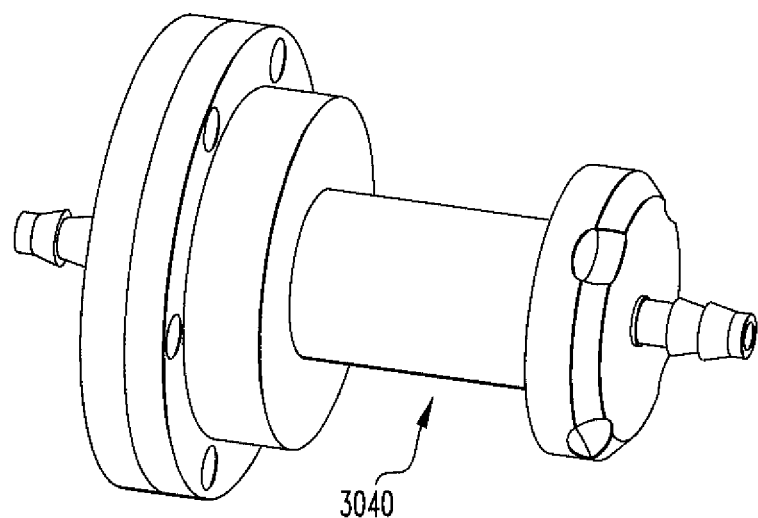
FIGS. 34A-34B are perspective views of alternative embodiments of the tissue collection apparatus of the present disclosure.
Figure 34B:
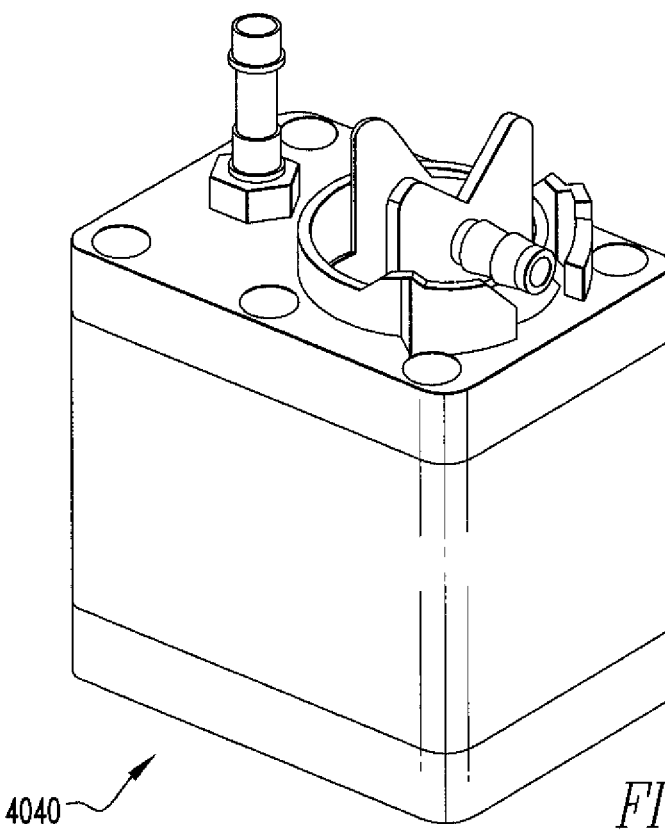

FIGS. 34A-34B illustrate two alternative embodiments of the tissue collection apparatus. FIG. 34A, shows a "cylinder" design 3040 and is further described below in FIGS. 35-41, while FIG. 34B shows a "tub" design 4040 and is further described below in FIGS. 42-47. Other designs or shapes for the tissue collection apparatus are within the scope of this disclosure.

Figure 35:
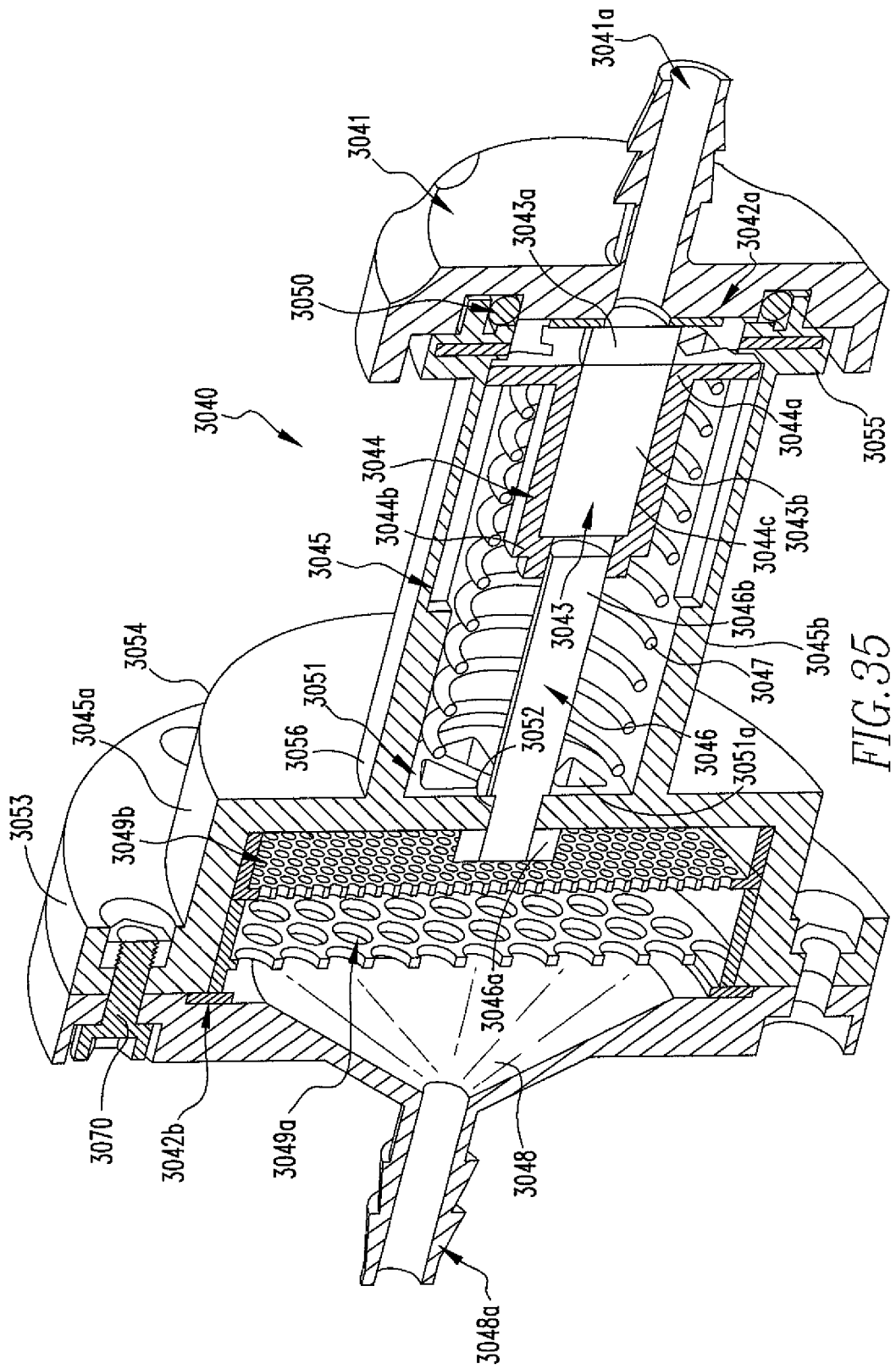
FIG. 35 is a cross-sectional view of the tissue collection apparatus of FIG. 34A.

FIG. 35 is a cross section of the tissue collection apparatus 3040 shown in FIG. 34A. The apparatus 3040 includes a housing 3045 having a base portion 3045*a*, including a proximal end 3053 and a distal end 3054, and a shaft portion 3045*b*, including a distal end 3055 and a proximal end 3056, extending from the distal end 3054 of the base portion 3045*a*, an outlet cap 3041, including an outlet 3041*a*, coupled to the distal end 3055 of shaft portion 3045*b*, and an inlet connector 3048, including an inlet 3048*a*, coupled to the proximal end 3053 of the base portion 3045*a*. A set of filters 3049*a*, 3049*b* are located in the base portion 3045*a* of the housing 3045. The filters 3049*a*,3049*b* are coupled to the base portion 3045*a* via an adhesive, interference friction fit, or other suitable method. When there is a set of filters, the first filter 3049*a* has a set of openings having an opening size of between about 600 µm to about 3 mm. The second filter 3049*b* has a set of openings having an opening size of between about 600 µm to about 1 mm. The first filter 3049*a* catches the larger tissue particles first and allows the more moderate size tissue particles to be caught by the second filter 3049*b*. If there is only one filter, the larger tissue particles may tend to clog the filter more quickly. The flow of tissue through the apparatus 3040 will be further described below.

Figure 36:
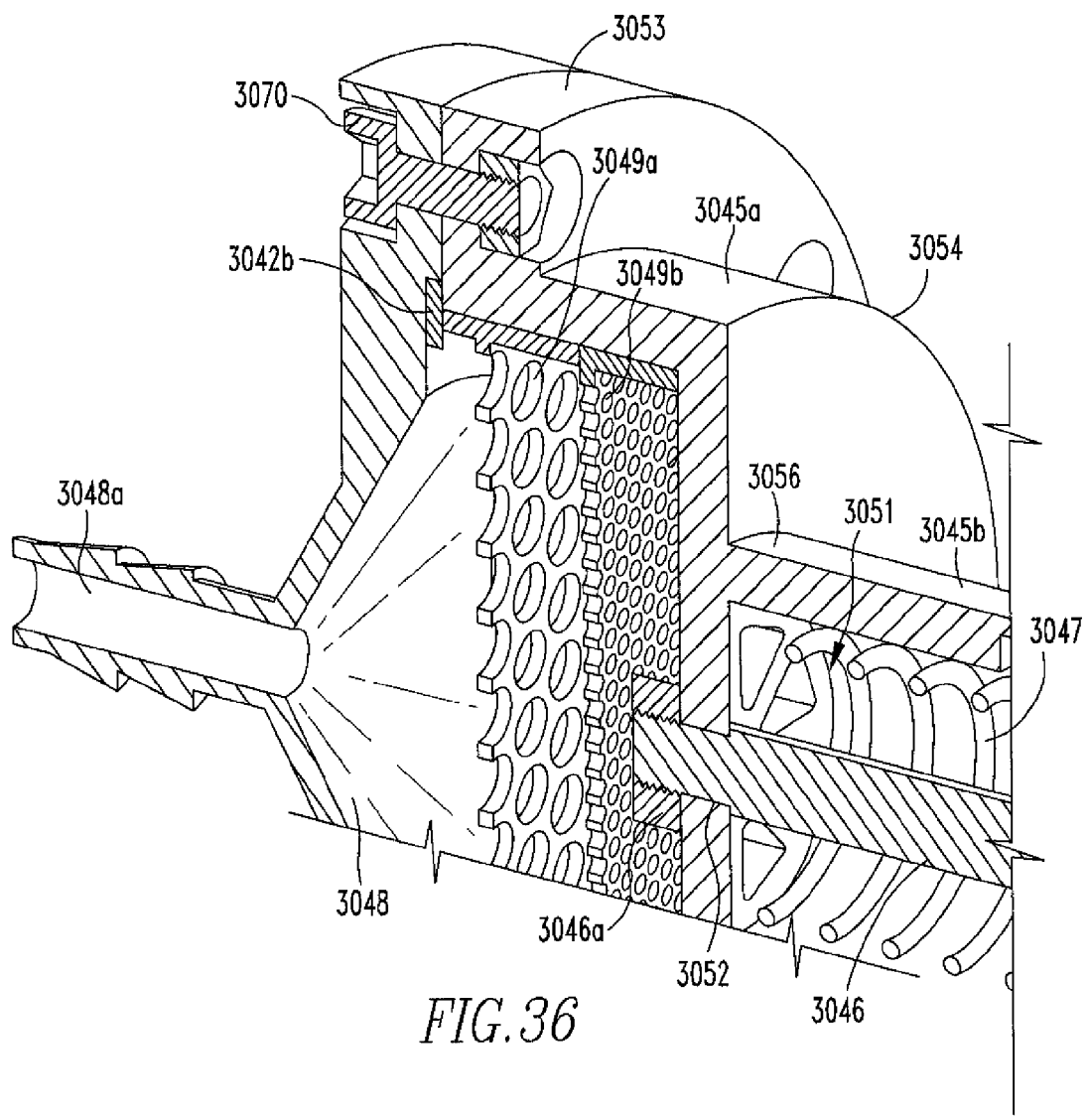
FIG. 36 is a cross-sectional view of the housing base portion and inlet connector of the tissue collection apparatus of FIG. 34A.

Located between the shaft portion 3045*b* and the base portion 3045*a* is a rim 3051. The rim 3051 includes openings 3051*a* and serves to separate components of the shaft, specifically the spring 3047, from the filters 3049*a*,3049*b*. The base portion 3045*a* also includes a through hole 3052. A post 3046, having a radially extending proximal portion 3046*a* and a distal portion 3046*b*, is housed within the through hole 3052. The proximal portion 3046*a* is located within the base portion 3045*a* and the distal portion 3046*b* is located within the shaft portion 3045*b*. The purpose of the post 3046 is further described below. The proximal end 3053 of the base portion 3045*a* is coupled to the inlet connector 3048 by press-fitting the end 3053 to the base portion 3045*a* and additionally via the use of a fixation device 3070, such as an Allen screw or other type of fixation device. Other methods of coupling are within the scope of this disclosure. In addition, a gasket 3042*b*, as shown more clearly in FIGS. 36 & 37, is located between the base portion 3045*a* and the inlet connector 3048 to create a fluid seal between the base portion 3045*a* and the inlet connector 3048 and to substantially reduce any axial tolerances on the filters 3049*a*,3049*b*.

Located within the shaft portion 3045*b* is a spring 3047 that extends a length of the shaft portion 3045*b*, the distal portion 3046*b* of the post 3046, and a sleeve 3044. The spring 3047 facilitates axial movement of the sleeve 3044 within the shaft 3045b during coupling and removal of the cap 3041, as will be further described below. The sleeve 3044 includes a proximal end 3044b configured for engagement with the distal portion 3046b of the post 3046 and a distal end 3044a having tabs 3057 (FIG. 37) and first and second arms 3058,3059 extending from the distal end 3044a. The sleeve 3044 is located in the shaft portion 3045b such that surfaces 3058a,3059a of the arms 3058,3059 engage an inner wall 3045c of the housing 3045. A tissue scaffold 3043, as described above, is located within an internal cavity 3044c of the sleeve 3044 such that a second region 3043b of the scaffold 3043 is contained within the sleeve 3044 and a first region 3043a extends from the distal end 3044a of the sleeve 3044. The distal portion 3046b of the post 3046 extends into the inner cavity 3044c of the sleeve 3044 to substantially reduce the possibility of the scaffold 3043 becoming lodged within the inner cavity 3044c of the sleeve 3044 during extraction of the scaffold 3043 from the sleeve 3044, as will be further described below. As shown more clearly in FIG. 37, a gap 3060 is located between the distal end 3046b of the post 3046 and the scaffold 3043. The gap 3060 allows for axial movement of the sleeve 3044 when the outlet cap 3041 is rotated and removed from the housing 3045, as will be further described below.

Figure 37:
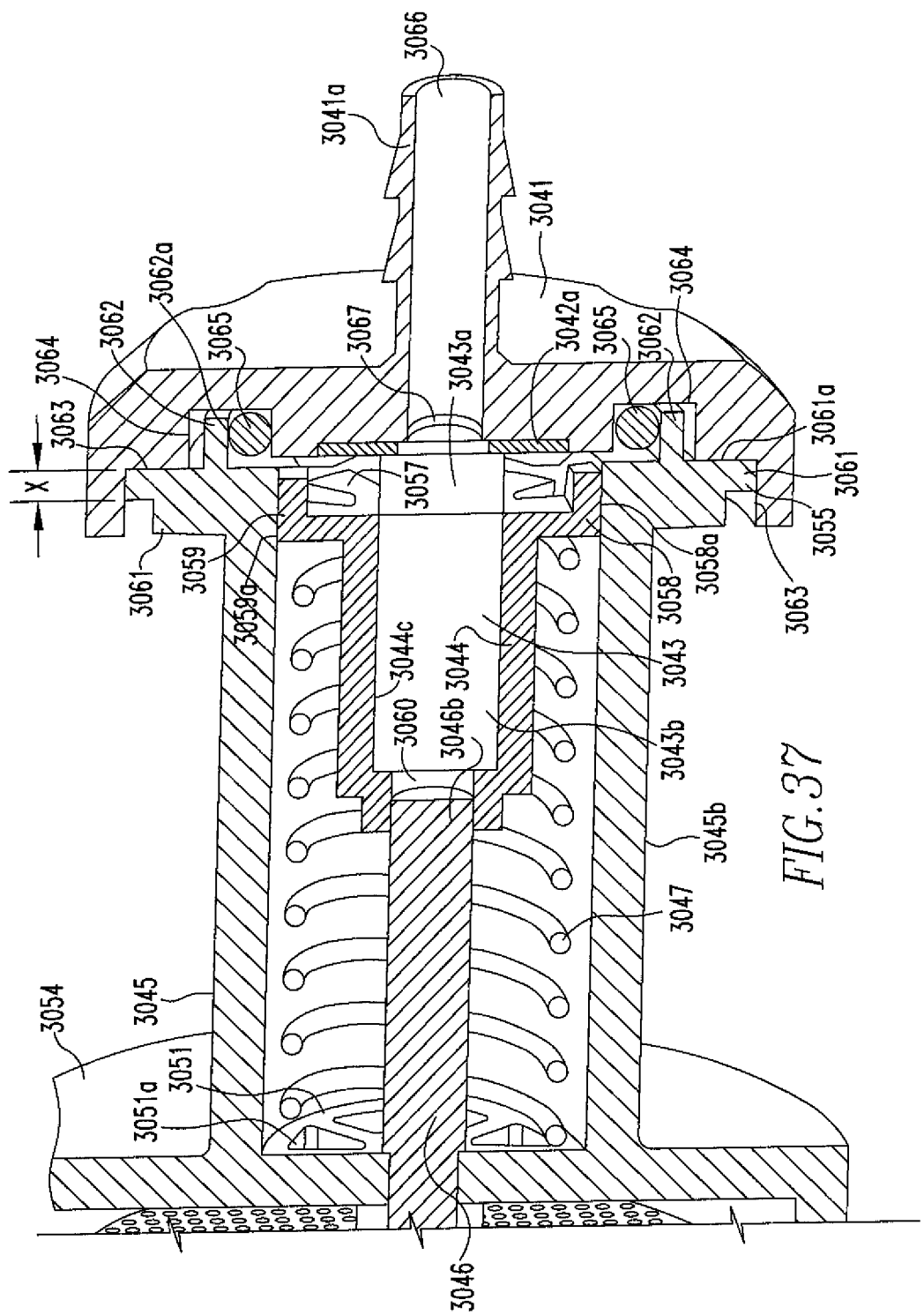
FIG. 37 is a cross-sectional view of the housing shaft and outlet cap of the tissue collection apparatus of FIG. 34A.

As shown more clearly in FIG. 37, the distal end 3055 of the shaft 3045b includes a radially extending edge portion 3061 and a protrusion 3062 located on a surface 3061a of the edge portion 3061. The outlet cap 3041 includes a first groove 3063 configured to engage the edge portion 3061 when the outlet cap 3041 is coupled to the shaft 3045b and a second groove 3064 configured to engage the protrusion 3062 when the outlet cap 3041 is coupled to the shaft 3045b. The outlet cap 3041 also includes an O-ring 3065 located within the second groove 3064. When the outlet cap 3041 is engaged with the distal end 3055 of the shaft 3045b, the O-ring 3065 is compressed radially between the cap 3041 and an inner wall 3062a of the protrusion 3062, thereby providing the radial location of the outlet cap 3041 on the shaft 3045. In this manner, as more clearly shown in FIG. 38, radial compression of the O-ring 3065 is greater on the cap 3041 than on the inner wall 3062a, thereby substantially increasing the possibility of the O-ring 3065 remaining coupled to the cap 3041 when the cap 3041 is removed, as will be further described below. The axial location of the outlet cap 3041 on the shaft 3045 is set by "X", or the height of the first groove 3063. Retention features, other than an O-ring, are within the scope of this disclosure and may be used.

Figure 38:
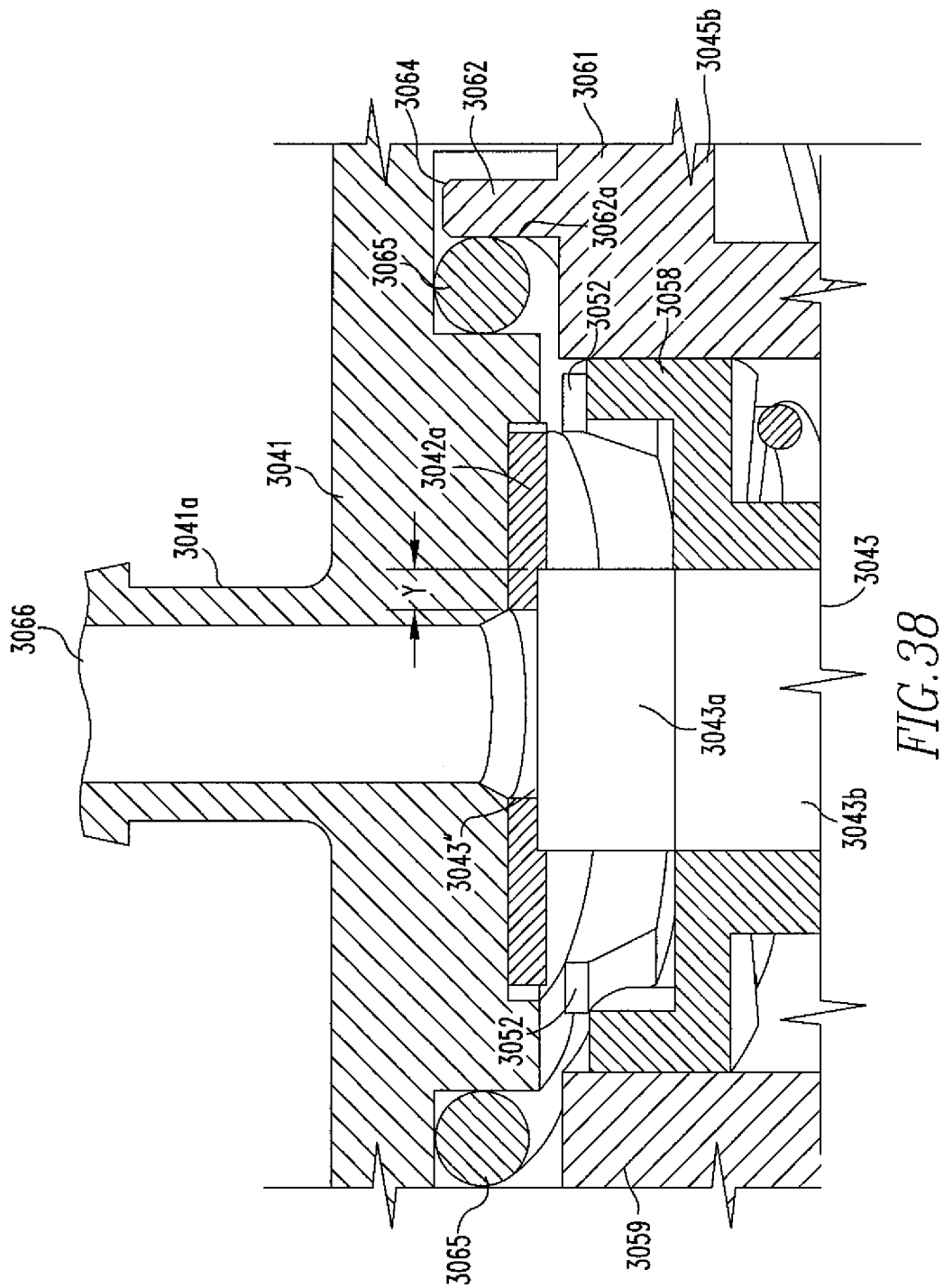
FIG. 38 is a cross-sectional view showing the overlap between the scaffold and scaffold gasket of the tissue collection apparatus of FIG. 34A.

The outlet 3041a includes a through hole 3066 extending a length of the outlet 3041a. Located between the cap 3041 and the housing 3045 is a scaffold gasket 3042a. As shown in FIG. 37, the scaffold gasket 3042a includes a through hole 3067, such that the through hole 3067 of the gasket 3042a is aligned with the through hole 3066 of the outlet 3041a. FIG. 37, and especially FIG. 38, shows a radial overlap, represented by the distance "Y", which exists between the first region 3043a of the scaffold 3043 and the scaffold gasket 3042a. The overlap is large enough to substantially reduce the scaffold 3042a from extending through the through hole 3067, yet small enough to substantially reduce blocking of the pores in the second region 3043b of the scaffold 3043. In terms of size, the overlap remains the same independent of the diameter of the scaffold 3043, with the overlap covering up to about 10% of the diameter of the scaffold 3043.

Figure 39:
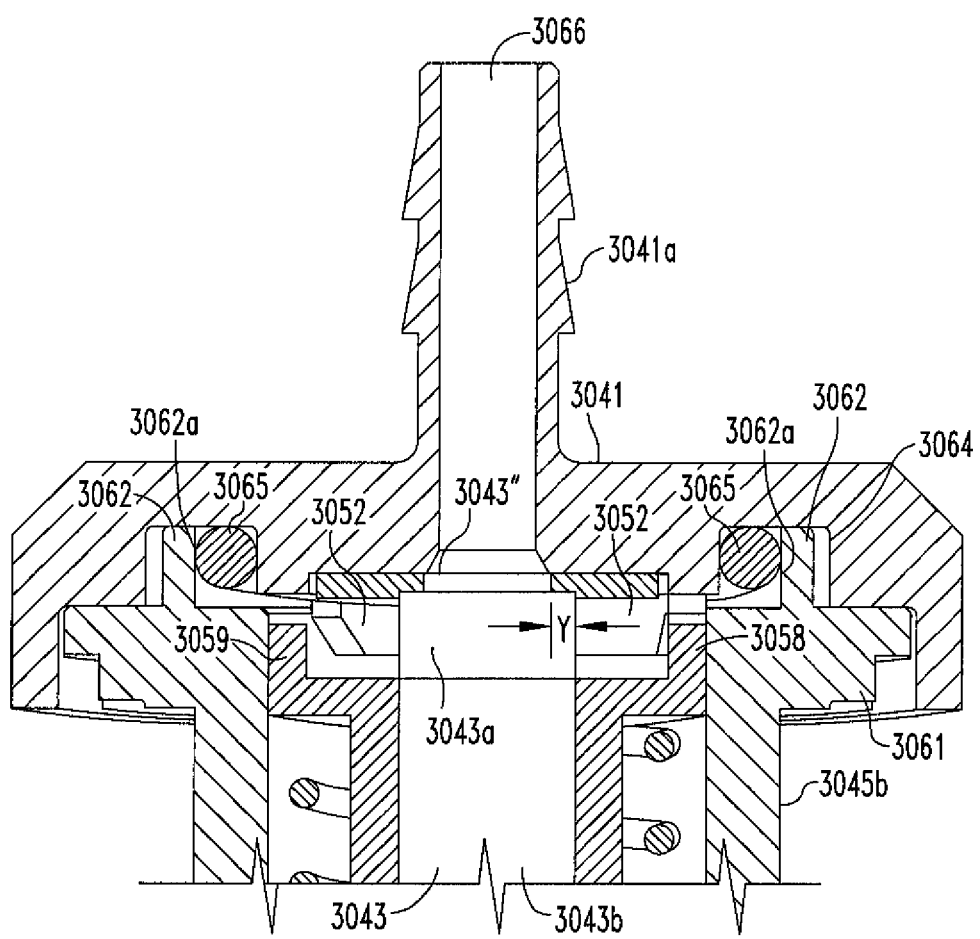
FIG. 39 is a cross-sectional view showing the outlet cap ramps of the tissue collection apparatus of FIG. 34A.

FIGS. 38 and 39 show the location of ramps 3052 that are coupled to the cap 3041. These ramps 3052 cover about 180° of rotation so that the scaffold 3043 is only in contact with the scaffold gasket 3042a over a small angle of rotation, as will be further described below. This substantially reduces the possibility of damage to the open face 3043" of the scaffold 3043 when the cap 3041 is inserted onto and removed from the shaft 3045b, as will be further described below.

In operation, the surgical blade 10 (FIG. 1) is brought into contact with a desired bodily tissue, such as adipose or synovial tissue. The operator cuts a desired amount of tissue from the donor site using the blade 10. The vacuum source 70 (FIG. 1) aspirates the fluid and the cut tissue through the filters 3049a,3049b, which remove cut tissue that is larger than the opening sizes of the filters, from the fluid pathway, and to the shaft portion 3045b. The cut tissue and fluid flow over and around the exterior of the sleeve 3044 and enter the side 3043a' of the first region 3043a of the tissue scaffold 3043 (as depicted by the arrows in FIG. 40). Because the sleeve 3044 completely surrounds the exterior of the second region 3043b of the tissue scaffold 3043, and because the bonding agent (e.g., adhesive) between the first region 3043a and the second region 3043b of the tissue scaffold 3043 minimizes flow of tissue and fluid therethrough, the cut tissue and fluid flows through the first region 3043a of the tissue scaffold 3043. In particular, the tissue and fluid flow through the side 3043a' of the first region 3043a and out of the circular face 3043" (FIG. 40), thereby loading only the first region 3043a, including the interior and exterior of the first region 3043a, with cut tissue for later implantation into the desired site to be treated.

FIGS. 41A-D illustrates the use of the apparatus 3040 by a surgeon. The scaffold 3043 is pre-loaded under sterile conditions in a manufacturing facility within sleeve 3044 such that a portion, at least part of the cartilage phase or first region 3043a, of the scaffold 3043 protrudes from the sleeve 3044. Prior to use of the apparatus 3040, the cap 3041 is coupled to the apparatus 3040, as shown in FIG. 39, such that the ramps 3052 are not in contact with the arms 3058a,3059a of the sleeve 3044 and the scaffold 3043 is not under pressure by the gasket 3042a and the cap 3041. In anticipation of use of apparatus 3040, the surgeon turns the cap 3041 clockwise about 45°, as shown by the arrow in FIG. 41A, such that the ramps 3052 engage arm 3059a, thereby facilitating movement of the sleeve 3044 within the shaft 3045b and an application of pressure on the scaffold 3043 by cap 3041 and gasket 3042b. In addition to the ramps 3052, as described above, the O-ring applies pressure, via radial compression, to the wall 3062a to couple the cap 3041 to the shaft 3045b. Tubes, as described above and represented by arrows in FIG. 41B, are coupled to the inlet 3048a on the inlet connector 3048 and the outlet 3041a on the cap 3041 and tissue is harvested, in the manner described above.

Figure 41A:
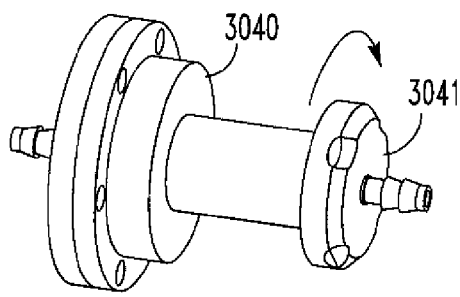
FIGS. 41A-41D are perspective views illustrating use of the tissue collection apparatus of FIG. 34A.
Figure 41B:
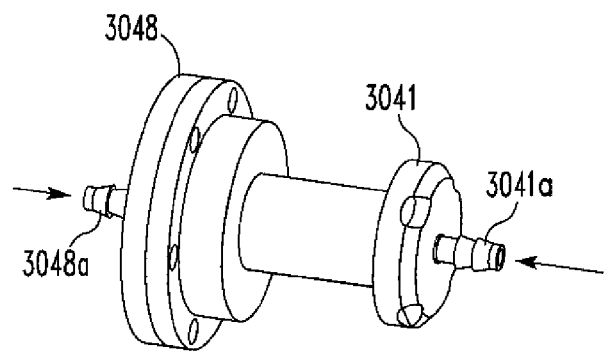
Figure 41C:
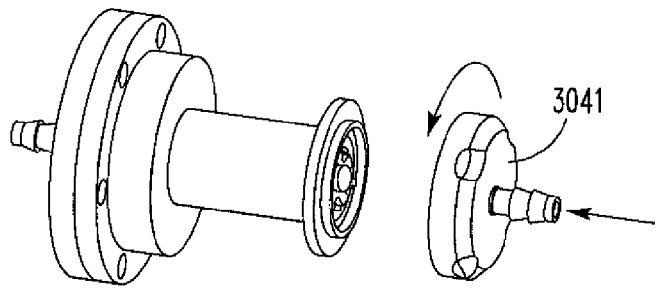
Figure 41D:
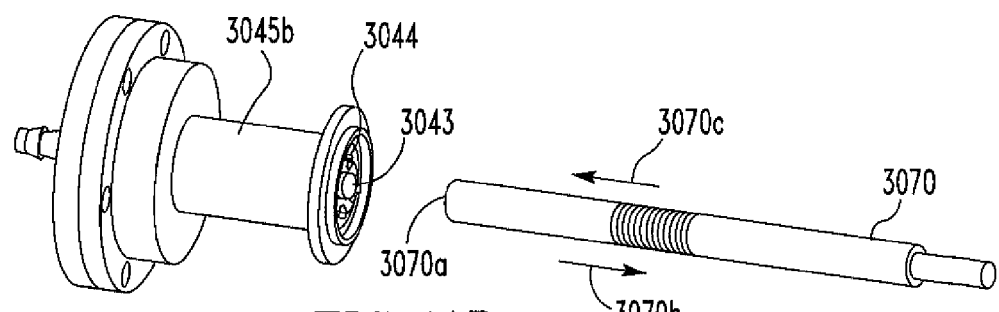

After the scaffold 3043 has been loaded with tissue, the cap 3041 is removed by turning the cap 3041 anti-clockwise about 90°, as shown by the arrow in FIG. 41C, such that the ramps 3052 are disengaged from the sleeve 3044 and pressure is released from the scaffold 3043. A tissue scaffold delivery device 3070 (FIG. 41D), as described above and shown in FIG. 9A, is used to remove the tissue seeded-scaffold 3043 from sleeve 3044 such that an end 3070a of the device 3070 is placed over the scaffold 3043 and downward pressure (3070c) is applied to the device 3070 to insert the scaffold 3043 into the end 3070a of the device 3070. While the downward pressure 3070c is applied to the device 3070, movement of the sleeve 3044 occurs within the shaft 3045b, thereby substantially reducing the gap 3060 between the scaffold 3043 and the distal end 3046b of the post and bringing the end 3046b into contact with the scaffold 3043 to further facilitate extraction of the scaffold 3043 from the sleeve 3044. The device 3070 is then removed, as shown by arrow 3070b, and later used to implant the scaffold 3043 into a patient.

Figure 42:
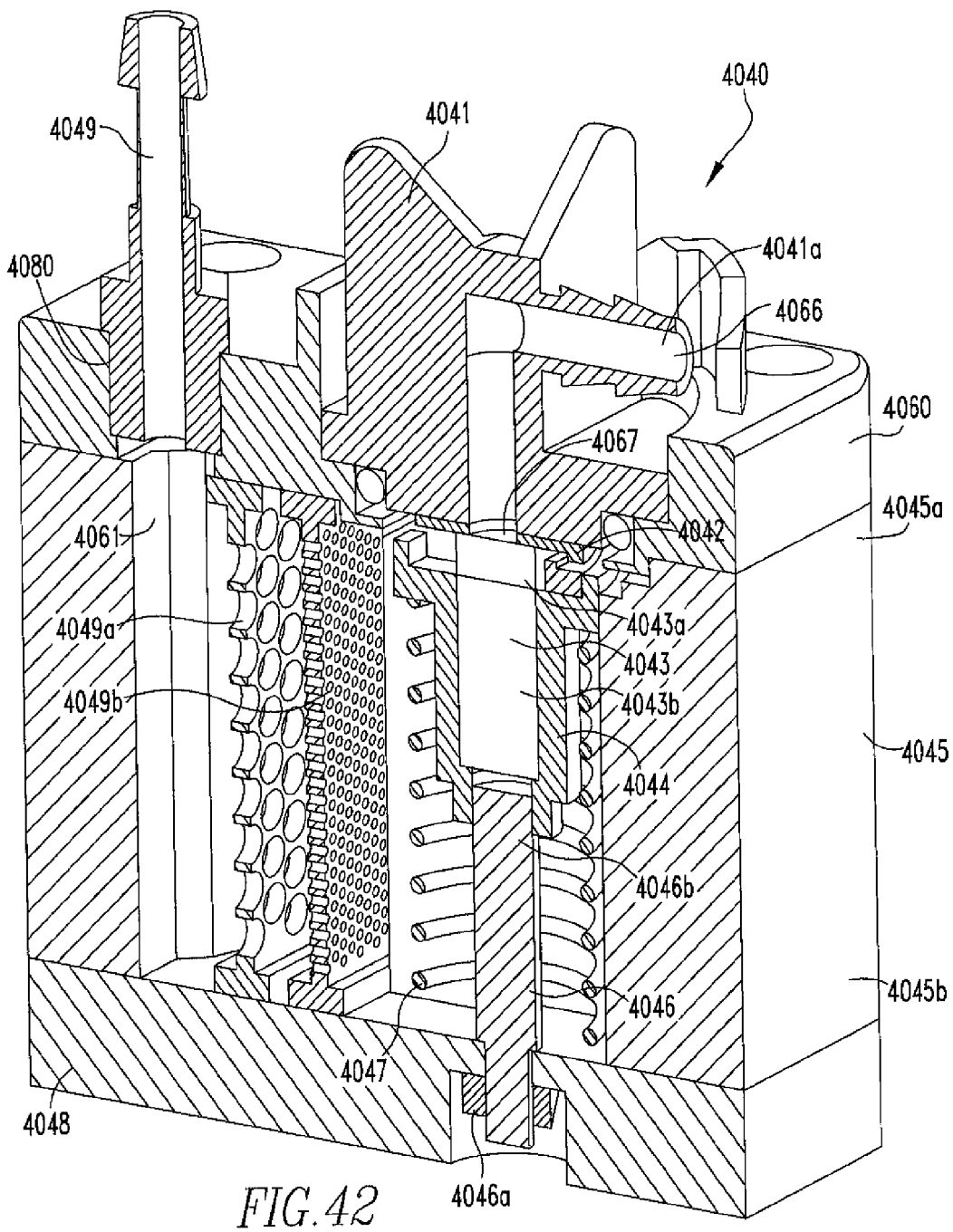
FIG. 42 is a cross-sectional view of the tissue collection apparatus of FIG. 34B.

FIG. 42 is a cross section of the tissue collection apparatus 4040 shown in FIG. 34B. The apparatus 4040 includes a housing 4045 having a distal end 4045a and a proximal end 4045b, a top portion 4060 coupled to the distal end 4045a, and a base portion 4048 coupled to the proximal end 4045b. The top portion 4060 includes an outlet cap 4041, having an outlet 4041a, and an inlet 4049. The housing 4045 includes an inner cavity 4061. A set of filters 4049a, 4049b are located in the inner cavity 4061 of the housing 4045. The filters 4049a, 4049b are coupled to the cavity 4061 via an adhesive, interference friction fit, or other suitable method. When there is a set of filters, the first filter 4049a has a set of openings having an opening size of between about 600 μm to about 3 mm. The second filter 4049b has a set of openings having an opening size of between about 600 μm to about 1 mm. The first filter 4049a catches the larger tissue particles first and allows the more moderate size tissue particles to be caught by the second filter 4049b. If there is only one filter, the larger tissue particles may tend to clog the filter more quickly. The flow of tissue through the apparatus 4040 will be further described below.

Figure 43:
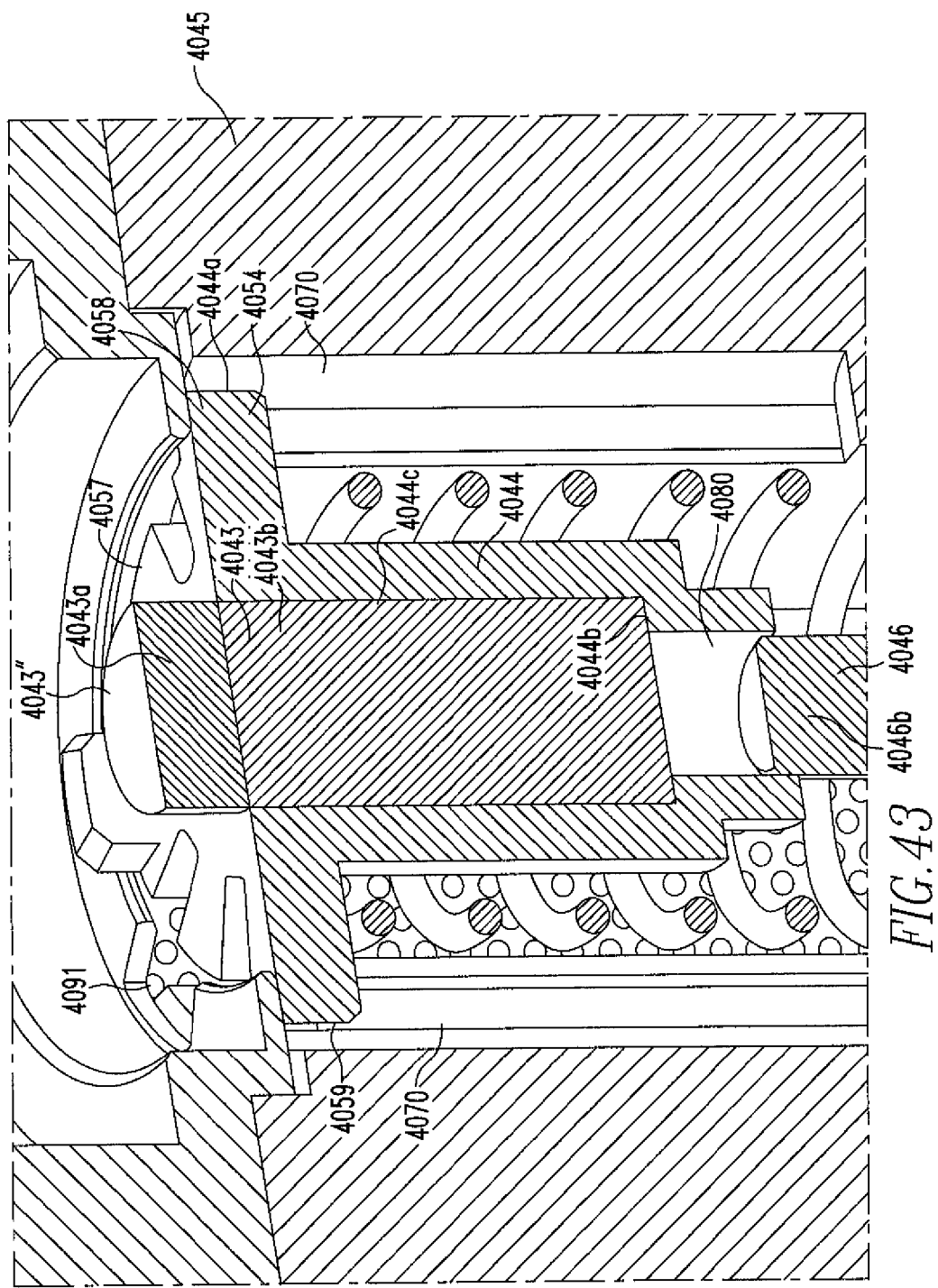
FIG. 43 is a cross-sectional view showing the scaffold and sleeve of the tissue collection apparatus of FIG. 34B.
Figure 45:
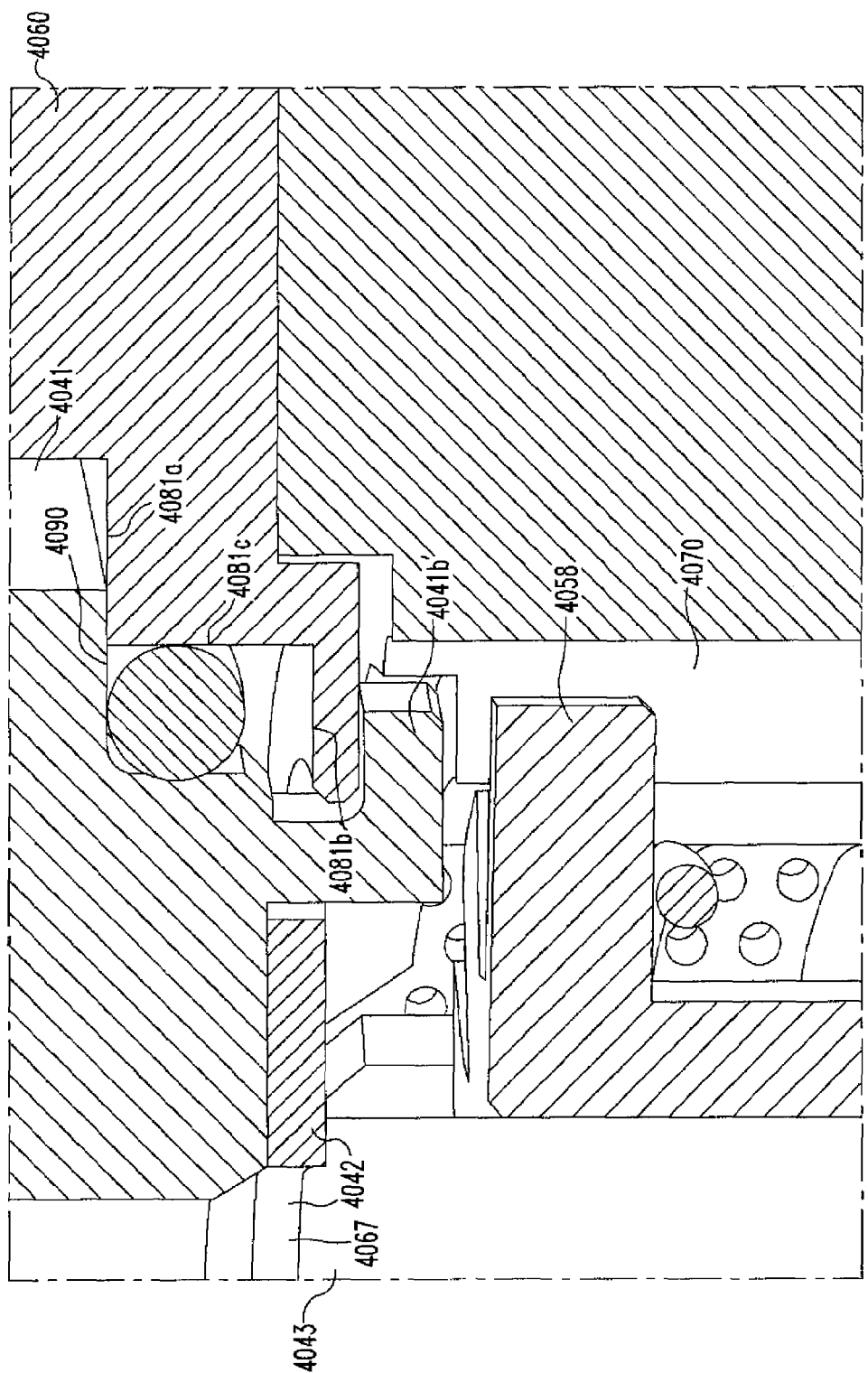
FIG. 45 is a cross-sectional view showing the overlap between the housing and the sleeve arm of the tissue collection apparatus of FIG. 34B.

Also located within the cavity 4061 is a spring 4047 that extends a length of the cavity 4061, a post 4046, and a sleeve 4044. The spring 4047 facilitates axial movement of the sleeve 4044 within the cavity 4061 during coupling and removal of the cap 4041, as will be further described below. The post 4046 is similar to the post 3046 in apparatus 3040, such that the post 4046 has a radially extending proximal portion 4046a and a distal portion 4046b and is housed within a through hole 4062 in the base portion 4048. The proximal portion 4046a is located within the base portion 3045a and the distal portion 4046b is located within the inner cavity 4061 of the housing 4045. The sleeve 4044 includes a proximal end 4044b configured for engagement with the distal portion 4046b of the post 4046 and a distal end 4044a having tabs 4057 (FIG. 43) and first and second arms 4058,4059 extending from the distal end 4044a. As shown in FIGS. 43 and 45, the arms 4058,4059 of the sleeve 4044 are housed within slots 4070 located in the housing 4045 such that an overlap is created between the arms 4058, 4059 and the housing 4045. This overlap substantially reduces the possibility of the sleeve 4044 from rotating and, in connection with the slots 4070, allows for axial movement of the sleeve 4044 during coupling and removal of the cap 4041 to the apparatus 4040, as will be further described below.

A tissue scaffold 4043, as described above, is located within an internal cavity 4044c of the sleeve 4044 such that a second region 4043b of the scaffold 4043 is contained within the sleeve 4043 and a first region 4043a extends from the distal end 4044a of the sleeve 4044. The distal portion 4046b of the post 4046 extends into the inner cavity 4044c of the sleeve 4044 to substantially reduce the possibility of the scaffold 4043 becoming lodged within the inner cavity 4044c of the sleeve 4044 during extraction of the scaffold 4043 from the sleeve 4044, as will be further described below. As shown in FIGS. 42 and 43, a gap 4080 is located between the distal end 4046b of the post 4046 and the scaffold 4043. The gap 4080 allows for axial movement of the sleeve 4044 when the outlet cap 4041 is rotated and removed from the housing 4045, as will be further described below.

Figure 44:
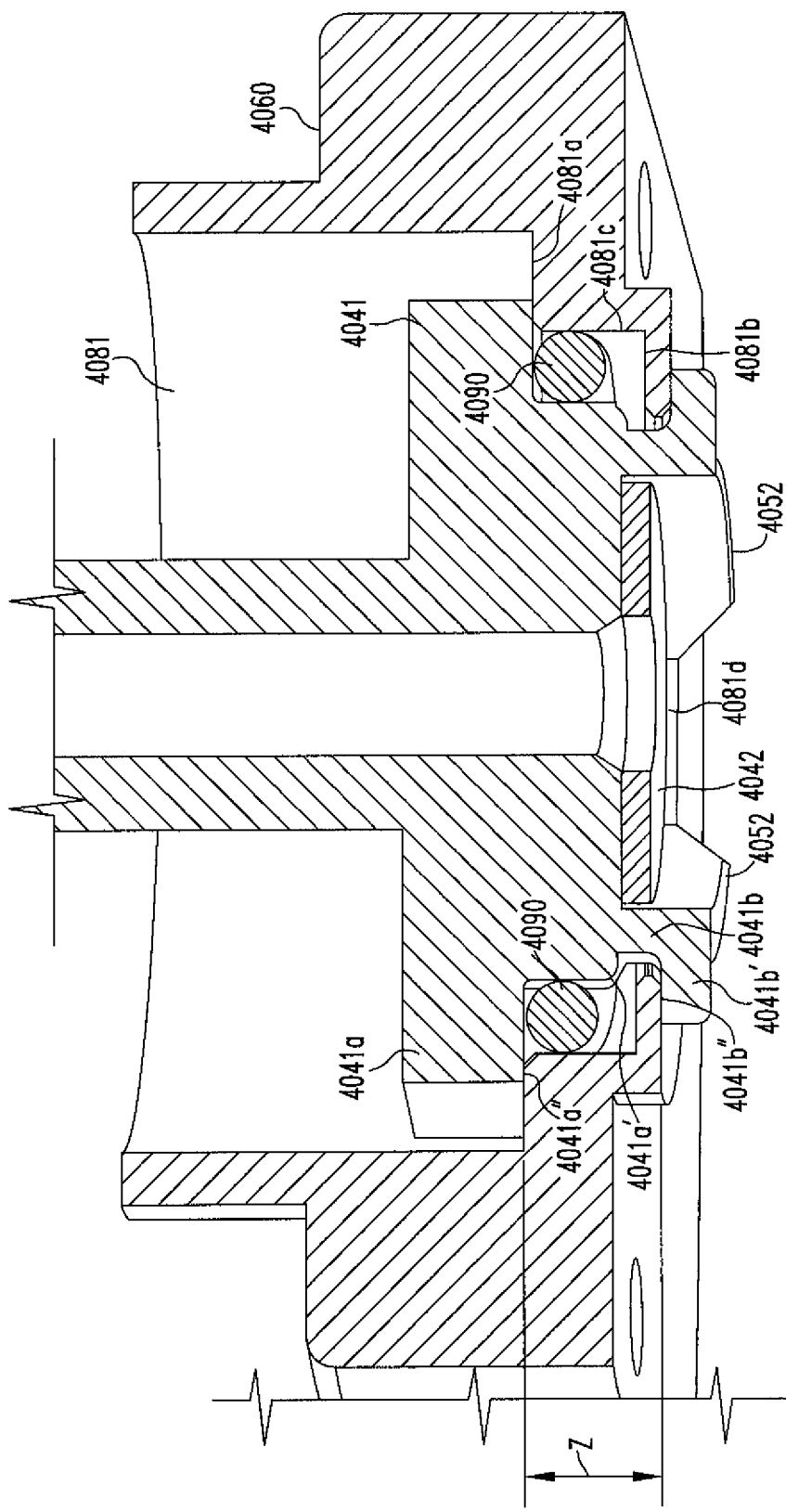
FIG. 44 is a cross-sectional view of the outlet cap and the second depression of the tissue collection apparatus of FIG. 34B.

The top portion 4060 includes a first depression 4080 for receiving the inlet 4049 and a second depression 4081 for receiving the outlet cap 4041 (FIG. 44). The second depression 4081 includes a first ledge 4081a, a second ledge 4081b, a wall 4081c located between the first and second ledges 4081a,4081b, and an opening 4081d. The outlet cap 4041 includes a first portion 4041a having an area of reduced diameter 4041a' and a second portion 4041b, having radially extending arms 4041b', extending from the first portion 4041a. The first portion 4041a also includes an O-ring 4090 coupled to the area of reduced diameter 4041a'. The cap 4041 is received within the second depression 4081 such that the radially extending arms 4041b' are disposed within the opening 4081d and are engaged with the second ledge 4081b, the O-ring 4090 is engaged with the wall 4081c, and the first portion 4041a is engaged with the first ledge 4081a.

When the outlet cap 4041 is disposed within the second depression 4081, the O-ring 4090 is compressed radially between the cap 4041 and the wall 4081c of the depression 4080, thereby providing a fluid seal between the cap 4041 and the depression 4080. In this manner, as shown in FIGS. 44 and 45, radial compression of the O-ring 4090 is greater on the cap 4041 than on the wall 4081c, thereby substantially increasing the possibility of the O-ring 4090 remaining coupled to the cap 4041 when the cap 4041 is removed, as will be further described below. The axial location of the outlet cap 4041 is set by Z'', or the distance between surfaces 4041a'', 4041b'' on the first portion 4041a and the radially extending arms 4041b' of the outlet cap 4041, respectively. Retention features, other than an O-ring, are within the scope of this disclosure and may be used.

Figure 46:
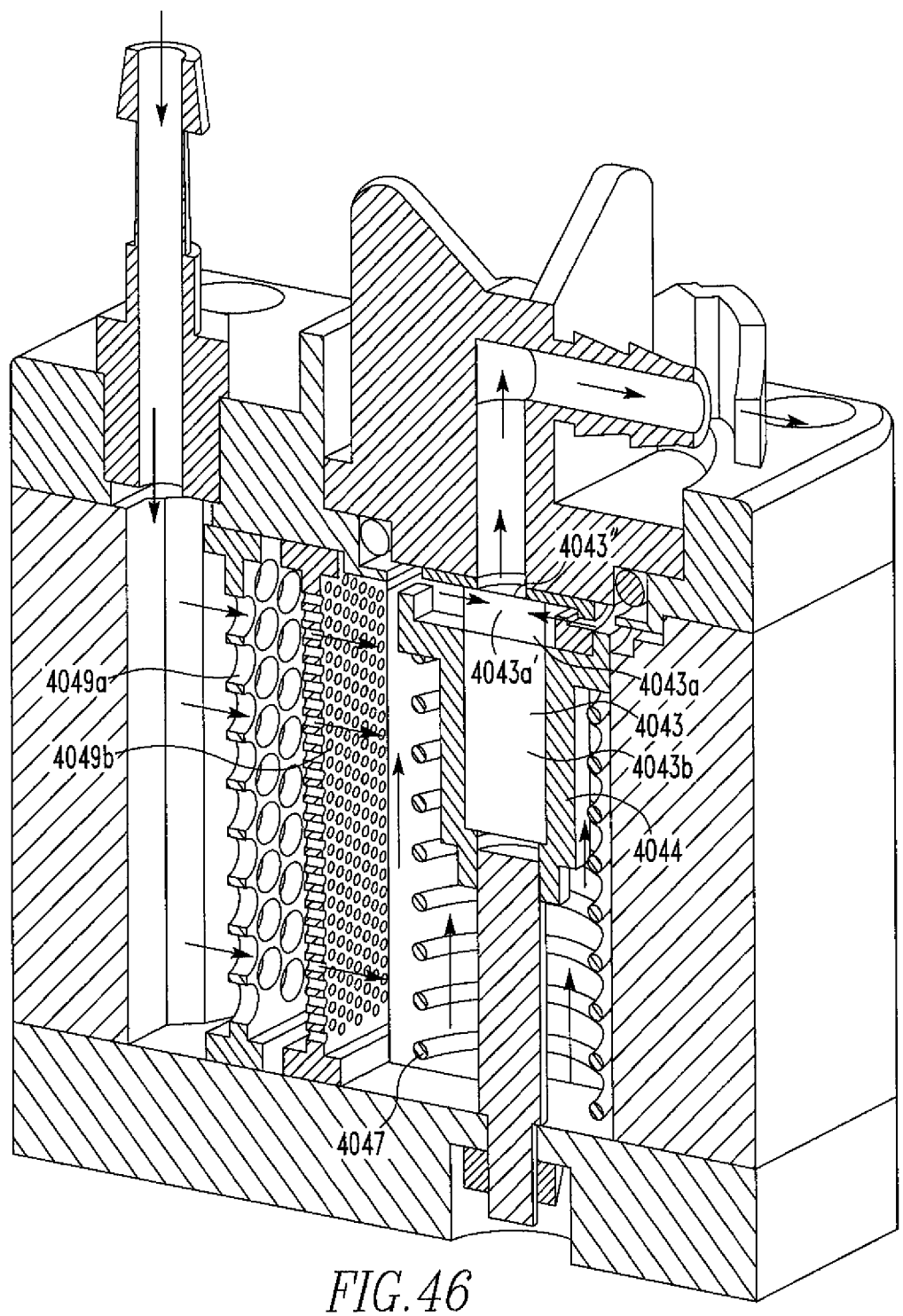
FIG. 46 is a cross-sectional view illustrating the flow of tissue and fluid through the tissue collection apparatus of FIG. 34B.

Located between the cap 4041 and the housing 4045 is a scaffold gasket 4042. As shown in FIGS. 42 and 44, the scaffold gasket 4042 includes a through hole 4067, such that the through hole 4067 of the gasket 4042 is aligned with the through hole 4066 of the outlet 4041a. FIGS. 42 and 46 show a radial overlap which exists between the first region 4043a of the scaffold 4043 and the scaffold gasket 4042. The overlap is large enough to substantially reduce the scaffold 4043 from extending through the through hole 4067, yet small enough to substantially reduce blocking of the pores in the first region 4043a of the scaffold 4043. In terms of size, the overlap remains the same independent of the diameter of the scaffold 4043, with the overlap covering up to about 10% of the diameter of the scaffold 4043.

FIG. 44 shows the location of ramps 4052 that are coupled to the cap 4041. These ramps 4052 cover almost 180° of rotation so that the scaffold 4043 is only in contact with the scaffold gasket 4042 over a small angle of rotation, as will be further described below. This substantially reduces the possibility of damage to the open face 4043'' of the scaffold 4043 when the cap 4041 is inserted onto and removed from the shaft 4045b, as will be further described below.

In operation, the surgical blade 10 (FIG. 1) is brought into contact with a desired bodily tissue, such as adipose or synovial tissue. The operator cuts a desired amount of tissue from the donor site using the blade 10. The vacuum source 70 (FIG. 1) aspirates the fluid and the cut tissue through the filters 4049a,4049b, which remove cut tissue that is larger than the opening sizes of the filters, from the fluid pathway. The cut tissue and fluid flow over and around the exterior of the sleeve 4044 and enter the side 4043a' of the first region 4043a of the tissue scaffold 4043 (as depicted by the arrows in FIG. 46). Because the sleeve 4044 completely surrounds the exterior of the second region 4043b of the tissue scaffold 4043, and because the bonding agent (e.g., adhesive) between the first region 4043a and the second region 4043b of the tissue scaffold 4043 minimizes flow of tissue and fluid therethrough, the cut tissue and fluid flows through the first region 4043a of the tissue scaffold 4043. In particular, the tissue and fluid flow through the side 4043a' of the first region 4043a and out of the circular face 4043'' (FIG. 46), thereby loading only the first region 4043a, including the interior and exterior of the first region 4043a, with cut tissue for later implantation into the desired site to be treated.

FIGS. 47A-D illustrate the use of the apparatus 4040 by a surgeon. The scaffold 4043 is pre-loaded under sterile conditions in a manufacturing facility within sleeve 4044 such that a portion, at least part of the cartilage phase or first region 4043a, of the scaffold 4043 protrudes from the sleeve 4044. Prior to use of the apparatus 4040, the cap 4041 is coupled to the apparatus 4040, such that the ramps 4052 are not in contact with the arms 4058,4059 of the sleeve 4044 and the scaffold 4043 is not under pressure by the gasket 4042 and the cap 4041. Rather, the arms 4058,4059 are disposed within the cut-out portions 4091 (FIG. 43) of the second depression 4081. In anticipation of use of apparatus 4040, the surgeon turns the cap 4041 clockwise about 45°, as shown by the arrow in FIG. 47A, such that the ramps 4052 and arms 4041b'engage tabs 4057 and arms 4058,4059 thereby facilitating axial movement of the sleeve 4044 within the cavity 4061 and an application of pressure on the scaffold 4043 by cap 4041 and gasket 4042. In addition to the ramps 4052 and arms 4041b', as described above, the O-ring 4090 applies pressure, via radial compression, to the wall 4081c to couple the cap 4041 to the apparatus 4040. Tubes, as described above and represented by arrows in FIG. 47B, are coupled to the inlet 4049 and the outlet 4041a on the cap 4041 and tissue is harvested, in the manner described above.

After the scaffold 4043 has been loaded with tissue, the cap 4041 is removed by turning the cap 4041 anti-clockwise about 90°, as shown by the arrow in FIG. 47C, such that the ramps 4052 and arms 4041b' are disengaged from the sleeve 4044 and pressure is released from the scaffold 4043. A tissue scaffold delivery device 4070 (FIG. 47D), as described above and shown in FIG. 9A, is used to remove the tissue seeded-scaffold 4043 from sleeve 4044 such that an end 4070a of the device 4070 is placed over the scaffold 4043 and downward pressure is applied to the device 4070 to insert the scaffold 4043 into the end 4070a of the device 4070. While the downward pressure is applied to the device 4070, movement of the sleeve 4044 occurs within the cavity 4061, thereby substantially reducing the gap 4060 between the scaffold 4043 and the distal end 4046b of the post and bringing the end 4046b into contact with the scaffold 4043 to further facilitate extraction of the scaffold 4043 from the sleeve 4044. The device 4070 is then removed and later used to implant the scaffold 4043 into a patient.

A number of implementations of the disclosure have been described. Nevertheless, it will be understood that various modifications may be made without departing from the spirit and scope of the disclosure. For example, although the tissue scaffolds 46, 1046, 3043, 4043 have been illustrated as disposed in the tissue collection apparatus 40, 1040, 3040, 4040 respectively, with material 46a or first region 1046a, 3043a, 4043a closest to the inlet of tissue collection apparatus 40, 1040, 3040, 4040 respectively, tissue scaffolds 46, 1046, 3043, 4043 can be reversed so that material 46b or second region 1046b, 3043b, 4043b is closest to the inlet. In addition, although the tissue scaffolds 46, 1046, 3043, 4043 have been described as permeable, other tissue scaffolds may be employed that exhibit semi-permeable or substantially non-permeable characteristics.

Moreover, although the tissue scaffold 46 has been described as being disposed in the housing 42 such that there is about 0.5 mm spacing between the inner surface of the housing 42 and the outer surface 46c of the tissue scaffold 46, the tissue scaffold 46 could be disposed with minimal spacing between the scaffold 46 and the inner surface of housing 42 such that cut tissue would load the scaffold 46 through the front face of scaffold 46.

Rather than the tubing connector 29 (FIGS. 4 and 5) being in communication with the aspiration lumen 16 of the inner tubular member 14 via the chamber 26, the tubing connector 29 could be directly coupled to the inner tubular member 14. The tubing connector 29 can be coupled to the side port 24 using any suitable form of connection, including glue, weld, press fit, or, alternatively, the tubing connector 29 can be formed as one piece with the hub 22. In addition, tubing connectors 47, 49 can be coupled to the inlet connector 44 and the outlet cap 48, respectively, using any suitable form of connection, including glue, weld, press fit, or, alternatively, the tubing connectors 47, 49 can be formed as one piece with the inlet connector 44 and the outlet cap 48, respectively. The tubing connectors described herein can be made from plastic, metal, or any other suitable materials.

The extension 54 of the inlet connector 44 can be molded as one piece or separate from the inlet connector 44. If separate, the extension 54 can be coupled to the inlet connector 44 using glue, press-fit, weld, or another suitable connection method. In addition, the extension 54 of the inlet connector 44 can be molded as one piece with or separate from the hub 22. If separate, the extension 54 can be coupled to the hub 22 using glue, press-fit, weld, or another suitable connection method.

The outlet cap 48 can be permanently or removable coupled to the housing 42. The size of the one or more openings 45, 45a formed in inner tubular member 14 can be of any size to provide sufficient aspiration of fluid and cut tissue from the aspiration lumen 16. The tissue collection device 40 can contain various sizes and types of scaffold.

In addition, although the tissue harvesting assembly has been described as including a surgical blade 10 used to cut or resect bodily tissue, such as soft tissue, the tissue harvesting assembly can include an apparatus containing a curet or burr, for example, to removing bodily tissue, such as bone tissue.

Further, for each of the sleeve implementations described above (e.g., FIGS. 11, 12, 20A-20C, 21A-21C), the tissue scaffold 1046 can be removed from the sleeve without first removing the sleeve from the delivery device housing 1042.

The components of the apparatuses shown in FIGS. 34-47 may include a metal or non-metal material and may be made via a molding process, such as injection molding, or other process known to one of skill in the art. In addition, the top portion 4060 and base portion 4048 may be coupled to the housing 4045 via a press-fit or other type of coupling method. Similarly, the inlet 4049 may be coupled to the top portion 4060 by a press-fit, adhesive, interference fit, or other type of coupling method known to one of skill in the art.

Accordingly, other embodiments are within the scope of the following claims.

What is claimed is:

1. A tissue collection apparatus comprising: a housing defining an inlet and an outlet, the housing including a post, a sleeve slidable along the post, and a spring surrounding at least portions of the post and the sleeve; and a tissue scaffold suitable for disposal within an internal cavity of the sleeve, the tissue scaffold configured to be loaded with tissue under the application of an aspiration force applied through the tissue collection apparatus, wherein the spring surrounds an exterior portion of the post, an exterior portion of the sleeve, and an exterior portion of the tissue scaffold.

2. A tissue collection apparatus comprising: a housing defining an inlet and an outlet, the housing including a post, a sleeve slidable along the post, and a spring surrounding at least portions of the post and the sleeve; and a tissue scaffold suitable for disposal within an internal cavity of the sleeve, the tissue scaffold configured to be loaded with tissue under the application of an aspiration force applied through the tissue collection apparatus, wherein the tissue scaffold has a first exterior surface and a second exterior surface;

wherein the housing defines a flow path between the inlet and the outlet such that, under the application of the aspiration force, fluid enters the tissue scaffold through the first exterior surface and exits the tissue scaffold through the second exterior surface.

3. A tissue collection apparatus comprising: a housing defining an inlet and an outlet, the housing including a post, a sleeve slidable along the post, and a spring surrounding at least portions of the post and the sleeve; and a tissue scaffold suitable for disposal within an internal cavity of the sleeve, the tissue scaffold configured to be loaded with tissue under the application of an aspiration force applied through the tissue collection apparatus, wherein the tissue scaffold defines a central longitudinal axis, and the housing defines a flow path between the inlet and the outlet such that, under the application of the aspiration force, fluid enters the tissue scaffold in a direction radially inward toward the central longitudinal axis.

4. A tissue collection apparatus comprising: a housing defining an inlet and an outlet, the housing including a post, a sleeve slidable along the post, and a spring surrounding at least portions of the post and the sleeve; and a tissue scaffold suitable for disposal within an internal cavity of the sleeve, the tissue scaffold configured to be loaded with tissue under the application of an aspiration force applied through the tissue collection apparatus, the sleeve being moveable relative to the post to release the tissue scaffold, wherein the tissue scaffold has a first portion and a second portion, the first portion being receivable in the internal cavity of the sleeve and the second portion extending out of the internal cavity when the first portion is disposed in the internal cavity, wherein the sleeve is configured to block fluid flow into the first portion when the first portion is disposed in the internal cavity.

5. A tissue collection apparatus comprising: a housing defining an inlet and an outlet, the housing including a post, a sleeve slidable along the post, and a spring surrounding at least portions of the post and the sleeve; and a tissue scaffold suitable for disposal within an internal cavity of the sleeve, the tissue scaffold configured to be loaded with tissue under the application of an aspiration force applied through the tissue collection apparatus, the housing defining a flow path between the inlet and the outlet that directs fluid along an exterior surface of the sleeve.

6. The tissue collection apparatus of claim 5, wherein the housing defines the flow path such that, under the application of the aspiration force, fluid flows from the inlet, over the exterior of the sleeve, through a portion of the tissue scaffold, and through the outlet.

7. The tissue collection apparatus of claim 5, wherein the tissue scaffold has an outer surface, and the housing defines the flow path such that, under the application of the aspiration force, fluid enters the tissue scaffold radially inward through the outer surface.

8. The tissue collection apparatus of claim 5, wherein the tissue scaffold has a circular face, and the housing defines the flow path such that, under the application of the aspiration force, fluid exits the tissue scaffold through the circular face.

9. The tissue collection apparatus of claim 5, wherein the spring is disposed to contact fluid in the flow path.

\* \* \* \* \*